(12) United States Patent
Fujikura et al.

(10) Patent No.: US 7,465,713 B2
(45) Date of Patent: Dec. 16, 2008

(54) GLUCOPYRANOSYLOXYPYRAZOLE DERIVATIVES AND USE THEREOF IN MEDICINES

(75) Inventors: Hideki Fujikura, Nagano (JP); Nobuhiko Fushimi, Nagano (JP); Toshihiro Nishimura, Nagano (JP); Takeshi Nakabayashi, Nagano (JP); Masayuki Isaji, Nagano (JP)

(73) Assignee: Kissei Pharmaceutical Co., Ltd., Nagano (JP)

( * ) Notice: Subject to any disclaimer, the term of this patent is extended or adjusted under 35 U.S.C. 154(b) by 0 days.

(21) Appl. No.: 11/247,216

(22) Filed: Oct. 12, 2005

(65) Prior Publication Data

US 2006/0025352 A1 Feb. 2, 2006

Related U.S. Application Data

(62) Division of application No. 10/451,926, filed as application No. PCT/JP01/11348 on Dec. 25, 2001, now Pat. No. 7,084,123.

(30) Foreign Application Priority Data

Dec. 28, 2000 (JP) ............................. 2000-403534

(51) Int. Cl.
*A01N 43/04* (2006.01)
*A61K 31/70* (2006.01)

(52) U.S. Cl. ............................. 514/27; 514/25; 514/35
(58) Field of Classification Search ............... 514/25, 514/27, 35
See application file for complete search history.

(56) References Cited

U.S. PATENT DOCUMENTS

| | | | |
|---|---|---|---|
| 5,264,451 A | 11/1993 | Kees | |
| 5,424,406 A | 6/1995 | Tsujihara et al. | |
| 6,683,056 B2 * | 1/2004 | Washburn et al. | 514/25 |
| 6,815,428 B2 | 11/2004 | Ohsumi et al. | |
| 2003/0087843 A1 | 5/2003 | Washburn | |
| 2004/0006025 A1 | 1/2004 | Ohsumi et al. | |
| 2004/0063646 A1 | 4/2004 | Fujikura et al. | |
| 2005/0043249 A1 | 2/2005 | Ohsumi et al. | |

FOREIGN PATENT DOCUMENTS

| | | |
|---|---|---|
| EP | 0 449 699 A2 | 10/1991 |
| WO | WO 01/16147 A1 | 8/2001 |
| WO | WO 02/036602 A1 | 10/2002 |
| WO | WO 02/053573 A1 | 11/2002 |
| WO | WO 03/020737 A1 | 3/2003 |

OTHER PUBLICATIONS

New Potent Antihyperglycemic Agents in db/db Mice: Synthesis and Structure-Activity Relationship Studies of (4-Substituted benzyl)(trifluoromethyl) pyrazoles and -pyrazolones; J. Med. Chem. 1996, 39, 3920-2938.
Harold E. Lebovitz, MD: Stepwise and Combination Drug Therapy for the Treatment of NIDDM; Diabetes Care, vol. 17, No. 12, Dec. 1994; pp. 1542-1544.
Nigishi Hotta; Chronic Disease, vol. 6, No. 1, pp. 98-102 (1995).
Nigishi Hotta, Tonyobyo Update 10, pp. 68-77 (1994).
Cecilia A. Hofmann, PhD, et al; New Oral Thiazolidinedione Antidiabetic Agents Act as Insulin Sensitizers, Diabetes Care, vol. 15, No. 8, Aug. 1992; pp. 1075-1078.
Gareth Williams; Management of non-insulin-dependent diabetes mellitus; The Lancet; vol. 343; Jan. 8, 1994; pp. 95-100.

* cited by examiner

*Primary Examiner*—Shaojia Anna Jiang
*Assistant Examiner*—Traviss C McIntosh, III
(74) *Attorney, Agent, or Firm*—Sughrue Mion, PLLC

(57) ABSTRACT

The present invention provides glucopyranosyloxypyrazole derivatives represented by the general formula:

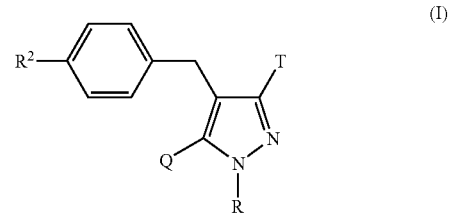

(I)

wherein R represents a hydrogen atom, a lower alkyl group or a group forming a prodrug; one of Q and T represents a

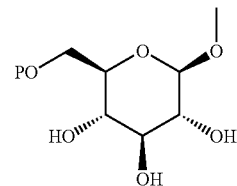

group represented by the general formula:
(wherein P represents a hydrogen atom or a group forming a prodrug), while the other represents a lower alkyl group or a halo(lower alkyl) group; $R^2$ represents a hydrogen atom, a lower alkyl group, a lower alkoxy group, a lower alkylthio group, a halo(lower alkyl) group or a halogen atom; and with the proviso that P does not represent a hydrogen atom when R represents a hydrogen atom or a lower alkyl group, or pharmaceutically acceptable salts thereof, which exert an inhibitory activity in human SGLT2 and have an improved oral absorption, and therefore are useful as agents for the prevention or treatment of a disease associated with hyperglycemia such as diabetes, diabetic complications or obesity, and pharmaceutically acceptable salts thereof, and pharmaceutical uses thereof.

15 Claims, No Drawings

GLUCOPYRANOSYLOXYPYRAZOLE DERIVATIVES AND USE THEREOF IN MEDICINES

The instant application is a divisional of U.S. application Ser. No. 10/451,926 filed Nov. 6, 2003, now U.S. Pat. No. 7,084,123 which is a 371 application of PCT/JP01/11348 filed Dec. 25, 2001.

TECHNICAL FIELD

The present invention relates to glucopyranosyloxypyrazole derivatives or pharmaceutically acceptable salts thereof which are useful as medicaments and pharmaceutical uses thereof.

More particularly, the present invention relates to glucopyranosyloxypyrazole derivatives represented by the general formula:

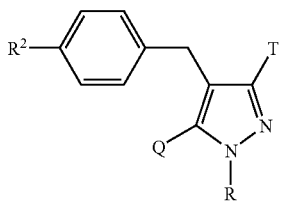

(I)

wherein R represents a hydrogen atom, a lower alkyl group or a group forming a prodrug; one of Q and T represents a group represented by the general formula:

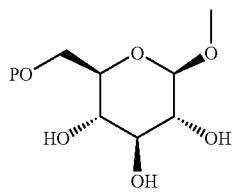

(wherein P represents a hydrogen atom or a group forming a prodrug), while the other represents a lower alkyl group or a halo(lower alkyl) group; $R^2$ represents a hydrogen atom, a lower alkyl group, a lower alkoxy group, a lower alkylthio group, a halo(lower alkyl) group or a halogen atom; and with the proviso that P does not represent a hydrogen atom when R represents a hydrogen atom or a lower alkyl group, or pharmaceutically acceptable salts thereof, which are useful as agents for the prevention or treatment of a disease associated with hyperglycemia such as diabetes, diabetic complications or obesity, of which glucopyranosyloxypyrazole derivatives, which have an inhibitory activity in human SGLT2, represented by the general formula:

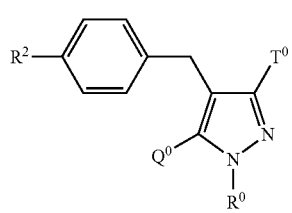

(II)

wherein $R^0$ represents a hydrogen atom or a lower alkyl group; one of $Q^0$ and $T^0$ represents a group represented by the general formula:

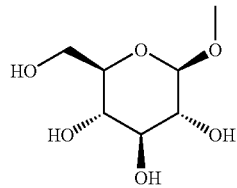

while the other represents a lower alkyl group or a halo(lower alkyl) group; and $R^2$ represents a hydrogen atom, a lower alkyl group, a lower alkoxy group, a lower alkylthio group, a halo(lower alkyl) group or a halogen atom, are active forms, and to pharmaceutical uses thereof.

BACKGROUND ART

Diabetes is one of lifestyle-related diseases with the background of change of eating habit and lack of exercise. Hence, diet and exercise therapies are performed in patients with diabetes. Furthermore, when its sufficient control and continuous performance are difficult, drug treatment is simultaneously performed. Now, biguanides, sulfonylureas and insulin sensitivity enhancers have been employed as antidiabetic agents. However, biguanides and sulfonylureas show occasionally adverse effects such as lactic acidosis and hypoglycemia, respectively. In a case of using insulin sensitivity enhancers, adverse effects such as edema occasionally are observed, and it is also concerned for advancing obesity. Therefore, in order to solve these problems, it has been desired to develop antidiabetic agents having a new mechanism.

In recent years, development of new type antidiabetic agents has been progressing, which promote urinary glucose excretion and lower blood glucose level by preventing excess glucose reabsorption at the kidney (J. Clin. Invest., Vol. 79, pp. 1510-1515 (1987)). In addition, it is reported that SGLT2 ($Na^+$/glucose cotransporter 2) is present in the S1 segment of the kidney's proximal tubule and participates mainly in reabsorption of glucose filtrated through glomerular (J. Clin. Invest., Vol. 93, pp. 397-404 (1994)). Accordingly, inhibiting a human SGLT2 activity prevents reabsorption of excess glucose at the kidney, subsequently promotes excreting excess glucose though the urine, and normalizes blood glucose level. Therefore, fast development of antidiabetic agents, which have a potent inhibitory activity in human SGLT2 and have a new mechanism, has been desired. Also, since such agents promote the excretion of excess glucose though the urine and consequently the glucose accumulation in the body is decreased, they are also expected to have a preventing or alleviating effect on obesity and a urinating effect. Furthermore, the agents are considered to be useful for various related diseases which occur accompanying the progress of diabetes or obesity due to hyperglycemia.

As compounds having pyrazole moiety, it is described that WAY-123783 increased an amount of excreted glucose in normal mice. However, its effects in human are not described at all (J. Med. Chem., Vol. 39, pp. 3920-3928 (1996)).

DISCLOSURE OF THE INVENTION

The present inventors have studied earnestly to find compounds having an inhibitory activity in human SGLT2. As a result, it was found that compounds represented by the above general formula (I) are converted into glucopyranosyloxypyrazole derivatives represented by the above general formula (II) as their active forms in vivo, and show an excellent inhibitory activity in human SGLT2 as mentioned below, thereby forming the basis of the present invention.

The present invention is to provide the following glucopyranosyloxypyrazole derivatives or pharmaceutically acceptable salts thereof, which exert an inhibitory activity in human SGLT2 in vivo and show an excellent hypoglycemic effect by excreting excess glucose in the urine through preventing the reabsorption of glucose at the kidney, and to provide pharmaceutical uses thereof.

This is, the present invention relates to a glucopyranosyloxypyrazole derivative represented by the general formula:

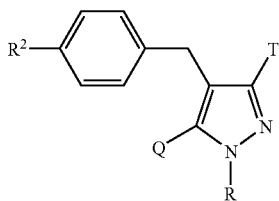

(I)

wherein R represents a hydrogen atom, a lower alkyl group or a group forming a prodrug; one of Q and T represents a group represented by the general formula:

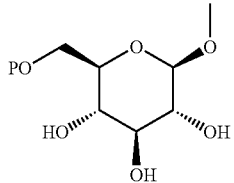

(wherein P represents a hydrogen atom or a group forming a prodrug), while the other represents a lower alkyl group or a halo(lower alkyl) group; $R^2$ represents a hydrogen atom, a lower alkyl group, a lower alkoxy group, a lower alkylthio group, a halo(lower alkyl) group or a halogen atom; and with the proviso that P does not represent a hydrogen atom when R represents a hydrogen atom or a lower alkyl group, or a pharmaceutically acceptable salt thereof.

Also, the present invention relates to a pharmaceutical composition, a human SGLT2 inhibitor and an agent for the prevention or treatment of a disease associated with hyperglycemia, which comprise as an active ingredient a glucopyranosyloxypyrazole derivative represented by the above general formula (I) or a pharmaceutically acceptable salt thereof.

The present invention relates to a method for the prevention or treatment of a disease associated with hyperglycemia, which comprises administering an effective amount of a glucopyranosyloxypyrazole derivative represented by the above general formula (I) or a pharmaceutically acceptable salt thereof.

The present invention relates to a use of a glucopyranosyloxypyrazole derivative represented by the above general formula (I) or a pharmaceutically acceptable salt thereof for the manufacture of a pharmaceutical composition for the prevention or treatment of a disease associated with hyperglycemia.

Furthermore, the present invention relates to a pharmaceutical combination which comprises (A) a glucopyranosyloxypyrazole derivative represented by the above general formula (I) or a pharmaceutically acceptable salt thereof, and (B) at least one member selected from the group consisting of an insulin sensitivity enhancer, a glucose absorption inhibitor, a biguanide, an insulin secretion enhancer, an insulin preparation, a glucagon receptor antagonist, an insulin receptor kinase stimulant, a tripeptidyl peptidase II inhibitor, a dipeptidyl peptidase IV inhibitor, a protein tyrosine phosphatase-1B inhibitor, a glycogen phosphorylase inhibitor, a glucose-6-phosphatase inhibitor, a fructose-bisphosphatase inhibitor, a pyruvate dehydrogenase inhibitor, a hepatic gluconeogenesis inhibitor, D-chiroinsitol, a glycogen synthase kinase-3 inhibitor, glucagon-like peptide-1, a glucagon-like peptide-1 analogue, a glucagon-like peptide-1 agonist, amylin, an amylin analogue, an amylin agonist, an aldose reductase inhibitor, an advanced glycation endproducts formation inhibitor, a protein kinase C inhibitor, a γ-aminobutyric acid receptor antagonist, a sodium channel antagonist, a transcript factor NF-κB inhibitor, a lipid peroxidase inhibitor, an N-acetylated-α-linked-acid-dipeptidase inhibitor, insulin-like growth factor-I, platelet-derived growth factor, a platelet-derived growth factor analogue, epidermal growth factor, nerve growth factor, a carnitine derivative, uridine, 5-hydroxy-1-methylhidantoin, EGB-761, bimoclomol, sulodexide, Y-128, a hydroxymethyl-glutaryl coenzyme A reductase inhibitor, a fibric acid derivative, a $\beta_3$-adrenoceptor agonist, an acyl-coenzyme A cholesterol acyltransferase inhibitor, probcol, a thyroid hormone receptor agonist, a cholesterol absorption inhibitor, a lipase inhibitor, a microsomal triglyceride transfer protein inhibitor, a lipoxygenase inhibitor, a carnitine palmitoyl-transferase inhibitor, a squalene synthase inhibitor, a low-density lipoprotein receptor enhancer, a nicotinic acid derivative, a bile acid sequestrant, a sodium/bile acid cotransporter inhibitor, a cholesterol ester transfer protein inhibitor, an appetite suppressant, an angiotensin-converting enzyme inhibitor, a neutral endopeptidase inhibitor, an angiotensin II receptor antagonist, an endothelin-converting enzyme inhibitor, an endothelin receptor antagonist, a diuretic agent, a calcium antagonist, a vasodilating antihypertensive agent, a sympathetic blocking agent, a centrally acting antihypertensive agent, an $\alpha_2$-adrenoceptor agonist, an antiplatelets agent, a uric acid synthesis inhibitor, a uricosuric agent and a urinary alkalinizer.

The present invention relates to a method for the prevention or treatment of a disease associated with hyperglycemia, which comprises administering an effective amount of (A) a glucopyranosyloxypyrazole derivative represented by the above general formula (I) or a pharmaceutically acceptable salt thereof, in combination with (B) at least one member selected from the group consisting of an insulin sensitivity enhancer, a glucose absorption inhibitor, a biguanide, an insulin secretion enhancer, an insulin preparation, a glucagon receptor antagonist, an insulin receptor kinase stimulant, a tripeptidyl peptidase II inhibitor, a dipeptidyl peptidase IV inhibitor, a protein tyrosine phosphatase-1B inhibitor, a glycogen phosphorylase inhibitor, a glucose-6-phosphatase inhibitor, a fructose-bisphosphatase inhibitor, a pyruvate dehydrogenase inhibitor, a hepatic gluconeogenesis inhibitor, D-chiroinsitol, a glycogen synthase kinase-3 inhibitor, glucagon-like peptide-1, a glucagon-like peptide-1 analogue, a glucagon-like peptide-1 agonist, amylin, an amylin analogue, an amylin agonist, an aldose reductase inhibitor, an advanced glycation endproducts formation inhibitor, a protein kinase C inhibitor, a γ-aminobutyric acid receptor antagonist, a sodium channel antagonist, a transcript factor NF-κB inhibitor, a lipid peroxidase inhibitor, an N-acetylated-α-linked-acid-dipeptidase inhibitor, insulin-like growth factor-I, platelet-derived growth factor, a platelet-derived growth factor analogue, epidermal growth factor, nerve growth factor, a carnitine derivative, uridine, 5-hydroxy-1-methylhidantoin, EGB-761, bimoclomol, sulodexide, Y-128, a hydroxymethyl-glutaryl coenzyme A reductase inhibitor, a fibric acid derivative, a β$_3$-adrenoceptor agonist, an acyl-coenzyme A cholesterol acyltransferase inhibitor, probcol, a thyroid hormone receptor agonist, a cholesterol absorption inhibitor, a lipase inhibitor, a microsomal triglyceride transfer protein inhibitor, a lipoxygenase inhibitor, a carnitine palmitoyl-transferase inhibitor, a squalene synthase inhibitor, a low-density lipoprotein receptor enhancer, a nicotinic acid derivative, a bile acid sequestrant, a sodium/bile acid cotransporter inhibitor, a cholesterol ester transfer protein inhibitor, an appetite suppressant, an angiotensin-converting enzyme inhibitor, a neutral endopeptidase inhibitor, an angiotensin II receptor antagonist, an endothelin-converting enzyme inhibitor, an endothelin receptor antagonist, a diuretic agent, a calcium antagonist, a vasodilating antihypertensive agent, a sympathetic blocking agent, a centrally acting antihypertensive agent, an α$_2$-adrenoceptor agonist, an antiplatelets agent, a uric acid synthesis inhibitor, a uricosuric agent and a urinary alkalinizer.

The present invention relates to a use of (A) a glucopyranosyloxypyrazole derivative represented by the above general formula (I) or a pharmaceutically acceptable salt thereof, and (B) at least one member selected from the group consisting of an insulin sensitivity enhancer, a glucose absorption inhibitor, a biguanide, an insulin secretion enhancer, an insulin preparation, a glucagon receptor antagonist, an insulin receptor kinase stimulant, a tripeptidyl peptidase II inhibitor, a dipeptidyl peptidase IV inhibitor, a protein tyrosine phosphatase-1B inhibitor, a glycogen phosphorylase inhibitor, a glucose-6-phosphatase inhibitor, a fructose-bisphosphatase inhibitor, a pyruvate dehydrogenase inhibitor, a hepatic gluconeogenesis inhibitor, D-chiroinsitol, a glycogen synthase kinase-3 inhibitor, glucagon-like peptide-1, a glucagon-like peptide-1 analogue, a glucagon-like peptide-1 agonist, amylin, an amylin analogue, an amylin agonist, an aldose reductase inhibitor, an advanced glycation endproducts formation inhibitor, a protein kinase C inhibitor, a γ-aminobutyric acid receptor antagonist, a sodium channel antagonist, a transcript factor NF-κB inhibitor, a lipid peroxidase inhibitor, an N-acetylated-α-linked-acid-dipeptidase inhibitor, insulin-like growth factor-I, platelet-derived growth factor, a platelet-derived growth factor analogue, epidermal growth factor, nerve growth factor, a carnitine derivative, uridine, 5-hydroxy-1-methylhidantoin, EGB-761, bimoclomol, sulodexide, Y-128, a hydroxymethyl-glutaryl coenzyme A reductase inhibitor, a fibric acid derivative, a β$_3$-adrenoceptor agonist, an acyl-coenzyme A cholesterol acyltransferase inhibitor, probcol, a thyroid hormone receptor agonist, a cholesterol absorption inhibitor, a lipase inhibitor, a microsomal triglyceride transfer protein inhibitor, a lipoxygenase inhibitor, a carnitine palmitoyl-transferase inhibitor, a squalene synthase inhibitor, a low-density lipoprotein receptor enhancer, a nicotinic acid derivative, a bile acid sequestrant, a sodium/bile acid cotransporter inhibitor, a cholesterol ester transfer protein inhibitor, an appetite suppressant, an angiotensin-converting enzyme inhibitor, a neutral endopeptidase inhibitor, an angiotensin II receptor antagonist, an endothelin-converting enzyme inhibitor, an endothelin receptor antagonist, a diuretic agent, a calcium antagonist, a vasodilating antihypertensive agent, a sympathetic blocking agent, a centrally acting antihypertensive agent, an α$_2$-adrenoceptor agonist, an antiplatelets agent, a uric acid synthesis inhibitor, a uricosuric agent and a urinary alkalinizer, for the manufacture of a pharmaceutical composition for the prevention or treatment of a disease associated with hyperglycemia.

In the present invention, the term "prodrug" means a compound which is converted into a glucopyranosyloxypyrazole derivative represented by the above general formula (II) as an active form thereof in vivo. As examples of groups forming prodrugs, in cases of such groups located at a hydroxy group, a hydroxy-protective group used generally as a prodrug such as a lower acyl group, a lower alkoxy-substituted (lower acyl) group, a lower alkoxycarbonyl-substituted (lower acyl) group, a lower alkoxycarbonyl group and a lower alkoxy-substituted (lower alkoxycarbonyl) group are illustrated, and in cases of such groups located at a nitrogen atom, an aminoprotective group used generally as a prodrug such as a lower acyl group, a lower alkoxycarbonyl group, a lower acyloxymethyl group and a lower alkoxycarbonyloxymethyl group are illustrated.

As the glucopyranosyloxypyrazole derivatives represented by the above general formula (I), for example, compounds represented by the general formula:

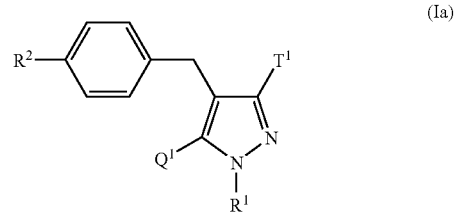

(Ia)

wherein $R^1$ represents a hydrogen atom, a lower alkyl group, a lower acyl group, a lower alkoxycarbonyl group, a lower acyloxymethyl group or a lower alkoxycarbonyloxymethyl group; one of $Q^1$ and $T^1$ represents a group represented by the general formula:

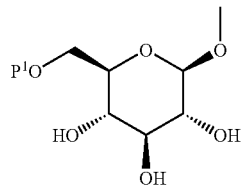

(wherein $P^1$ represents a hydrogen atom, a lower acyl group, a lower alkoxy-substituted (lower acyl) group, a lower alkoxycarbonyl-substituted (lower acyl) group, a lower alkoxycarbonyl group or a lower alkoxy-substituted (lower alkoxycarbonyl) group, while the other represents a lower alkyl group or a halo(lower alkyl) group; $R^2$ represents a hydrogen atom, a lower alkyl group, a lower alkoxy group, a lower alkylthio group, a halo(lower alkyl) group or a halogen atom; and with the proviso that $P^1$ does not represent a hydrogen atom when $R^1$ represents a hydrogen atom or a lower alkyl group, are illustrated.

In the present invention, the term "lower alkyl group" means a straight-chained or branched alkyl group having 1 to 6 carbon atoms such as a methyl group, an ethyl group, a propyl group, an isopropyl group, a butyl group, an isobutyl group, a sec-butyl group, a tert-butyl group, a pentyl group, an isopentyl group, a neopentyl group, a tert-pentyl group, a hexyl group or the like; the term "lower alkoxy group" means a straight-chained or branched alkoxy group having 1 to 6 carbon atoms such as a methoxy group, an ethoxy group, a propoxy group, an isopropoxy group, a butoxy group, an isobutoxy group, a sec-butoxy group, a tert-butoxy group, a pentyloxy group, an isopentyloxy group, a neopentyloxy group, a tert-pentyloxy group, a hexyloxy group or the like; and the term "lower alkylthio group" means a straight-chained or branched alkylthio group having 1 to 6 carbon atoms such as a methylthio group, an ethylthio group, a propylthio group, an isopropylthio group, a butylthio group, an isobutylthio group, a sec-butylthio group, a tert-butylthio group, a pentylthio group, an isopentylthio group, a neopentylthio group, a tert-pentylthio group, a hexylthio group or the like. The term "halogen atom" means a fluorine atom, a chlorine atom, a bromine atom or an iodine atom; and the term "halo(lower alkyl) group" means the above lower alkyl group substituted by different or same 1 to 3 halogen atoms as defined above. The term "lower acyl group" means a straight-chained, branched or cyclic acyl group having 2 to 7 carbon atoms such as an acetyl group, a propionyl group, a butyryl group, an isobutyryl group, a pivaloyl group, a hexanoyl group and a cyclohexylcarbonyl group; and the term "lower alkoxy-substituted (lower acyl) group means the above lower acyl group substituted by the above lower alkoxy group. The term "lower alkoxycarbonyl group" means a straight-chained, branched or cyclic alkoxycarbonyl group having 2 to 7 carbon atoms such as a methoxycarbonyl group, an ethoxycarbonyl group, an isopropyloxycarbonyl group, an isobutyloxycarbonyl group and a cyclohexyloxycarbonyl group; the term "lower alkoxycarbonyl-substituted (lower acyl) group means the above lower acyl group substituted by the above lower alkoxycarbonyl group such as a 3-(ethoxycarbonyl) propionyl group; and the term "lower alkoxy-substituted (lower alkoxycarbonyl) group means the above lower alkoxycarbonyl group substituted by the above alkoxy group such as a 2-methoxyethoxycarbonyl group. Furthermore, the term "lower acyloxymethyl group" means a hydroxymethyl group O-substituted by the above lower acyl group; and the term "lower alkoxycarbonyloxymethyl group" means a hydroxymethyl group O-substituted by the above lower alkoxycarbonyl group.

In the substituent R, a hydrogen atom or a straight-chained or branched alkyl group having 1 to 3 carbon atoms are preferable; a hydrogen atom, an ethyl group, a propyl group or an isopropyl group are more preferable; and an isopropyl group is most preferable because of metabolic stability in human liver S9 fraction. In the substituent $R^2$, a straight-chained or branched alkyl group having 1 to 4 carbon atoms, a straight-chained or branched alkoxy group having 1 to 3 carbon atoms, or a straight-chained or branched alkylthio group having 1 to 3 carbon atoms are preferable; and an ethyl group, an ethoxy group, an isopropoxy group, a methoxy group or a methylthio group are more preferable. In the substituents Q and T, it is preferable that the substituent Q is a lower alkyl group or a halo(lower alkyl) group. Among them, a lower alkyl group is preferable; a straight-chained or branched alkyl group having 1 to 3 carbon atoms is more preferable; and a methyl group is most preferable. In the substituent P, a lower acyl group and a lower alkoxycarbonyl group are preferable; a lower alkoxycarbonyl group is more preferable; and a straight-chained or branched alkoxycarbonyl group having 2 to 5 carbon atoms is most preferable. Concretely, a methoxycarbonyl group, an ethoxycarbonyl group, an isopropoxycarbonyl group or an isobutoxycarbonyl group are preferable.

As the compounds of the present invention, 4-[(4-isopropoxyphenyl)methyl]-1-isopropyl-3-(6-O-methoxycarbonyl-β-D-glucopyranosyloxy)-5-methylpyrazole, 3-(6-O-ethoxycarbonyl-β-D-glucopyranosyloxy)-4-[(4-isopropoxyphenyl)methyl]-1-isopropyl-5-methylpyrazole, 3-(6-O-isopropoxycarbonyl-β-D-glucopyranosyloxy)-4-[(4-isopropoxyphenyl)methyl]-1-isopropyl-5-methylpyrazole, 3-(6-O-isobutoxycarbonyl-β-D-glucopyranosyloxy)-4-[(4-isopropoxyphenyl)methyl]-1-isopropyl-5-methylpyrazole, 4-[(4-ethylphenyl)methyl]-1-isopropyl-3-(6-O-methoxycarbonyl-β-D-glucopyranosyloxy)-5-methylpyrazole, 3-(6-O-ethoxycarbonyl-β-D-glucopyranosyloxy)-4-[(4-ethylphenyl)methyl]-1-isopropyl-5-methylpyrazole, 4-[(4-ethylphenyl)methyl]-3-(6-O-isopropoxycarbonyl-β-D-glucopyranosyloxy)-1-isopropyl-5-methylpyrazole, 4-[(4-ethylphenyl)methyl]-3-(6-O-isobutoxycarbonyl-β-D-glucopyranosyloxy)-1-isopropyl-5-methylpyrazole, 4-[(4-ethoxyphenyl)methyl]-1-isopropyl-3-(6-O-methoxycarbonyl-β-D-glucopyranosyloxy)-5-methylpyrazole, 3-(6-O-ethoxycarbonyl-β-D-glucopyranosyloxy)-4-[(4-ethoxyphenyl)methyl]-1-isopropyl-5-methylpyrazole, 4-[(4-ethoxyphenyl)methyl]-3-(6-O-isopropoxycarbonyl-β-D-glucopyranosyloxy)-1-isopropyl-5-methylpyrazole, 4-[(4-ethoxyphenyl)methyl]-3-(6-O-isobutoxycarbonyl-β-D-glucopyranosyloxy)-1-isopropyl-5-methylpyrazole, 1-isopropyl-3-(6-O-methoxycarbonyl-β-D-glucopyranosyloxy)-4-[(4-methoxyphenyl)methyl]-5-methylpyrazole, 3-(6-O-ethoxycarbonyl-β-D-glucopyranosyloxy)-1-isopropyl-4-[(4-methoxyphenyl)methyl]-5-methylpyrazole, 3-(6-O-isopropoxycarbonyl-β-D-glucopyranosyloxy)-1-isopropyl-4-[(4-methoxyphenyl)methyl]-5-methylpyrazole, 3-(6-O-isobutoxycarbonyl-β-D-glucopyranosyloxy)-1-isopropyl-4-[(4-methoxyphenyl)methyl]-5-methylpyrazole, 1-isopropyl-3-(6-O-methoxycarbonyl-β-D-glucopyranosyloxy)-5-methyl-4-[(4-methylthiophenyl)methyl]pyrazole, 3-(6-O-ethoxycarbonyl-β-D-glucopyranosyloxy)-1-isopropyl-5-methyl-4-[(4-methylthiophenyl)methyl]pyrazole, 3-(6-O-isopropoxycarbonyl-β-D-glucopyranosyloxy)-1-isopropyl-5-methyl-4-[(4-methylthiophenyl)methyl]pyrazole, 3-(6-O-isobutoxycarbonyl-β-D-glucopyranosyloxy)-1-isopropyl-5-methyl-4-[(4-methylthiophenyl)methyl]pyrazole and the like are preferable; 4-[(4-isopropoxyphenyl)methyl]-1-isopropyl-3-(6-O-methoxycarbonyl-β-D-glucopyranosyloxy)-5-methylpyrazole, 3-(6-O-ethoxycarbonyl-β-D-glucopyranosyloxy)-4-[(4-isopropoxyphenyl)methyl]-1-isopropyl-5-methylpyrazole, 3-(6-O-isopropoxycarbonyl-β-D-glucopyranosyloxy)-4-[(4-isopropoxyphenyl)methyl]-1-isopropyl-5-methylpyrazole, 3-(6-O-isobutoxycarbonyl-β-D-glucopyranosyloxy)-4-[(4-isopropoxyphenyl)methyl]-1-isopropyl-5-methylpyrazole and the like are more preferable; and 3-(6-O-ethoxycarbonyl-β-D-glucopyranosyloxy)-4-[(4-isopropoxyphenyl)methyl]-1-isopropyl-5-methylpyrazole and the like are most preferable.

The compounds represented by the above general formula (I) of the present invention can be prepared by introducing hydroxy- and/or amino-protective groups capable of using generally as a prodrug into a hydroxy group and/or a nitrogen atom of a glucopyranosyloxypyrazole derivative represented by the above general formula (II) in usual way.

For example, the compounds of the present invention can be prepared using a glucopyranosyloxypyrazole derivative represented by the above general formula (II) according to the following procedure or analogous procedures thereof:

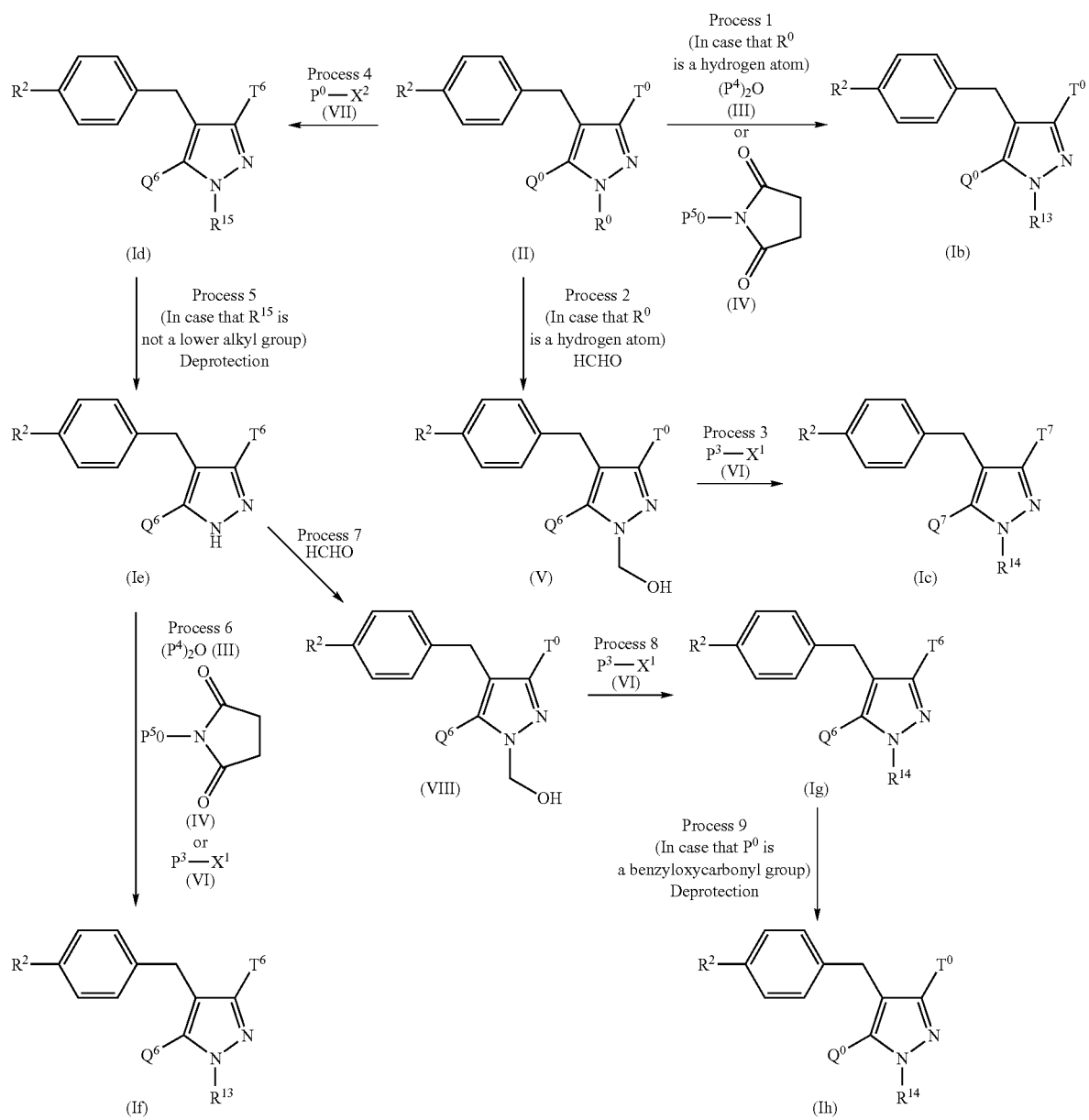

Wherein $P^0$ represents a hydroxy-protective group such as a lower acyl group, a lower alkoxy-substituted (lower acyl) group, a lower alkoxycarbonyl-substituted (lower acyl) group, a lower alkoxycarbonyl group, a lower alkoxy-substituted (lower alkoxycarbonyl) group or a benzyloxycarbonyl group; $P^3$ represents a lower acyl group or a lower alkoxycarbonyl group; $P^4$ represents a lower acyl group; $P^5$ represents a lower alkoxycarbonyl group; $R^{13}$ represents a lower acyl group or a lower alkoxycarbonyl group; $R^{14}$ represents a lower acyloxymethyl group or a lower alkoxycarbonyloxymethyl group; $R^{15}$ represents an amino-protective group such as a lower alkyl group, a lower acyl group, a lower alkoxy-substituted (lower acyl) group, a lower alkoxycarbonyl-substituted (lower acyl) group, a lower alkoxycarbonyl group, a lower alkoxy-substituted (lower alkoxycarbonyl) group or a benzyloxycarbonyl group; one of $Q^6$ and $T^6$ represents a group represented by the general formula:

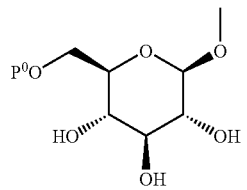

(wherein $P^0$ has the same meaning as defined above), while the other represents a lower alkyl group or a halo(lower alkyl) group; one of $Q^7$ and $T^7$ represents a group represented by the general formula:

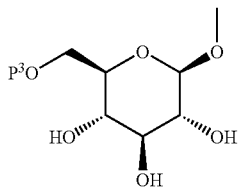

(wherein P³ has the same meaning as defined above), while the other represents a lower alkyl group or a halo(lower alkyl) group; X¹ and X² represent a leaving group such as a bromine atom or a chlorine atom; and R⁰, R², Q⁰ and T⁰ have the same meanings as defined above.

Process 1

A prodrug represented by the above general formula (Ib) can be prepared by protecting the nitrogen atom of a glucopyranosyloxypyrazole derivative represented by the above general formula (II) with an aliphatic acid anhydride represented by the above general formula (III) in an aliphatic acid such as acetic acid at usually 0° C. to reflux temperature for usually 30 minutes to 1 day, or alternatively, by protecting the nitrogen atom of a glucopyranosyloxypyrazole derivative represented by the above general formula (II) with a succinimide derivative represented by the above general formula (IV) in an inert solvent such as tetrahydrofuran at usually room temperature to reflux temperature for usually 1 hour to 1 day. The reaction time can be appropriately varied based on a used starting material, solvent and reaction temperature.

Process 2

A compound represented by the above general formula (V) can be prepared by introducing a hydroxymethyl group into the nitrogen atom of a glucopyranosyloxypyrazole derivative represented by the above general formula (II) using formaldehyde in a various solvent. As the solvent used in the reaction, water, methanol, ethanol, tetrahydrofuran, dichloromethane, ethyl acetate, N,N-dimethylformamide, acetonitrile, a mixed solvent thereof and the like can be illustrated. The reaction temperature is usually from 0° C. to reflux temperature, and the reaction time is usually from 30 minutes to 1 day, varying based on a used starting material, solvent and reaction temperature.

Process 3

A prodrug represented by the above general formula (Ic) can be prepared by protecting the hydroxymethyl group of a compound represented by the above general formula (V) with a reagent for protecting represented by the above general formula (VI) in the presence of a base such as pyridine, triethylamine, N,N-diisopropylethylamine, picoline, lutidine, collidine, quinuclidine, 1,2,2,6,6-pentamethylpiperidine or 1,4-diazabicyclo[2.2.2]octane in an inert solvent or without any solvent. As the inert solvent used in the reaction, dichloromethane, acetonitrile, ethyl acetate, diisopropyl ether, chloroform, tetrahydrofuran, 1,2-dimethoxyethane, 1,4-dioxane, acetone, tert-butanol, a mixed solvent thereof and the like can be illustrated. The reaction temperature is usually from −40° C. to reflux temperature, and the reaction time is usually from 30 minutes to 2 days, varying based on a used starting material, solvent and reaction temperature.

Process 4

A prodrug represented by the above general formula (Id) or an analogous compound thereof can be prepared by protecting the hydroxymethyl group, or the nitrogen atom and the hydroxymethyl group of a glucopyranosyloxypyrazole derivative represented by the above general formula (II) with a reagent for protecting represented by the above general formula (VII) in the presence of a base such as pyridine, triethylamine, N,N-diisopropylethylamine, picoline, lutidine, collidine, quinuclidine, 1,2,2,6,6-pentamethylpiperidine or 1,4-diazabicyclo[2.2.2]octane in an inert solvent or without any solvent. As the inert solvent used in the reaction, dichloromethane, acetonitrile, ethyl acetate, diisopropyl ether, chloroform, tetrahydrofuran, 1,2-dimethoxyethane, 1,4-dioxane, acetone, tert-butanol, a mixed solvent thereof and the like can be illustrated. The reaction temperature is usually from −40° C. to reflux temperature, and the reaction time is usually from 30 minutes to 2 days, varying based on a used starting material, solvent and reaction temperature.

Process 5

A prodrug represented by the above general formula (Ie) or an analogous compound thereof can be prepared by subjecting a compound represented by the above general formula (Id) to deacylation in the presence of a weak base such as sodium hydrogen carbonate, sodium carbonate or potassium carbonate in an alcoholic solvent such as methanol or ethanol. The reaction temperature is usually from 0° C. to reflux temperature, and the reaction time is usually from 15 minutes to 1 day, varying based on a used starting material, solvent and reaction temperature.

Process 6

A prodrug represented by the above general formula (If) or an analogous compound thereof can be prepared by protecting the nitrogen atom of a compound represented by the above general formula (Ie) with an aliphatic acid anhydride represented by the above general formula (III) in an aliphatic acid such as acetic acid at usually 0° C. to reflux temperature for usually 30 minutes to 1 day, alternatively, with a succinimide derivative represented by the above general formula (IV) in an inert solvent such as tetrahydrofuran at usually room temperature to reflux temperature for 1 hour to 1 day, and further alternatively, with a reagent for protecting represented by the above general formula (VI) in the presence of a base such as pyridine, triethylamine, N,N-diisopropylethylamine, picoline, lutidine, collidine, quinuclidine, 1,2,2,6,6-pentamethylpiperidine or 1,4-diazabicyclo[2.2.2]octane in an inert solvent such as dichloromethane, acetonitrile, ethyl acetate, diisopropyl ether, chloroform, tetrahydrofuran, 1,2-dimethoxyethane, 1,4-dioxane, acetone, tert-butanol or a mixed solvent thereof, or without any solvent at usually −40° C. to reflux temperature for 30 minutes to 2 days. The reaction time can be appropriately varied based on a used starting material, solvent and reaction temperature.

Process 7

A compound represented by the above general formula (VIII) can be prepared by introducing a hydroxymethyl group into the nitrogen atom of a compound represented by the above general formula (Ie) using formaldehyde in a various solvent. As the solvent used in the reaction, water, methanol, ethanol, tetrahydrofuran, dichloromethane, ethyl acetate, N,N-dimethylformamide, acetonitrile, a mixed solvent thereof and the like can be illustrated. The reaction temperature is usually from 0° C. to reflux temperature, and the reaction time is usually from 30 minutes to 1 day, varying based on a used starting material, solvent and reaction temperature.

Process 8

A prodrug represented by the above general formula (Ig) or an analogous compound thereof can be prepared by protecting the hydroxymethyl group of a compound represented by the above general formula (VIII) with a reagent for protecting represented by the above general formula (VI) in the presence of a base such as pyridine, triethylamine, N,N-diisopropylethylamine, picoline, lutidine, collidine, quinuclidine, 1,2,2,6,6-pentamethylpiperidine or 1,4-diazabicyclo[2.2.2]octane in an inert solvent or without any solvent. As the inert solvent used in the reaction, dichloromethane, acetonitrile, ethyl acetate, diisopropyl ether, chloroform, tetrahydrofuran, 1,2-dimethoxyethane, 1,4-dioxane, acetone, tert-butanol, a mixed solvent thereof and the like can be illustrated. The reaction temperature is usually from −40° C. to reflux temperature, and the reaction time is usually from 30 minutes to 2 days, varying based on a used starting material, solvent and reaction temperature.

Process 9

A prodrug represented by the above general formula (Ih) can be prepared by subjecting a compound represented by the above general formula (Ig) to deprotection by catalytic hydrogenation in the presence of a palladium catalyst such as palladium carbon in an inert solvent. As the inert solvent used in the reaction, methanol, ethanol, tetrahydrofuran, ethyl acetate, a mixed solvent thereof and the like can be illustrated. The reaction temperature is usually from 0° C. to reflux temperature, and the reaction time is usually from 30 minutes to 1 day, varying based on a used starting material, solvent and reaction temperature.

For example, the compounds represented by the above general formula (II) which are used as starting materials in the aforementioned production process can be prepared according to the following procedure:

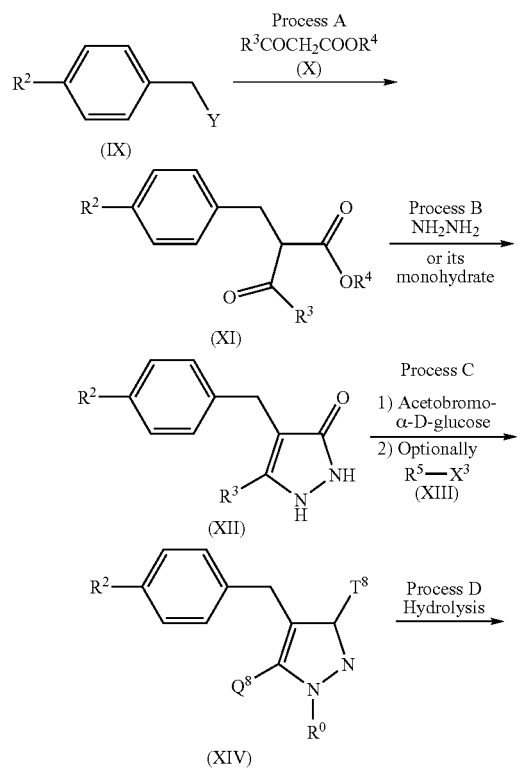

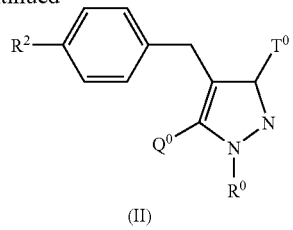

wherein $X^3$ and Y represent a leaving group such as a halogen atom, a mesyloxy group or a tosyloxy group; $R^3$ represents a lower alkyl group or a halo(lower alkyl) group; $R^4$ represents a methyl group or an ethyl group; $R^5$ represents a lower alkyl group; one of $Q^8$ and $T^8$ represents a 2,3,4,6-tatra-O-acetyl-β-D-glucopyranosyloxy group, while the other represents a lower alkyl group or a halo(lower alkyl) group; and $R^0$, $R^2$, $Q^0$ and $T^0$ have the same meanings as defined above.

Process A

A compound represented by the above general formula (XI) can be prepared by condensing a benzyl derivative represented by the above general formula (IX) with a ketoacetate represented by the above general formula (X) in the presence of a base such as sodium hydride or potassium tert-butoxide in an inert solvent. As the inert solvent used in the reaction, 1,2-dimethoxyethane, tetrahydrofuran, N,N-dimethylformamide, a mixed solvent thereof and the like can be illustrated. The reaction temperature is usually from room temperature to reflux temperature, and the reaction time is usually from 1 hour to 1 day, varying based on a used starting material, solvent and reaction temperature.

Process B

A pyrazolone derivative represented by the above general formula (XII) can be prepared by condensing a compound represented by the above general formula (XI) with hydrazine or hydrazine monohydrate in an inert solvent. As the inert solvent used in the reaction, toluene, tetrahydrofuran, chloroform, a mixed solvent thereof and the like can be illustrated. The reaction temperature is usually from room temperature to reflux temperature, and the reaction time is usually from 1 hour to 1 day, varying based on a used starting material, solvent and reaction temperature. The obtained pyrazolone derivative represented by the above general formula (XII) can be also used in process C after converting into a salt thereof in usual way.

Process C

In case of pyrazolone derivatives represented by the above general formula (XII) wherein $R^3$ is a lower alkyl group, a corresponding compound represented by the above general formula (XIV) can be prepared by subjecting a corresponding pyrazolone derivative represented by the above general formula (XII) to glycosidation using acetobromo-α-D-glucose in the presence of a base such as silver carbonate in an inert solvent, and subjecting the resulting compound to N-alkylation using an alkylating agent represented by the above general formula (XIII) in the presence of a base such as potassium carbonate in an inert solvent as occasion demands. As the solvent used in the glycosidation reaction, tetrahydrofuran and the like can be illustrated. The reaction temperature is usually from room temperature to reflux temperature, and the reaction time is usually from 1 hour to 1 day, varying based on a used starting material, solvent and reaction temperature. As the solvent used in the N-alkylation reaction, acetonitrile, N,N-dimethylformamide, tetrohydrofuran, a mixed solvent thereof and the like can be illustrated. The reaction temperature is usually from room temperature to reflux temperature, and the reaction time is usually from 1 hour to 1 day, varying based on a used starting material, solvent and reaction temperature.

In case of pyrazolone derivatives represented by the above general formula (XII) wherein $R^3$ is a halo(lower alkyl) group, a corresponding compound represented by the above general formula (XIV) can be prepared by subjecting a corresponding pyrazolone derivative represented by the above general formula (XII) to glycosidation using acetobromo-α-D-glucose in the presence of a base such as potassium carbonate in an inert solvent, and subjecting the resulting compound to N-alkylation using an alkylating agent represented by the above general formula (XIII) in the presence of a base such as potassium carbonate in an inert solvent as occasion demands. As the solvent used in the glycosidation reaction, acetonitrile, tetrahydrofuran and the like can be illustrated. The reaction temperature is usually from room temperature to reflux temperature, and the reaction time is usually from 1 hour to 1 day, varying based on a used starting material, solvent and reaction temperature. As the solvent used in the N-alkylation reaction, acetonitrile, N,N-dimethylformamide, tetrohydrofuran, a mixed solvent thereof and the like can be illustrated. The reaction temperature is usually from room temperature to reflux temperature, and the reaction time is usually from 1 hour to 1 day, varying based on a used starting material, solvent and reaction temperature.

In the compound represented by the above general formula (XII) as starting materials, there are the following three tautomers, varying based on the change of reaction conditions:

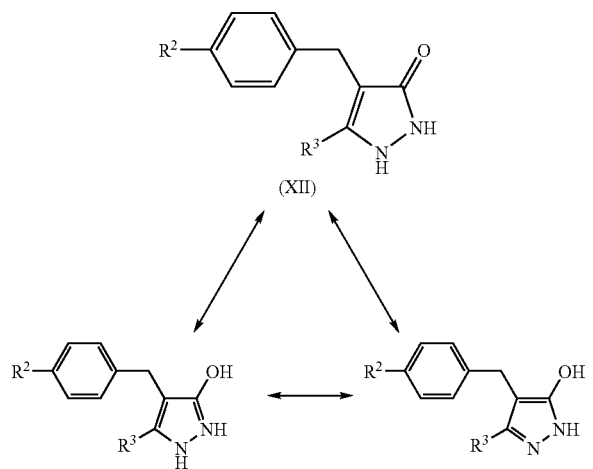

wherein $R^2$ and $R^3$ have the same meanings as defined above.

The obtained compounds represented by the above general formula (XIV) can be also used in process D after converting into a salt thereof in usual way.

Process D

A glucopyranosyloxypyrazole represented by the above general formula (II) can be prepared by subjecting a compound represented by the above general formula (XIV) to hydrolysis. As the solvent used in the reaction, methanol, ethanol, tetrahydrofuran, water, a mixed solvent thereof and the like can be illustrated, and as the base used, sodium hydroxide, sodium ethoxide and the like can be illustrated. The reaction temperature is usually from 0° C. to room temperature, and the reaction time is usually from 30 minutes to 6 hours, varying based on a used starting material, solvent and reaction temperature.

Of the compounds represented by the above general formula (II) which are also used as starting materials in the aforementioned production process, compounds wherein the substituent $R^0$ is a lower alkyl group can be also prepared according to the following procedure:

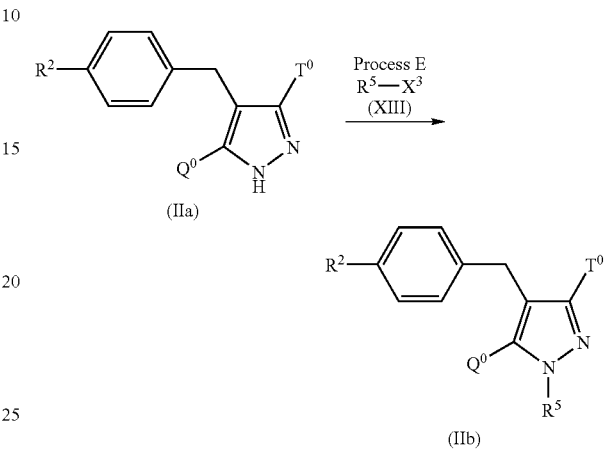

wherein $R^2$, $R^5$, $Q^0$, $T^0$ and $X^3$ have the same meanings as defined above.

Process E

A compound represented by the above general formula (IIb) can be prepared by subjecting a compound represented by the above general formula (IIa) to N-alkylation using an N-alkylating agent represented by the above general formula (XIII) in the presence of a base such as potassium carbonate or cesium carbonate, and occasionally a catalytic amount of sodium iodide in an inert solvent. As the inert solvent used in the reaction, N,N-dimethylformamide, 1,2-dimethoxyethane, dimethyl sulfoxide, tetrahydrofuran, ethanol, a mixed solvent thereof and the like can be illustrated. The reaction temperature is usually from room temperature to reflux temperature, and the reaction time is usually from 10 minutes to 1 day, varying based on a used starting material, solvent and reaction temperature.

The compounds represented by the above general formula (I) of the present invention obtained by the above production processes can be isolated and purified by conventional separation means such as fractional recrystallization, purification using chromatography, solvent extraction and solid phase extraction.

The glucopyranosyloxypyrazole derivatives represented by the above general formula (I) of the present invention can be converted into their pharmaceutically acceptable salts in the usual way. Examples of such salts include acid addition salts with mineral acids such as hydrochloric acid, hydrobromic acid, hydroiodic acid, sulfuric acid, nitric acid, phosphoric acid and the like, acid addition salts with organic acids such as formic acid, acetic acid, methanesulfonic acid, benzenesulfonic acid, p-toluenesulfonic acid, propionic acid, citric acid, succinic acid, tartaric acid, fumaric acid, butyric acid, oxalic acid, malonic acid, maleic acid, lactic acid, malic acid, carbonic acid, glutamic acid, aspartic acid, adipic acid, oleic acid, stearic acid and the like, and salts with inorganic bases such as a sodium salt, a potassium salt, a calcium salt, a magnesium salt and the like.

The prodrugs represented by the above general formula (I) of the present invention include their solvates with pharmaceutically acceptable solvents such as ethanol and water.

Of the compounds represented by the above general formula (I) of the present invention, there are two optical isomers, R-isomer and S-isomer, in each compound having an asymmetric carbon atom excluding the glucopyranosyloxy moiety. In the present invention, either of R-isomer or S-isomer can be employed, and a mixture of both isomers can be also employed.

The prodrugs represented by the above general formula (I) of the present invention are converted into glucopyranosyloxypyrazole derivatives represented by the above general formula (II) as their active forms in vivo, and show an excellent inhibitory activity in human SGLT2. On the other hand, since WAY-123783 has an extremely weak inhibitory activity in human SGLT2, it can not be expected that it exerts an enough effect as a human SGLT2 inhibitor. In addition, the prodrugs represented by the above general formula (I) of the present invention have an improved oral absorption, and pharmaceutical compositions comprising as an active ingredient the prodrug have a highly usefulness as oral formulations. Therefore, the prodrugs of the present invention are extremely useful as agents for the prevention or treatment of a disease associated with hyperglycemia such as diabetes, diabetic complications (e.g., retinopathy, neuropathy, nephropathy, ulcer, macroangiopathy), obesity, hyperinsulinemia, glucose metabolism disorder, hyperlipidemia, hypercholesterolemia, hypertriglyceridemia, lipid metabolism disorder, atherosclerosis, hypertension, congestive heart failure, edema, hyperuricemia, gout or the like.

Furthermore, the compounds of the present invention can be suitably used in combination with at least one member selected from drugs other than SGLT2 inhibitors. Examples of the drugs which can be used in combination with the compounds of the present invention include an insulin sensitivity enhancer, a glucose absorption inhibitor, a biguanide, an insulin secretion enhancer, an insulin preparation, a glucagon receptor antagonist, an insulin receptor kinase stimulant, a tripeptidyl peptidase II inhibitor, a dipeptidyl peptidase IV inhibitor, a protein tyrosine phosphatase-1B inhibitor, a glycogen phosphorylase inhibitor, a glucose-6-phosphatase inhibitor, a fructose-bisphosphatase inhibitor, a pyruvate dehydrogenase inhibitor, a hepatic gluconeogenesis inhibitor, D-chiroinsitol, a glycogen synthase kinase-3 inhibitor, glucagon-like peptide-1, a glucagon-like peptide-1 analogue, a glucagon-like peptide-1 agonist, amylin, an amylin analogue, an amylin agonist, an aldose reductase inhibitor, an advanced glycation endproducts formation inhibitor, a protein kinase C inhibitor, a γ-aminobutyric acid receptor antagonist, a sodium channel antagonist, a transcript factor NF-κB inhibitor, a lipid peroxidase inhibitor, an N-acetylated-α-linked-acid-dipeptidase inhibitor, insulin-like growth factor-I, platelet-derived growth factor (PDGF), a platelet-derived growth factor (PDGF) analogue (e.g., PDGF-AA, PDGF-BB, PDGF-AB), epidermal growth factor (EGF), nerve growth factor, a carnitine derivative, uridine, 5-hydroxy-1-methylhidantoin, EGB-761, bimoclomol, sulodexide, Y-128, a hydroxymethylglutaryl coenzyme A reductase inhibitor, a fibric acid derivative, a $\beta_3$-adrenoceptor agonist, an acyl-coenzyme A cholesterol acyltransferase inhibitor, probcol, a thyroid hormone receptor agonist, a cholesterol absorption inhibitor, a lipase inhibitor, a microsomal triglyceride transfer protein inhibitor, a lipoxygenase inhibitor, a carnitine palmitoyltransferase inhibitor, a squalene synthase inhibitor, a low-density lipoprotein receptor enhancer, a nicotinic acid derivative, a bile acid sequestrant, a sodium/bile acid cotransporter inhibitor, a cholesterol ester transfer protein inhibitor, an appetite suppressant, an angiotensin-converting enzyme inhibitor, a neutral endopeptidase inhibitor, an angiotensin II receptor antagonist, an endothelin-converting enzyme inhibitor, an endothelin receptor antagonist, a diuretic agent, a calcium antagonist, a vasodilating antihypertensive agent, a sympathetic blocking agent, a centrally acting antihypertensive agent, an $\alpha_2$-adrenoceptor agonist, an antiplatelets agent, a uric acid synthesis inhibitor, a uricosuric agent and a urinary alkalinizer.

In case of uses of the compound of the present invention in combination with the above one or more drugs, the present invention includes either dosage forms of simultaneous administration as a single preparation or separated preparations in way of same or different administration route, and administration at different dosage intervals as separated preparations in way of same or different administration route. A pharmaceutical combination comprising the compound of the present invention and the above one or more drugs includes both dosage forms as a single preparation and separated preparations for combination as mentioned above.

The compounds of the present invention can obtain more advantageous effects than additive effects in the prevention or treatment of the above diseases when using suitably in combination with the above drugs. Also, the administration dose can be decreased in comparison with administration of either drug alone, or adverse effects of coadministrated drugs other than SGLT2 inhibitors can be avoided or declined.

Concrete compounds as the above drugs used for combination and preferable diseases to be treated are exemplified as follows. However, the present invention is not limited thereto, and for example, the concrete compounds include their free compounds, and their or other pharmaceutically acceptable salts.

As insulin sensitivity enhancers, peroxisome proliferator-activated receptor-γagonists such as troglitazone, pioglitazone hydrochloride, rosiglitazone maleate, sodium darglitazone, GI-262570, isaglitazone, LG-100641, NC-2100, T-174, DRF-2189, CLX-0921, CS-011, GW-1929, ciglitazone, sodium englitazone and NIP-221, peroxisome proliferator-activated receptor-α agonists such as GW-9578 and BM-170744, peroxisome proliferator-activated receptor-α/γ agonists such as GW-409544, KRP-297, N,N-622, CLX-0940, LR-90, SB-219994, DRF-4158 and DRF-MDX8, retinoid X receptor agonists such as ALRT-268, AGN-4204, MX-6054, AGN-194204, LG-100754 and bexarotene, and other insulin sensitivity enhancers such as reglixane, ONO-5816, MBX-102, CRE-1625, FK-614, CLX-0901, CRE-1633, N,N-2344, BM-13125, BM-501050, HQL-975, CLX-0900, MBX-668, MBX-675, S-15261, GW-544, AZ-242, LY-510929, AR-H049020 and GW-501516 are illustrated. Insulin sensitivity enhancers are used preferably for diabetes, diabetic complications, obesity, hyperinsulinemia, glucose metabolism disorder, hyperlipidemia, hypercholesterolemia, hypertriglyceridemia, lipid metabolism disorder or atherosclerosis, and more preferably for diabetes, hyper-insulinemia or glucose metabolism disorder because of improving the disturbance of insulin signal transduction in peripheral tissues and enhancing glucose uptake into the tissues from the blood, leading to lowering of blood glucose level.

As glucose absorption inhibitors, α-glucosidase inhibitors such as acarbose, voglibose, miglitol, CKD-711, emiglitate, MDL-25,637, camiglibose and MDL-73,945, and α-amylase inhibitors such as AZM-127 are illustrated. Glucose absorption inhibitors are used preferably for diabetes, diabetic complications, obesity, hyperinsulinemia or glucose metabolism disorder, and more preferably for diabetes or glucose metabolism disorder because of inhibiting the gastrointestinal enzymatic digestion of carbohydrates contained in foods, and inhibiting or delaying the absorption of glucose into the body.

As biguanides, phenformin, buformin hydrochloride, metformin hydrochloride or the like are illustrated. Biguanides are used preferably for diabetes, diabetic complications, hyperinsulinemia or glucose metabolism disorder, and more preferably for diabetes, hyperinsulinemia or glucose metabolism disorder because of lowering blood glucose level by inhibitory effects on hepatic gluconeogenesis, accelerating effects on anaerobic glycolysis in tissues or improving effects on insulin resistance in peripheral tissues.

As insulin secretion enhancers, tolbutamide, chlorpropamide, tolazamide, acetohexamide, glyclopyramide, glyburide (glibenclamide), gliclazide, 1-butyl-3-metanilyl-urea, carbutamide, glibornuride, glipizide, gliquidone, glisoxapide, glybuthiazol, glybuzole, glyhexamide, sodium glymidine, glypinamide, phenbutamide, tolcyclamide, glimepiride, nateglinide, mitiglinide calcium hydrate, repaglinide or the like are illustrated. Insulin secretion enhancers are used preferably for diabetes, diabetic complications or glucose metabolism disorder, and more preferably for diabetes or glucose metabolism disorder because of lowering blood glucose level by acting on pancreatic β-cells and enhancing the insulin secretion.

As insulin preparations, human insulin, human insulin analogues, animal-deprived insulin or the like are illustrated. Insulin preparations are used preferably for diabetes, diabetic complications or glucose metabolism disorder, and more preferably for diabetes or glucose metabolism disorder.

As glucagon receptor antagonists, BAY-27-9955, NNC-92-1687 or the like are illustrated; as insulin receptor kinase stimulants, TER-17411, L-783281, KRX-613 or the like are illustrated; as tripeptidyl peptidase II inhibitors, UCL-1397 or the like are illustrated; as dipeptidyl peptidase IV inhibitors, NVP-DPP728A, TSL-225, P-32/98 or the like are illustrated; as protein tyrosine phosphatase 1B inhibitors, PTP-112, OC-86839, PNU-177496 or the like are illustrated; as glycogen phosphorylase inhibitors, N,N-4201, CP-368296 or the like are illustrated; as fructose-bisphosphatase inhibitors, R-132917 or the like are illustrated; as pyruvate dehydrogenase inhibitors, AZD-7545 or the like are illustrated; as hepatic gluconeogenesis inhibitors, FR-225659 or the like are illustrated; as glucagon-like peptide-1 analogues, exendin-4, CJC-1131 or the like are illustrated; as glucagon-like peptide 1 agonists; AZM-134, LY-315902 or the like are illustrated; and as amylin, amylin analogues or amylin agonists, pramlintide acetate or the like are illustrated. These drugs, glucose-6-phosphatase inhibitors, D-chiroinsitol, glycogen synthase kinase-3 inhibitors, glucagon-like peptide-1 are used preferably for diabetes, diabetic complications, hyperinsulinemia or glucose metabolism disorder, and more preferably for diabetes or glucose metabolism disorder.

As aldose reductase inhibitors, ascorbyl gamolenate, tolrestat, epalrestat, ADN-138, BAL-ARI8, ZD-5522, ADN-311, GP-1447, IDD-598, fidarestat, sorbinil, ponalrestat, risarestat, zenarestat, minalrestat, methosorbinil, AL-1567, imirestat, M-16209, TAT, AD-5467, zopolrestat, AS-3201, NZ-314, SG-210, JTT-811, lindolrestat or the like are illustrated. Aldose reductase inhibitors are preferably used for diabetic complications because of inhibiting aldose reductase and lowering excessive intracellular accumulation of sorbitol in accelated polyol pathway which are in continuous hyperglycemic condition in the tissues in diabetic complications.

As advanced glycation endproducts formation inhibitors, pyridoxamine, OPB-9195, ALT-946, ALT-711, pimagedine hydrochloride or the like are illustrated. Advanced glycation endproducts formation inhibitors are preferably used for diabetic complications because of inhibiting formation of advanced glycation endproducts which are accelated in continuous hyperglycemic condition in diabetes and declining of cellular damage.

As protein kinase C inhibitors, LY-333531, midostaurin or the like are illustrated. Protein kinase C inhibitors are preferably used for diabetic complications because of inhibiting of protein kinase C activity which is accelated in continuous hyperglycemic condition in diabetes.

As γ-aminobutyric acid receptor antagonists, topiramate or the like are illustrated; as sodium channel antagonists, mexiletine hydrochloride, oxcarbazepine or the like are illustrated; as transcrit factor NF-κB inhibitors, dexlipotam or the like are illustrated; as lipid peroxidase inhibitors, tirilazad mesylate or the like are illustrated; as N-acetylated-α-linked-acid-dipeptidase inhibitors, GPI-5693 or the like are illustrated; and as carnitine derivatives, carnitine, levacecamine hydrochloride, levocarnitine chloride, levocarnitine, ST-261 or the like are illustrated. These drugs, insulin-like growth factor-I, platelet-derived growth factor, platelet derived growth factor analogues, epidermal growth factor, nerve growth factor, uridine, 5-hydroxy-1-methylhidantoin, EGB-761, bimoclomol, sulodexide and Y-128 are preferably used for diabetic complications.

As hydroxymethylglutaryl coenzyme A reductase inhibitors, sodium cerivastatin, sodium pravastatin, lovastatin, simvastatin, sodium fluvastatin, atorvastatin calcium hydrate, SC-45355, SQ-33600, CP-83101, BB-476, L-669262, S-2468, DMP-565, U-20685, BAY-x-2678, BAY-10-2987, calcium pitavastatin, calcium rosuvastatin, colestolone, dalvastatin, acitemate, mevastatin, crilvastatin, BMS-180431, BMY-21950, glenvastatin, carvastatin, BMY-22089, bervastatin or the like are illustrated. Hydroxymethylglutaryl coenzyme A reductase inhibitors are used preferably for hyperlipidemia, hypercholesterolemia, hypertriglyceridemia, lipid metabolism disorder or atherosclerosis, and more preferably for hyperlipidemia, hypercholesterolemia or atherosclerosis because of lowering blood cholesterol level by inhibiting hydroxymethylglutaryl coenzyme A reductase.

As fibric acid derivatives, bezafibrate, beclobrate, binifibrate, ciprofibrate, clinofibrate, clofibrate, aluminum clofibrate, clofibric acid, etofibrate, fenofibrate, gemfibrozil, nicofibrate, pirifibrate, ronifibrate, simfibrate, theofibrate, AHL-157 or the like are illustrated. Fibric acid derivatives are used preferably for hyper-insulinemia, hyperlipidemia, hypercholesterolemia, hypertriglyceridemia, lipid metabolism disorder or atherosclerosis, and more preferably for hyperlipidemia, hypertriglyceridemia or atherosclerosis because of activating hepatic lipoprotein lipase and enhancing fatty acid oxidation, leading to lowering of blood triglyceride level.

As $β_3$-adrenoceptor agonists, BRL-28410, SR-58611A, ICI-198157, ZD-2079, BMS-194449, BRL-37344, CP-331679, CP-114271, L-750355, BMS-187413, SR-59062A, BMS-210285, LY-377604, SWR-0342SA, AZ-40140, SB-226552, D-7114, BRL-35135, FR-149175, BRL-26830A, CL-316243, AJ-9677, GW-427353, N-5984, GW-2696 or the like are illustrated. $β_3$-Adrenoceptor agonists are used preferably for obesity, hyperinsulinemia, hyperlipidemia, hypercholesterolemia, hypertriglyceridemia or lipid metabolism disorder, and more preferably for obesity or hyperinsulinemia because of stimulating $β_3$-adrenoceptor in adipose tissue and enhancing the fatty acid oxidation, leading to induction of energy expenditure.

As acyl-coenzyme A cholesterol acyltransferase inhibitors, NTE-122, MCC-147, PD-132301-2, DUP-129, U-73482, U-76807, RP-70676, P-06139, CP-113818, RP-73163, FR-129169, FY-038, EAB-309, KY-455, LS-3115, FR-145237, T-2591, J-104127, R-755, FCE-28654, YIC-C8-434, avasimibe, CI-976, RP-64477, F-1394, eldacimibe, CS-505, CL-283546, YM-17E, lecimibide, 447C88, YM-750, E-5324, KW-3033, HL-004, eflucimibe or the like are illustrated. Acyl-coenzyme A cholesterol acyltransferase inhibitors are used preferably for hyperlipidemia, hypercholesterolemia, hypertriglyceridemia or lipid metabolism disorder, and more preferably for hyperlipidemia or hypercholesterolemia because of lowering blood cholesterol level by inhibiting acyl-coenzyme A cholesterol acyltransferase.

As thyroid hormone receptor agonists, sodium liothyronine, sodium levothyroxine, KB-2611 or the like are illustrated; as cholesterol absorption inhibitors, ezetimibe, SCH-48461 or the like are illustrated; as lipase inhibitors, orlistat, ATL-962, AZM-131, RED-103004 or the like are illustrated; as carnitine palmitoyltransferase inhibitors, etomoxir or the like are illustrated; as squalene synthase inhibitors, SDZ-268-198, BMS-188494, A-87049, RPR-101821, ZD-9720, RPR-107393, ER-27856 or the like are illustrated; as nicotinic acid derivatives, nicotinic acid, nicotinamide, nicomol, niceritrol, acipimox, nicorandil or the like are illustrated; as bile acid sequestrants, colestyramine, colestilan, colesevelam hydrochloride, GT-102-279 or the like are illustrated; as sodium/bile acid cotransporter inhibitors, 264W94, S-8921, SD-5613 or the like are illustrated; and as cholesterol ester transfer protein inhibitors, PNU-107368E, SC-795, JTT-705, CP-529414 or the like are illustrated. These drugs, probcol, microsomal triglyceride transfer protein inhibitors, lipoxygenase inhibitors and low-density lipoprotein receptor enhancers are preferably used for hyperlipidemia, hypercholesterolemia, hypertriglyceridemia or lipid metabolism disorder.

As appetite suppressants, monoamine reuptake inhibitors, serotonin reuptake inhibitors, serotonin releasing stimulants, serotonin agonists (especially $5HT_{2C}$-agonists), noradrenaline reuptake inhibitors, noradrenaline releasing stimulants, $\alpha_1$-adrenoceptor agonists, $\beta_2$-adrenoceptor agonists, dopamine agonists, cannabinoid receptor antagonists, $\gamma$-aminobutyric acid receptor antagonists, $H_3$-histamine antagonists, L-histidine, leptin, leptin analogues, leptin receptor agonists, melanocortin receptor agonists (especially, MC3-R agonists, MC4-R agonists), $\alpha$-melanocyte stimulating hormone, cocaine- and amphetamine-regulated transcript, mahogany protein, enterostatin agonists, calcitonin, calcitonin-gene-related peptide, bombesin, cholecystokinin agonists (especially CCK-A agonists), corticotropin-releasing hormone, corticotrophin-releasing hormone analogues, corticotropin-releasing hormone agonists, urocortin, somatostatin, somatostatin analogues, somatostatin receptor agonists, pituitary adenylate cyclase-activating peptide, brain-derived neurotrophic factor, ciliary neurotrophic factor, thyrotropin-releasing hormone, neurotensin, sauvagine, neuropeptide Y antagonists, opioid peptide antagonists, galanin antagonists, melanin-concentrating hormone antagonists, agouti-related protein inhibitors and orexin receptor antagonists are illustrated. Concretely, as monoamine reuptake inhibitors, mazindol or the like are illustrated; as serotonin reuptake inhibitors, dexfenfluramine hydrochloride, fenfluramine, sibutramine hydrochloride, fluvoxamine maleate, sertraline hydrochloride or the like are illustrated; as serotonin agonists, inotriptan, (+)-norfenfluramine or the like are illustrated; as noradrenaline reuptake inhibitors, bupropion, GW-320659 or the like are illustrated; as noradrenaline releasing stimulants, rolipram, YM-992 or the like are illustrated; as $\beta_2$-adrenoceptor agonists, amphetamine, dextroamphetamine, phentermine, benzphetamine, methamphetamine, phendimetrazine, phenmetrazine, diethylpropion, phenylpropanolamine, clobenzorex or the like are illustrated; as dopamine agonists, ER-230, doprexin, bromocriptine mesylate or the like are illustrated; as cannabinoid receptor antagonists, rimonabant or the like are illustrated; as $\gamma$-aminobutyric acid receptor antagonists, topiramate or the like are illustrated; as $H_3$-histamine antagonists, GT-2394 or the like are illustrated; as leptin, leptin analogues or leptin receptor agonists, LY-355101 or the like are illustrated; as cholecystokinin agonists (especially CCK-A agonists), SR-146131, SSR-125180, BP-3.200, A-71623, FPL-15849, GI-248573, GW-7178, GI-181771, GW-7854, A-71378 or the like are illustrated; and as neuropeptide Y antagonists, SR-120819-A, PD-160170, NGD-95-1, BIBP-3226, 1229-U-91, CGP-71683, BIBO-3304, CP-671906-01, J-115814 or the like are illustrated. Appetite suppressants are used preferably for diabetes, diabetic complications, obesity, glucose metabolism disorder, hyperlipidemia, hypercholesterolemia, hypertriglyceridemia, lipid metabolism disorder, atherosclerosis, hypertension, congestive heart failure, edema, hyperuricemia or gout, and more preferably for obesity because of stimulating or inhibiting the activities of intracerebral monoamines or bioactive peptides in central appetite regulatory system and suppressing the appetite, leading to reduction of energy intake.

As angiotensin-converting enzyme inhibitors, captopril, enalapri maleate, alacepril, delapril hydrochloride, ramipril, lisinopril, imidapril hydrochloride, benazepril hydrochloride, ceronapril monohydrate, cilazapril, sodium fosinopril, perindopril erbumine, calcium moveltipril, quinapril hydrochloride, spirapril hydrochloride, temocapril hydrochloride, trandolapril, calcium zofenopril, moexipril hydrochloride, rentiapril or the like are illustrated. Angiotensin-converting enzyme inhibitors are preferably used for diabetic complications or hypertension.

As neutral endopeptidase inhibitors, omapatrilat, MDL-100240, fasidotril, sampatrilat, GW-660511X, mixanpril, SA-7060, E-4030, SLV-306, ecadotril or the like are illustrated. Neutral endopeptidase inhibitors are preferably used for diabetic complications or hypertension.

As angiotensin II receptor antagonists, candesartan cilexetil, candesartan cilexetil/hydrochlorothiazide, potassium losartan, eprosartan mesylate, valsartan, telmisartan, irbesartan, EXP-3174, L-158809, EXP-3312, olmesartan, tasosartan, KT-3-671, GA-0113, RU-64276, EMD-90423, BR-9701 or the like are illustrated. Angiotensin II receptor antagonists are preferably used for diabetic complications or hypertension.

As endothelin-converting enzyme inhibitors, CGS-31447, CGS-35066, SM-19712 or the like are illustrated; as endothelin receptor antagonists, L-749805, TBC-3214, BMS-182874, BQ-610, TA-0201, SB-215355, PD-180988, sodium sitaxsentan, BMS-193884, darusentan, TBC-3711, bosentan, sodium tezosentan, J-104132, YM-598, S-0139, SB-234551, RPR-118031A, ATZ-1993, RO-61-1790, ABT-546, enlasentan, BMS-207940 or the like are illustrated. These drugs are preferably used for diabetic complications or hypertension, and more preferably for hypertension.

As diuretic agents, chlorthalidone, metolazone, cyclopenthiazide, trichloromethiazide, hydrochlorothiazide, hydroflumethiazide, benzylhydrochlorothiazide, penflutizide, methyclothiazide, indapamide, tripamide, mefruside, azosemide, etacrynic acid, torasemide, piretanide, furosemide, bumetanide, meticrane, potassium canrenoate, spironolactone, triamterene, aminophylline, cicletanine hydrochloride, LLU-$\alpha$, PNU-80873A, isosorbide, D-mannitol, D-sorbitol, fructose, glycerin, acetazolamide, methazolamide, FR-179544, OPC-31260, lixivaptan, conivaptan hydrochloride or the like are illustrated. Diuretic drugs are preferably used for diabetic complications, hypertension, congestive heart failure or edema, and more preferably for hypertension, congestive heart failure or edema because of reducing blood pressure or improving edema by increasing urinary excretion.

As calcium antagonists, aranidipine, efonidipine hydrochloride, nicardipine hydrochloride, barnidipine hydrochloride, benidipine hydrochloride, manidipine hydrochloride, cilnidipine, nisoldipine, nitrendipine, nifedipine, nilvadipine, felodipine, amlodipine besilate, pranidipine, lercanidipine hydrochloride, isradipine, elgodipine, azelnidipine, lacidipine, vatanidipine hydrochloride, lemildipine, diltiazem hydrochloride, clentiazem maleate, verapamil hydrochloride, S-verapamil, fasudil hydrochloride, bepridil hydrochloride, gallopamil hydrochloride or the like are illustrated; as vasodilating antihypertensive agents, indapamide, todralazine hydrochloride, hydralazine hydrochloride, cadralazine, budralazine or the like are illustrated; as sympathetic blocking agents, amosulalol hydrochloride, terazosin hydrochloride, bunazosin hydrochloride, prazosin hydrochloride, doxazosin mesylate, propranolol hydrochloride, atenolol, metoprolol tartrate, carvedilol, nipradilol, celiprolol hydrochloride, nebivolol, betaxolol hydrochloride, pindolol, tertatolol hydrochloride, bevantolol hydrochloride, timolol maleate, carteolol hydrochloride, bisoprolol hemifumarate, bopindolol malonate, nipradilol, penbutolol sulfate, acebutolol hydrochloride, tilisolol hydrochloride, nadolol, urapidil, indoramin or the like are illustrated; as centrally acting antihypertensive agents, reserpine or the like are illustrated; and as $\alpha_2$-adrenoceptor agonists, clonidine hydrochloride, methyldopa, CHF-1035, guanabenz acetate, guanfacine hydrochloride, moxonidine, lofexidine, talipexole hydrochloride or the like are illustrated. These drugs are preferably used for hypertension.

As antiplatelets agents, ticlopidine hydrochloride, dipyridamole, cilostazol, ethyl icosapentate, sarpogrelate hydrochloride, dilazep dihydrochloride, trapidil, beraprost sodium, aspirin or the like are illustrated. Antiplatelets agents are preferably used for atherosclerosis or congestive heart failure.

As uric acid synthesis inhibitors, allopurinol, oxypurinol or the like are illustrated; as uricosuric agents, benzbromarone, probenecid or the like are illustrated; and as urinary alkalinizers, sodium hydrogen carbonate, potassium citrate, sodium citrate or the like are illustrated. These drugs are preferably used for hyperuricemia or gout.

In case of use in combination with drugs other than SGLT2 inhibitors, for example, in the use for diabetes, the combination with at least one member of the group consisting of an insulin sensitivity enhancer, a glucose absorption inhibitor, a biguanide, an insulin secretion enhancer, an insulin preparation, a glucagon receptor antagonist, an insulin receptor kinase stimulant, a tripeptidyl peptidase II inhibitor, a dipeptidyl peptidase IV inhibitor, a protein tyrosine phosphatase-1B inhibitor, a glycogen phosphorylase inhibitor, a glucose-6-phosphatase inhibitor, a fructose-bisphosphatase inhibitor, a pyruvate dehydrogenase inhibitor, a hepatic gluconeogenesis inhibitor, D-chiroinsitol, a glycogen synthase kinase-3 inhibitor, glucagon-like peptide-1, a glucagon-like peptide-1 analogue, a glucagon-like peptide-1 agonist, amylin, an amylin analogue, an amylin agonist and an appetite suppressant is preferable; the combination with at least one member of the group consisting of an insulin sensitivity enhancer, a glucose absorption inhibitor, a biguanide, an insulin secretion enhancer, an insulin preparation, a glucagon receptor antagonist, an insulin receptor kinase stimulant, a tripeptidyl peptidase II inhibitor, a dipeptidyl peptidase IV inhibitor, a protein tyrosine phosphatase-1B inhibitor, a glycogen phosphorylase inhibitor, a glucose-6-phosphatase inhibitor, a fructose-bisphosphatase inhibitor, a pyruvate dehydrogenase inhibitor, a hepatic gluconeogenesis inhibitor, D-chiroinsitol, a glycogen synthase kinase-3 inhibitor, glucagon-like peptide-1, a glucagon-like peptide-1 analogue, a glucagon-like peptide-1 agonist, amylin, an amylin analogue and an amylin agonist is more preferable; and the combination with at least one member of the group consisting of an insulin sensitivity enhancer, a glucose absorption inhibitor, a biguanide, an insulin secretion enhancer and an insulin preparation is most preferable. Similarly, in the use for diabetic complications, the combination with at least one member of the group consisting of an insulin sensitivity enhancer, a glucose absorption inhibitor, a biguanide, an insulin secretion enhancer, an insulin preparation, a glucagon receptor antagonist, an insulin receptor kinase stimulant, a tripeptidyl peptidase II inhibitor, a dipeptidyl peptidase IV inhibitor, a protein tyrosine phosphatase-1B inhibitor, a glycogen phosphorylase inhibitor, a glucose-6-phosphatase inhibitor, a fructose-bisphosphatase inhibitor, a pyruvate dehydrogenase inhibitor, a hepatic gluconeogenesis inhibitor, D-chiroinsitol, glycogen synthase kinase-3 inhibitors, glucagon-like peptide-1, a glucagon-like peptide-1 analogue, a glucagon-like peptide-1 agonist, amylin, an amylin analogue, an amylin agonist, an aldose reductase inhibitor, an advanced glycation endproducts formation inhibitor, a protein kinase C inhibitor, a γ-aminobutyric acid antagonist, a sodium channel antagonist, a transcript factor NF-κB inhibitor, a lipid peroxidase inhibitor, an N-acetylated-α-linked-acid-dipeptidase inhibitor, insulin-like growth factor-I, platelet-derived growth factor, a platelet derived growth factor analogue, epidermal growth factor, nerve growth factor, a carnitine derivative, uridine, 5-hydroxy-1-methylhidantoin, EGB-761, bimoclomol, sulodexide, Y-128, an angiotensin-converting enzyme inhibitor, a neutral endopeptidase inhibitor, an angiotensin II receptor antagonist, an endothelin-converting enzyme inhibitor, an endothelin receptor antagonist and a diuretic agent is preferable; and the combination with at least one member of the group consisting of an aldose reductase inhibitor, an angiotensin-converting enzyme inhibitor, a neutral endopeptidase inhibitor and an angiotensin II receptor antagonist is more preferable. Furthermore, in the use for obesity, the combination with at least one member of the group consisting of an insulin sensitivity enhancer, a glucose absorption inhibitor, a biguanide, an insulin secretion enhancer, an insulin preparation, a glucagon receptor antagonist, an insulin receptor kinase stimulant, a tripeptidyl peptidase II inhibitor, a dipeptidyl peptidase IV inhibitor, a protein tyrosine phosphatase-1B inhibitor, a glycogen phosphorylase inhibitor, a glucose-6-phosphatase inhibitor, a fructose-bisphosphatase inhibitor, a pyruvate dehydrogenase inhibitor, a hepatic gluconeogenesis inhibitor, D-chiroinsitol, a glycogen synthase kinase-3 inhibitor, glucagon-like peptide-1, a glucagon-like peptide-1 analogue, a glucagon-like peptide-1 agonist, amylin, an amylin analogue, an amylin agonist, a $\beta_3$-adrenoceptor agonist and an appetite suppressant is preferable; and the combination with at least one member of the group consisting of a $\beta_3$-adrenoceptor agonist and an appetite suppressant is more preferable.

When the pharmaceutical compositions of the present invention are employed in the practical treatment, various dosage forms are used depending on their uses. As examples of the dosage forms, powders, granules, fine granules, dry sirups, tablets, capsules, injections, solutions, ointments, suppositories, poultices and the like are illustrated, which are orally or parenterally administered.

These pharmaceutical compositions can be prepared by admixing with or by diluting and dissolving an appropriate pharmaceutical additive such as excipients, disintegrators, binders, lubricants, diluents, buffers, isotonicities, antiseptics, moistening agents, emulsifiers, dispersing agents, stabilizing agents, dissolving aids and the like, and formulating the mixture in accordance with conventional. In case of the use of the compound of the present invention in combination with the drugs other than SGLT2 inhibitors, they can be prepared by formulating each active ingredient together or individually.

When the pharmaceutical compositions of the present invention are employed in the practical treatment, the dosage of a compound represented by the above general formula (I) or a pharmaceutically acceptable salt thereof as the active ingredient is appropriately decided depending on the age, sex, body weight and degree of symptoms and treatment of each patient, which is approximately within the range of from 0.1 to 1,000 mg per day per adult human in the case of oral administration and approximately within the range of from 0.01 to 300 mg per day per adult human in the case of parenteral administration, and the daily dose can be divided into one to several doses per day and administered suitably. Also, in case of the use of the compound of the present invention in combination with the drugs other than SGLT2 inhibitors, the dosage of the compound of the present invention can be decreased appropriately and occasionally depending on the dosage of the drugs other than SGLT2 inhibitors.

The present invention is further illustrated in more detail by way of the following Reference Examples, Examples and Test Examples. However, the present invention is not limited thereto.

REFERENCE EXAMPLE 1

1,2-Dihydro-4-[(4-isopropoxyphenyl)methyl]-5-methyl-3H-pyrazol-3-one

To a solution of 4-isopropoxybenzylalcohol (0.34 g) in tetrahydrofuran (6 mL) were added triethylamine (0.28 mL) and methanesulfonyl chloride (0.16 mL), and the mixture was stirred at room temperature for 30 minutes. The resulting insoluble material was removed by filtration. The obtained solution of 4-isopropoxybenzyl methanesulfonate in tetrahydrofuran was added to a suspension of sodium hydride (60%, 81 mg) and methyl acetoacetate (0.20 mL) in 1,2-dimethoxyethane (10 mL), and the mixture was stirred at 80° C. overnight. The reaction mixture was poured into a saturated aqueous sodium hydrogen carbonate solution, and the resulting mixture was extracted with diethyl ether. The organic layer was washed with brine and dried over anhydrous magnesium sulfate. The solvent was removed under reduced pressure, and the residue was dissolved in toluene (5 mL). Anhydrous hydrazine (0.19 mL) was added to the solution, and the mixture was stirred at 80° C. overnight. The solvent was removed under reduced pressure, and the residue was purified by column chromatography on silica gel (eluent: dichloromethane/methanol=10/1) to give 1,2-dihydro-4-[(4-isopropoxyphenyl)methyl]-5-methyl-3H-pyrazol-3-one (95 mg).

$^1$H-NMR (DMSO-$d_6$) δ ppm:
1.22 (6H, d, J=6.0 Hz), 1.99 (3H, s), 3.45 (2H, s), 4.40-4.60 (1H, m), 6.65-6.80 (2H, m), 6.95-7.10 (2H, m)

REFERENCE EXAMPLE 2

1,2-Dihydro-5-methyl-4-[(4-propylphenyl)methyl]-3H-pyrazol-3-one

The title compound was prepared in a similar manner to that described in Reference Example 1 using 4-propylbenzyl alcohol instead of 4-isopropoxybenzyl alcohol.

$^1$H-NMR (DMSO-$d_6$) δ ppm:
0.75-0.95 (3H, m), 1.45-1.65 (2H, m), 1.99 (3H, s), 2.40-2.55 (2H, m), 3.32 (2H, s), 6.95-7.10 (4H, m)

REFERENCE EXAMPLE 3

1,2-Dihydro-4-[(4-isobutylphenyl)methyl]-5-methyl-3H-pyrazol-3-one

The title compound was prepared in a similar manner to that described in Reference Example 1 using 4-isobutylbenzyl alcohol instead of 4-isopropoxybenzyl alcohol.

$^1$H-NMR (DMSO-$d_6$) δ ppm:
0.83 (6H, d, J=6.6 Hz), 1.70-1.85 (1H, m), 1.99 (3H, s), 2.30-2.45 (2H, m), 3.50 (2H, s), 6.90-7.10 (4H, m)

REFERENCE EXAMPLE 4

1,2-Dihydro-5-methyl-4-[(4-propoxyphenyl)methyl]-3H-pyrazol-3-one

The title compound was prepared in a similar manner to that described in Reference Example 1 using 4-propoxybenzyl alcohol instead of 4-isopropoxybenzyl alcohol.

$^1$H-NMR (DMSO-$d_6$) δ ppm:
0.95 (3H, t, J=7.4 Hz), 1.60-1.75 (2H, m), 1.98 (3H, s), 3.46 (2H, s), 3.75-3.90 (2H, m), 6.70-6.85 (2H, m), 6.95-7.10 (2H, m)

REFERENCE EXAMPLE 5

4-[(4-Ethoxyphenyl)methyl]-1,2-dihydro-5-methyl-3H-pyrazol-3-one

The title compound was prepared in a similar manner to that described in Reference Example 1 using 4-ethoxybenzyl alcohol instead of 4-isopropoxybenzyl alcohol.

1H-NMR (DMSO-d6) δ ppm:
1.20-1.35 (3H, m), 1.98 (3H, s), 3.46 (2H, s), 3.85-4.05 (2H, m), 6.70-6.85 (2H, m), 6.95-7.10 (2H, m)

REFERENCE EXAMPLE 6

1,2-Dihydro-5-methyl-4-[(4-trifluoromethylphenyl)methyl]-3H-pyrazol-3-one

The title compound was prepared in a similar manner to that described in Reference Example 1 using 4-trifluoromethylbenzyl alcohol instead of 4-isopropoxybenzyl alcohol.

1H-NMR (DMSO-d6) δ ppm:
2.02 (3H, s), 3.64 (2H, s), 7.30-7.45 (2H, m), 7.55-7.70 (2H, m)

REFERENCE EXAMPLE 7

4-[(4-tert-Butylphenyl)methyl]-1,2-dihydro-5-methyl-3H-pyrazol-3-one

The title compound was prepared in a similar manner to that described in Reference Example 1 using 4-tert-butylbenzyl alcohol instead of 4-isopropoxybenzyl alcohol.

$^1$H-NMR (DMSO-$d_6$) δ ppm:
1.24 (9H, s), 2.01 (3H, s), 3.49 (2H, s), 7.00-7.15 (2H, m), 7.15-7.30 (2H, m)

REFERENCE EXAMPLE 8

4-[(4-Butoxyphenyl)methyl]-1,2-dihydro-5-methyl-3H-pyrazol-3-one

The title compound was prepared in a similar manner to that described in Reference Example 1 using 4-butoxybenzyl alcohol instead of 4-isopropoxybenzyl alcohol.

$^1$H-NMR (DMSO-$d_6$) δ ppm:
0.91 (3H, t, J=7.4 Hz), 1.30-1.50 (2H, m), 1.55-1.75 (2H, m), 1.98 (3H, s), 3.46 (2H, s), 3.80-3.95 (2H, m), 6.70-6.85 (2H, m), 6.95-7.10 (2H, m)

REFERENCE EXAMPLE 9

1,2-Dihydro-5-methyl-4-[(4-methylthiophenyl)methyl]-3H-pyrazol-3-one

The title compound was prepared in a similar manner to that described in Reference Example 1 using 4-(methylthio)benzyl alcohol instead of 4-isopropoxybenzyl alcohol.
$^1$H-NMR (DMSO-$d_6$) δ ppm:
1.99 (3H, s), 2.42 (3H, s), 3.50 (2H, s), 7.05-7.20 (4H, m)

REFERENCE EXAMPLE 10

5-Ethyl-1,2-dihydro-4-[(4-methylthiophenyl)methyl]-3H-pyrazol-3-one

The title compound was prepared in a similar manner to that described in Reference Example 1 using 4-(methylthio)benzyl alcohol instead of 4-isopropoxybenzyl alcohol and using methyl 3-oxopentanoate instead of methyl acetoacetate.
$^1$H-NMR (DMSO-$d_6$) δ ppm:
1.02 (3H, t, J=7.6 Hz), 2.39 (2H, q, J=7.6 Hz), 2.42 (3H, s), 3.51 (2H, s), 7.05-7.20 (4H, m)

REFERENCE EXAMPLE 11

1,2-Dihydro-4-[(4-isopropylphenyl)methyl]-5-methyl-3H-pyrazol-3-one

To a suspension of sodium hydride (60%, 40 mg) in 1,2-dimethoxyethane (1 mL) were added methyl acetoacetate (0.11 mL), 4-isopropylbenzyl chloride (0.17 g) and a catalytic amount of sodium iodide, and the mixture was stirred at 80° C. overnight. The reaction mixture was poured into a saturated aqueous sodium hydrogen carbonate solution, and the mixture was extracted with diethyl ether. The organic layer was washed with brine and dried over anhydrous magnesium sulfate. The solvent was removed under reduced pressure, and the residue was dissolved in toluene (1 mL). Anhydrous hydrazine (0.094 mL) was added to the solution, and the mixture was stirred at 80° C. overnight. The solvent was removed under reduced pressure, and the residue was purified by column chromatography on silica gel (eluent: dichloromethane/methanol=10/1) to give 1,2-dihydro-4-[(4-isopropylphenyl)methyl]-5-methyl-3H-pyrazol-3-one (0.12 g).
$^1$H-NMR (DMSO-$d_6$) δ ppm:
1.16 (6H, d, J=6.9 Hz), 2.01 (3H, s), 2.70-2.90 (1H, m), 3.49 (2H, s), 6.95-7.20 (4H, m)

REFERENCE EXAMPLE 12

4-[(4-Ethylphenyl)methyl]-1,2-dihydro-5-methyl-3H-pyrazol-3-one

The title compound was prepared in a similar manner to that described in Reference Example 11 using 4-ethylbenzyl chloride instead of 4-isopropylbenzyl chloride.
$^1$H-NMR (DMSO-$d_6$) δ ppm:
1.13 (3H, t, J=7.6 Hz), 2.00 (3H, s), 2.45-2.60 (2H, m) 3.49 (2H, s), 7.00-7.15 (4H, m)

REFERENCE EXAMPLE 13

1,2-Dihydro-5-methyl-4-[(4-methylphenyl)methyl]-3H-pyrazol-3-one

The title compound was prepared in a similar manner to that described in Reference Example 11 using 4-methylbenzyl bromide instead of 4-isopropylbenzyl chloride.
$^1$H-NMR (DMSO-$d_6$) δ ppm:
1.98 (3H, s), 2.23 (3H, s), 3.48 (2H, s), 6.95-7.10 (4H, m)

REFERENCE EXAMPLE 14

4-Benzyl-1,2-dihydro-5-trifluoromethyl-3H-pyrazol-3-one

The title compound was prepared in a similar manner to that described in Reference Example 11 using ethyl trifluoroacetoacetate instead of methyl acetoacetate and using benzyl bromide instead of 4-isopropylbenzyl chloride.
$^1$H-NMR (DMSO-$d_6$) δ ppm:
3.73 (2H, s), 7.05-7.35 (5H, m), 12.50-13.10 (1H, brs)

REFERENCE EXAMPLE 15

1,2-Dihydro-4-[(4-methoxyphenyl)methyl]-5-methyl-3H-pyrazol-3-one

The title compound was prepared in a similar manner to that described in Reference Example 11 using 4-methoxybenzyl bromide instead of 4-isopropylbenzyl chloride.
$^1$H-NMR (DMSO-$d_6$) δ ppm:
1.99 (3H, s), 3.47 (2H, s), 3.69 (3H, s), 6.75-6.85 (2H, m), 7.00-7.10 (2H, m), 8.70-11.70 (2H, br)

REFERENCE EXAMPLE 16

4-Benzyl-1,2-dihydro-5-methyl-3H-pyrazol-3-one

The title compound was prepared in a similar manner to that described in Reference Example 11 using benzyl bromide instead of 4-isopropylbenzyl chloride.
$^1$H-NMR (DMSO-$d_6$) δ ppm:
2.00 (3H, s), 3.54 (2H, s), 7.05-7.30 (5H, s)

REFERENCE EXAMPLE 17

4-[(4-Isopropoxyphenyl)methyl]-5-methyl-3-(2,3,4,6-tetra-O-acetyl-β-D-glucopyranosyloxy)-1H-pyrazole To a suspension of 1,2-dihydro-4-[(4-isopropoxyphenyl)methyl]-5-methyl-3H-pyrazol-3-one (46 mg), acetobromo-α-D-glucose (99 mg) and 4 A molecular sieves in tetrahydrofuran (3 mL) was added silver carbonate (66 mg), and the mixture was stirred under shading the light at 65° C. overnight. The reaction mixture was purified by column chromatography on aminopropyl silica gel (eluent: tetrahydrofuran). Further purification by preparative thin layer chromatography on silica gel (developing solvent: ethyl acetate/hexane=2/1) afforded 4-[(4-isopropoxyphenyl)methyl]-5-methyl-3-(2,3,4,6-tetra-O-acetyl-β-D-glucopyranosyloxy)-1H-pyrazole (42 mg).
1H-NMR (CDCl3) δ ppm:
1.25-1.35 (6H, m), 1.88 (3H, s), 2.01 (3H, s), 2.03 (3H, s), 2.05 (3H, s), 2.10 (3H, s), 3.45-3.65 (2H, m), 3.80-3.90 (1H, m), 4.13 (1H, dd, J=2.3, 12.4 Hz), 4.31 (1H, dd, J=4.0, 12.4

Hz), 4.40-4.55 (1H, m), 5.15-5.35 (3H, m), 5.50-5.60 (1H, m), 6.70-6.80 (2H, m), 6.95-7.05 (2H, m).

REFERENCE EXAMPLE 18

5-Methyl-4-[(4-propylphenyl)methyl]-3-(2,3,4,6-tetra-O-acetyl-β-D-glucopyranosyloxy)-1H-pyrazole The title compound was prepared in a similar manner to that described in Reference Example 17 using 1,2-dihydro-5-methyl-4-[(4-propylphenyl)methyl]-3H-pyrazol-3-one instead of 1,2-dihydro-4-[(4-isopropoxyphenyl)methyl]-5-methyl-3H-pyrazol-3-one.
$^1$H-NMR (CDCl$_3$) δ ppm:
0.91 (3H, t, J=7.3 Hz), 1.50-1.65 (2H, m), 1.86 (3H, s), 2.01 (3H, s), 2.03 (3H, s), 2.05 (3H, s), 2.10 (3H, s), 2.45-2.55 (2H, m), 3.55 (1H, d, J=15.8 Hz), 3.63 (1H, d, J=15.8 Hz), 3.80-3.90 (1H, m), 4.13 (1H, dd, J=2.3, 12.4 Hz), 4.30 (1H, dd, J=3.9, 12.4 Hz), 5.15-5.35 (3H, m), 5.50-5.60 (1H, m), 7.00-7.20 (4H, m)

REFERENCE EXAMPLE 19

4-[(4-Isobutylphenyl)methyl]-5-methyl-3-(2,3,4,6-tetra-O-acetyl-β-D-glucopyranosyloxy)-1H-pyrazole The title compound was prepared in a similar manner to that described in Reference Example 17 using 1,2-dihydro-4-[(4-isobutylphenyl)methyl]-5-methyl-3H-pyrazol-3-one instead of 1,2-dihydro-4-[(4-isopropoxyphenyl)methyl]-5-methyl-3H-pyrazol-3-one.
$^1$H-NMR (CDCl$_3$) δ ppm:
0.87 (6H, d, J=6.6 Hz), 1.70-1.85 (1H, m), 1.87 (3H, s), 2.01 (3H, s), 2.03 (3H, s), 2.06 (3H, s), 2.10 (3H, s), 2.40 (2H, d, J=7.2 Hz), 3.56 (1H, d, J=15.8 Hz), 3.63 (1H, d, J=15.8 Hz), 3.80-3.90 (1H, m), 4.14 (1H, dd, J=2.3, 12.4 Hz), 4.31 (1H, dd, J=4.0, 12.4 Hz), 5.15-5.35 (3H, m), 5.50-5.60 (1H, m), 6.95-7.10 (4H, m)

REFERENCE EXAMPLE 20

5-Methyl-4-[(4-propoxyphenyl)methyl]-3-(2,3,4,6-tetra-O-acetyl-β-D-glucopyranosyloxy)-1H-pyrazole The title compound was prepared in a similar manner to that described in Reference Example 17 using 1,2-dihydro-5-methyl-4-[(4-propoxyphenyl)methyl]-3H-pyrazol-3-one instead of 1,2-dihydro-4-[(4-isopropoxyphenyl)methyl]-5-methyl-3H-pyrazol-3-one
$^1$H-NMR (CDCl$_3$) δ ppm:
1.01 (3H, t, J=7.4 Hz), 1.70-1.85 (2H, m), 1.89 (3H, s) 2.01 (3H, s), 2.03 (3H, s), 2.06 (3H, s), 2.10 (3H, s) 3.53 (1H, d, J=15.7 Hz), 3.59 (1H, d, J=15.7 Hz), 3.80-3.95 (3H, m), 4.14 (1H, dd, J=2.3, 12.4 Hz), 4.31 (1H, dd, J=4.0, 12.4 Hz), 5.15-5.35 (3H, m), 5.50-5.60 (1H, m), 6.70-6.80 (2H, m), 6.95-7.10 (2H, m)

REFERENCE EXAMPLE 21

4-[(4-Ethoxyphenyl)methyl]-5-methyl-3-(2,3,4,6-tetra-O-acetyl-β-D-glucopyranosyloxy)-1H-pyrazole The title compound was prepared in a similar manner to that described in Reference Example 17 using 4-[(4-ethoxyphenyl)methyl]-1,2-dihydro-5-methyl-3H-pyrazol-3-one instead of 1,2-dihydro-4-[(4-isopropoxyphenyl)methyl]-5-methyl-3H-pyrazol-3-one.
$^1$H-NMR (CDCl$_3$) δ ppm:
1.38 (3H, t, J=7.0 Hz), 1.89 (3H, s), 2.01 (3H, s), 2.03 (3H, s), 2.06 (3H, s), 2.10 (3H, s), 3.53 (1H, d, J=15.8 Hz), 3.59 (1H, d, J=15.8 Hz), 3.80-3.90 (1H, m), 3.98 (2H, q, J=7.0 Hz), 4.13 (1H, dd, J=2.3, 12.4 Hz), 4.31 (1H, dd, J=4.0, 12.4), 5.15-5.30 (3H, m), 5.50-5.60 (1H, m), 6.70-6.80 (2H, m), 6.95-7.10 (2H, m)

REFERENCE EXAMPLE 22

5-Methyl-3-(2,3,4,6-tetra-O-acetyl-β-D-glucopyranosyloxy)-4-[(4-trifluoromethylphenyl)methyl]-1H-pyrazole The title compound was prepared in a similar manner to that described in Reference Example 17 using 1,2-dihydro-5-methyl-4-[(4-trifluoromethylphenyl)methyl]-3H-pyrazol-3-one instead of 1,2-dihydro-4-[(4-isopropoxyphenyl)methyl]-5-methyl-3H-pyrazol-3-one.
$^1$H-NMR (CDCl$_3$) δ ppm:
1.85 (3H, s), 2.01 (3H, s), 2.03 (3H, s), 2.06 (3H, s), 2.14 (3H, s), 3.65 (1H, d, J=15.9 Hz), 3.71 (1H, d, J=15.9 Hz), 3.80-3.90 (1H, m), 4.14 (1H, dd, J=2.4, 12.4 Hz), 4.31 (1H, dd, J=4.0, 12.4 Hz), 5.15-5.40 (3H, m), 5.55-5.65 (1H, m), 7.20-7.30 (2H, m), 7.45-7.55 (2H, m)

REFERENCE EXAMPLE 23

4-[(4-tert-Butylphenyl)methyl]-5-methyl-3-(2,3,4,6-tetra-O-acetyl-β-D-glucopyranosyloxy)-1H-pyrazole The title compound was prepared in a similar manner to that described in Reference Example 17 using 4-[(4-tertbutylphenyl)methyl]-1,2-dihydro-5-methyl-3H-pyrazol-3-one instead of 1,2-dihydro-4-[(4-isopropoxyphenyl)methyl]-5-methyl-3H-pyrazol-3-one.
$^1$H-NMR (CDCl$_3$) δ ppm:
1.27 (9H, s), 1.84 (3H, s), 2.01 (3H, s), 2.03 (3H, s), 2.06 (3H, s), 2.14 (3H, s), 3.56 (1H, d, J=15.8 Hz), 3.64 (1H, d, J=15.8 Hz), 3.80-3.90 (1H, m), 4.13 (1H, dd, J=2.3, 12.4 Hz), 4.31 (1H, dd, J=4.0, 12.4 Hz), 5.15-5.30 (3H, m), 5.50-5.60 (1H, m), 7.00-7.10 (2H, m), 7.20-7.30 (2H, m)

REFERENCE EXAMPLE 24

4-[(4-Butoxyphenyl)methyl]-5-methyl-3-(2,3,4,6-tetra-O-acetyl-β-D-glucopyranosyloxy)-1H-pyrazole The title compound was prepared in a similar manner to that described in Reference Example 17 using 4-[(4-butoxyphenyl)methyl]-1,2-dihydro-5-methyl-3H-pyrazol-3-one instead of 1,2-dihydro-4-[(4-isopropoxyphenyl)methyl]-5-methyl-3H-pyrazol-3-one.
$^1$H-NMR (CDCl$_3$) δ ppm:
0.96 (3H, t, J=7.4 Hz), 1.40-1.55 (2H, m), 1.65-1.80 (2H, m), 1.88 (3H, s), 2.01 (3H, s), 2.03 (3H, s), 2.06 (3H, s), 2.10 (3H, s), 3.52 (1H, d, J=15.8 Hz), 3.59 (1H, d, J=15.8 Hz), 3.80-3.90 (1H, m), 3.91 (2H, t, J=6.5 Hz), 4.13 (1H, dd, J=2.3, 12.4 Hz), 4.31 (1H, dd, J=4.0, 12.4 Hz), 5.15-5.30 (3H, m), 5.50-5.60 (1H, m), 6.70-6.80 (2H, m), 6.95-7.10 (2H, m)

REFERENCE EXAMPLE 25

5-Methyl-4-[(4-methylthiophenyl)methyl]-3-(2,3,4,6-tetra-O-acetyl-β-D-glucopyranosyloxy)-1H-pyrazole The title compound was prepared in a similar manner to that described in Reference Example 17 using 1,2-dihydro- 5-methyl-4-[(4-methylthiophenyl)methyl]-3H-pyrazol-3-one instead of 1,2-dihydro-4-[(4-isopropoxyphenyl)methyl]-5-methyl-3H-pyrazol-3-one.

$^1$H-NMR (CDCl$_3$) δ ppm:
1.88 (3H, s), 2.01 (3H, s), 2.03 (3H, s), 2.07 (3H, s), 2.12 (3H, s), 2.44 (3H, s), 3.50-3.65 (2H, m), 3.80-3.90 (1H, m), 4.13 (1H, dd, J=2.4, 12.4 Hz), 4.31 (1H, dd, J=4.1, 12.4 Hz), 5.15-5.30 (3H, m), 5.55-5.65 (1H, m), 7.00-7.10 (2H, m), 7.10-7.20 (2H, m), 8.65-8.85 (1H, brs)

REFERENCE EXAMPLE 26

5-Ethyl-4-[(4-methylthiophenyl)methyl]-3-(2,3,4,6-tetra-O-acetyl-β-D-glucopyranosyloxy)-1H-pyrazole The title compound was prepared in a similar manner to that described in Reference Example 17 using 5-ethyl-1,2-dihydro-4-[(4-methylthiophenyl)methyl]-3H-pyrazol-3-one instead of 1,2-dihydro-4-[(4-isopropoxyphenyl)methyl]-5-methyl-3H-pyrazol-3-one.

$^1$H-NMR (CDCl$_3$) δ ppm:
1.13 (3H, t, J=7.6 Hz), 1.88 (3H, s), 2.01 (3H, s), 2.03 (3H, s), 2.06 (3H, s), 2.44 (3H, s), 2.45-2.55 (2H, m), 3.50-3.70 (2H, m), 3.80-3.90 (1H, m), 4.05-4.20 (1H, m), 4.31 (1H, dd, J=4.0, 12.4 Hz), 5.15-5.35 (3H, m), 5.55-5.65 (1H, m), 7.00-7.10 (2H, m), 7.10-7.20 (2H, m), 8.80-9.20 (1H, brs)

REFERENCE EXAMPLE 27

4-[(4-Isopropylphenyl)methyl]-5-methyl-3-(2,3,4,6-tetra-O-acetyl-β-D-glucopyranosyloxy)-1H-pyrazole The title compound was prepared in a similar manner to that described in Reference Example 17 using 1,2-dihydro-4-[(4-isopropylphenyl)methyl]-5-methyl-3H-pyrazol-3-one instead of 1,2-dihydro-4-[(4-isopropoxyphenyl)methyl]-5-methyl-3H-pyrazol-3-one.

$^1$H-NMR (CDCl$_3$) δ ppm:
1.20 (6H, d, J=6.9 Hz), 1.85 (3H, s), 2.01 (3H, s), 2.03 (3H, s), 2.06 (3H, s), 2.13 (3H, s), 2.75-2.90 (1H, m), 3.56 (1H, d, J=15.8 Hz), 3.63 (1H, d, J=15.8 Hz), 3.80-3.90 (1H, m), 4.05-4.20 (1H, m), 4.31 (1H, dd, J=4.0, 12.4 Hz), 5.15-5.35 (3H, m), 5.50-5.60 (1H, m), 7.00-7.15 (4H, m), 8.70-9.30 (1H, brs)

REFERENCE EXAMPLE 28

4-[(4-Methylthiophenyl)methyl]-3-(2,3,4,6-tetra-O-acetyl-β-D-glucopyranosyloxy)-5-trifluoromethyl-1H-pyrazole To a solution of 1,2-dihydro-4-[(4-methylthiophenyl)-methyl]-5-trifluoromethyl-3H-pyrazol-3-one (2.0 g) in acetonitrile (100 mL) were added acetobromo-α-D-glucose (3.1 g) and potassium carbonate (1.1 g), and the mixture was stirred at room temperature overnight. Water was added to the reaction mixture, and the resulting mixture was extracted with ethyl acetate. The organic layer was washed with a saturated aqueous sodium hydrogen carbonate solution and brine and dried over anhydrous magnesium sulfate. The solvent was removed under reduced pressure, and the residue was purified by column chromatography on silica gel (eluent: hexane/ethyl acetate=1/1) to give 4-[(4-methylthiophenyl)methyl]-3-(2,3,4,6-tetra-O-acetyl-β-D-glucopyranosyloxy)-5-trifluoromethyl-1H-pyrazole (2.0 g).

$^1$H-NMR (CDCl$_3$) δ ppm:
1.91 (3H, s), 2.03 (3H, s), 2.04 (3H, s), 2.09 (3H, s), 2.45 (3H, s), 3.73 (2H, s), 3.75-3.90 (1H, m), 4.15-4.35 (2H, m), 5.15-5.65 (4H, m), 7.00-7.20 (4H, m)

REFERENCE EXAMPLE 29

4-Benzyl-3-(2,3,4,6-tetra-O-acetyl-β-D-glucopyranosyloxy)-5-trifluoromethyl-1H-pyrazole The title compound was prepared in a similar manner to that described in Reference Example 28 using 4-benzyl-1,2-dihydro-5-trifluoromethyl-3H-pyrazol-3-one instead of 1,2-dihydro-4-[(4-methylthiophenyl)methyl]-5-trifluoromethyl-3H-pyrazol-3-one.

$^1$H-NMR (CDCl$_3$) δ ppm:
1.89 (3H, s), 2.02 (3H, s), 2.04 (3H, s), 2.08 (3H, s) 3.70-3.90 (3H, m), 4.15-4.30 (2H, m), 5.10-5.50 (4H, m), 7.10-7.30 (5H, m)

REFERENCE EXAMPLE 30

4-[(4-Methoxyphenyl)methyl]-3-(2,3,4,6-tetra-O-acetyl-β-D-glucopyranosyloxy)-5-trifluoromethyl-1H-pyrazole The title compound was prepared in a similar manner to that described in Reference Example 28 using 1,2-dihydro-4-[(4-methoxyphenyl)methyl]-5-trifluoromethyl-3H-pyrazol-3-one instead of 1,2-dihydro-4-[(4-methylthiophenyl)methyl]-5-trifluoromethyl-3H-pyrazol-3-one.

$^1$H-NMR (CDCl$_3$) δ ppm:
1.93 (3H, s), 2.03 (3H, s), 2.05 (3H, s), 2.09 (3H, s), 3.65-3.75 (2H, m), 3.77 (3H, s), 3.75-3.90 (1H, m), 4.15-4.35 (2H, m), 5.10-5.45 (4H, m), 6.75-6.85 (2H, m), 7.00-7.15 (2H, m)

REFERENCE EXAMPLE 31

4-[(4-Methoxyphenyl)methyl]-5-methyl-3-(2,3,4,6-tetra-O-acetyl-β-D-glucopyranosyloxy)-1H-pyrazole The title compound was prepared in a similar manner to that described in Reference Example 17 using 1,2-dihydro-4-[(4-methoxyphenyl)methyl]-5-methyl-3H-pyrazol-3-one instead of 1,2-dihydro-4-[(4-isopropoxyphenyl)methyl]-5-methyl-3H-pyrazol-3-one.

$^1$H-NMR (CDCl$_3$) δ ppm:
1.89 (3H, s), 2.02 (3H, s), 2.03 (3H, s), 2.05 (3H, s), 2.10 (3H, s), 3.45-3.65 (2H, m), 3.76 (3H, s), 3.80-3.90 (1H, m), 4.11 (1H, dd, J=2.2, 12.4 Hz), 4.30 (1H, dd, J=4.0, 12.4 Hz), 5.15-5.35 (3H, m), 5.50-5.60 (1H, m), 6.70-6.85 (2H, m), 7.00-7.10 (2H, m)

REFERENCE EXAMPLE 32

4-Benzyl-5-methyl-3-(2,3,4,6-tetra-O-acetyl-β-D-glucopyranosyloxy)-1H-pyrazole

The title compound was prepared in a similar manner to that described in Reference Example 17 using 4-benzyl-1,2-dihydro-5-methyl-3H-pyrazol-3-one instead of 1,2-dihydro-4-[(4-isopropoxyphenyl)methyl]-5-methyl-3H-pyrazol-3-one.

$^1$H-NMR (CDCl$_3$) δ ppm:
1.86 (3H, s), 2.01 (3H, s), 2.03 (3H, s), 2.06 (3H, s) 2.11 (3H, s), 3.59 (1H, d, J=15.8 Hz), 3.66 (1H, d, J=15.8 Hz), 3.80-3.90 (1H, m), 4.11 (1H, dd, J=2.3, 12.4 Hz), 4.30 (1H, dd, J=4.0, 12.4 Hz), 5.15-5.30 (3H, m), 5.50-5.65 (1H, m), 7.05-7.30 (5H, m), 8.75-9.55 (1H, brs)

REFERENCE EXAMPLE 33

4-[(4-Methoxyphenyl)methyl]-1,5-dimethyl-3-(2,3,4,6-tetra-O-acetyl-β-D-glucopyranosyloxy)pyrazole A suspension of 4-[(4-methoxyphenyl)methyl]-5-methyl-3-(2,3,4,6-tetra-O-acetyl-β-D-glucopyranosyloxy)-1H-pyrazole (18 mg), potassium carbonate (14 mg) and iodomethane (4.7 mg) in acetonitrile (2 mL) was stirred at 75° C. overnight. The reaction mixture was filtered through Celite®, and the solvent of the filtrate was removed under reduced pressure. The residue was purified by preparative thin layer chromatography on silica gel (developing solvent: benzene/acetone=2/1) to give 4-[(4-methoxyphenyl)methyl]-1,5-dimethyl-3-(2,3,4,6-tetra-O-acetyl-β-D-glucopyranosyloxy)pyrazole (4 mg).

$^1$H-NMR (CDCl$_3$) δ ppm:

1.90 (3H, s), 2.01 (3H, s), 2.03 (3H, s), 2.06 (3H, s) 2.07 (3H, s), 3.45-3.60 (2H, m), 3.60 (3H, s), 3.76 (3H, s), 3.80-3.90 (1H, m), 4.13 (1H, dd, J=2.4, 12.4 Hz), 4.29 (1H, dd, J=4.1, 12.4 Hz), 5.15-5.30 (3H, m), 5.50-5.60 (1H, m), 6.70-6.80 (2H, m), 7.00-7.10 (2H, m)

REFERENCE EXAMPLE 34

1-Methyl-4-[(4-methylthiophenyl)methyl]-3-(2,3,4,6-tetra-O-acetyl-β-D-glucopyranosyloxy)-5-trifluoromethylpyrazole A suspension of 4-[(4-methylthiophenyl)methyl]-3-(2,3,4,6-tetra-O-acetyl-β-D-glucopyranosyloxy)-5-trifluoromethyl-1H-pyrazole (30 mg), potassium carbonate (8.0 mg) and iodomethane (8.2 mg) in tetrahydrofuran (1 mL) was stirred at 75° C. overnight. The reaction mixture was filtered through Celite®, and the solvent of the filtrate was removed under reduced pressure. The residue was purified by preparative thin layer chromatography on silica gel (developing solvent: dichloromethane/ethyl acetate=5/1) to give 1-methyl-4-[(4-methylthiophenyl)methyl]-3-(2,3,4,6-tetra-O-acetyl-β-D-glucopyranosyloxy)-5-trifluoromethylpyrazole (13 mg).

$^1$H-NMR (CDCl$_3$) δ ppm:

1.89 (3H, s), 2.02 (3H, s), 2.04 (3H, s), 2.07 (3H, s) 2.44 (3H, s), 3.65-3.95 (6H, m), 4.14 (1H, dd, J=2.3, 12.4 Hz), 4.29 (1H, dd, J=4.3, 12.4 Hz), 5.15-5.35 (3H, m), 5.50-5.65 (1H, m), 7.00-7.20 (4H, m)

REFERENCE EXAMPLE 35

1-Ethyl-4-[(4-methylthiophenyl)methyl]-3-(2,3,4,6-tetra-O-acetyl-β-D-glucopyranosyloxy)-5-trifluoromethylpyrazole The title compound was prepared in a similar manner to that described in Reference Example 34 using iodoethane instead of iodomethane.

$^1$H-NMR (CDCl$_3$) δ ppm:

1.40 (3H, t, J=7.2 Hz), 1.90 (3H, s), 2.02 (3H, s), 2.04 (3H, s), 2.06 (3H, s), 2.44 (3H, s), 3.72 (2H, s), 3.80-3.90 (1H, m), 4.05-4.20 (3H, m), 4.27 (1H, dd, J=4.5, 12.4 Hz), 5.10-5.35 (3H, m), 5.55-5.65 (1H, m), 7.00-7.10 (2H, m), 7.10-7.20 (2H, m)

REFERENCE EXAMPLE 36

4-[(4-Methylthiophenyl)methyl]-1-propyl-3-(2,3,4,6-tetra-O-acetyl-β-D-glucopyranosyloxy)-5-trifluoromethylpyrazole The title compound was prepared in a similar manner to that described in Reference Example 34 using 1-iodopropane instead of iodomethane.

$^1$H-NMR (CDCl$_3$) δ ppm:

0.92 (3H, t, J=7.4 Hz), 1.75-1.90 (2H, m), 1.89 (3H, s), 2.02 (3H, s), 2.04 (3H, s), 2.06 (3H, s), 2.44 (3H, s), 3.72 (2H, s), 3.80-3.90 (1H, m), 3.90-4.05 (2H, m), 4.12 (1H, dd, J=2.3, 12.4 Hz), 4.27 (1H, dd, J=4.5, 12.4 Hz), 5.10-5.35 (3H, m), 5.55-5.65 (1H, m), 7.00-7.10 (2H, m), 7.10-7.20 (2H, m)

REFERENCE EXAMPLE 37

3-(β-D-Glucopyranosyloxy)-4-[(4-isopropoxyphenyl)methyl]-5-methyl-1H-pyrazole

To a solution of 4-[(4-isopropoxyphenyl)methyl]-5-methyl-3-(2,3,4,6-tetra-O-acetyl-β-D-glucopyranosyloxy)-1H-pyrazole (61 mg) in ethanol (3 mL) was added 1 mol/L aqueous sodium hydroxide solution (0.53 mL), and the mixture was stirred at room temperature for 2 hours. The solvent was removed under reduced pressure, and the residue was purified by solid phase extraction on ODS (washing solvent: distilled water, eluent: methanol) to give 3-(β-D-glucopyranosyloxy)-4-[(4-isopropoxyphenyl)methyl]-5-methyl-1H-pyrazole (39 mg).

$^1$H-NMR (CD$_3$OD) δ ppm:

1.26 (6H, d, J=5.9 Hz), 2.05 (3H, s), 3.25-3.45 (4H, m), 3.55-3.75 (3H, m), 3.75-3.90 (1H, m), 4.45-4.60 (1H, m), 5.00-5.10 (1H, m), 6.70-6.80 (2H, m), 7.00-7.15 (2H, m)

REFERENCE EXAMPLE 38

3-(β-D-Glucopyranosyloxy)-5-methyl-4-[(4-propylphenyl)-methyl]-1H-pyrazole

The title compound was prepared in a similar manner to that described in Reference Example 37 using 5-methyl-4-[(4-propylphenyl)methyl]-3-(2,3,4,6-tetra-O-acetyl-β-D-glucopyranosyloxy)-1H-pyrazole instead of 4-[(4-isopropoxyphenyl)methyl]-5-methyl-3-(2,3,4,6-tetra-O-acetyl-β-D-glucopyranosyloxy)-1H-pyrazole.

$^1$H-NMR (CD$_3$OD) δ ppm:

0.91 (3H, t, J=7.5 Hz), 1.50-1.65 (2H, m), 2.05 (3H, s) 2.45-2.60 (2H, m), 3.25-3.45 (4H, m), 3.55-3.75 (3H, m), 3.83 (1H, d, J=11.9 Hz), 5.00-5.10 (1H, m), 7.00-7.15 (4H, m)

EXAMPLE 39

3-(β-D-Glucopyranosyloxy)-4-[(4-isobutylphenyl)methyl]-5-methyl-1H-pyrazole

The title compound was prepared in a similar manner to that described in Reference Example 37 using 4-[(4-isobutylphenyl)methyl]-5-methyl-3-(2,3,4,6-tetra-O-acetyl-β-D-glucopyranosyloxy)-1H-pyrazole instead of 4-[(4-isopropoxyphenyl)methyl]-5-methyl-3-(2,3,4,6-tetra-O-acetyl-β-D-glucopyranosyloxy)-1H-pyrazole.

$^1$H-NMR (CD$_3$OD) δ ppm:

0.87 (6H, d, J=6.6 Hz), 1.70-1.90 (1H, m), 2.04 (3H, s), 2.41 (2H, d, J=7.1 Hz), 3.25-3.45 (4H, m), 3.55-3.90 (4H, m), 5.00-5.10 (1H, m), 6.95-7.15 (4H, m)

REFERENCE EXAMPLE 40

3-(β-D-Glucopyranosyloxy)-5-methyl-4-[(4-propoxyphenyl)-methyl]-1H-pyrazole

The title compound was prepared in a similar manner to that described in Reference Example 37 using 5-methyl-4-[(4-propoxyphenyl)methyl]-3-(2,3,4,6-tetra-O-acetyl-β-D-glucopyranosyloxy)-1H-pyrazole instead of 4-[(4-isopropoxyphenyl)methyl]-5-methyl-3-(2,3,4,6-tetra-O-acetyl-β-D-glucopyranosyloxy)-1H-pyrazole.

$^1$H-NMR (CD$_3$OD) δ ppm:
1.02 (3H, t, J=7.4 Hz), 1.65-1.80 (2H, m), 2.05 (3H, s), 3.25-3.45 (4H, m), 3.60-3.75 (3H, m), 3.80-3.90 (3H, m), 5.00-5.10 (1H, m), 6.70-6.85 (2H, m), 7.05-7.15 (2H, m)

REFERENCE EXAMPLE 41

4-[(4-Ethoxyphenyl)methyl]-3-(β-D-glucopyranosyloxy)-5-methyl-1H-pyrazole

The title compound was prepared in a similar manner to that described in Reference Example 37 using 4-[(4-ethoxyphenyl)methyl]-5-methyl-3-(2,3,4,6-tetra-O-acetyl-β-D-glucopyranosyloxy)-1H-pyrazole instead of 4-[(4-isopropoxy-phenyl)methyl]-5-methyl-3-(2,3,4,6-tetra-O-acetyl-β-D-glucopyranosyloxy)-1H-pyrazole.

$^1$H-NMR (CD$_3$OD) δ ppm:
1.34 (3H, t, J=7.0 Hz), 2.05 (3H, s), 3.25-3.45 (4H, m), 3.60-3.75 (3H, m), 3.80-3.90 (1H, m), 3.97 (2H, q, J=7.0 Hz), 5.00-5.10 (1H, m), 6.70-6.85 (2H, m), 7.05-7.15 (2H, m)

REFERENCE EXAMPLE 42

3-(β-D-Glucopyranosyloxy)-5-methyl-4-[(4-trifluoromethylphenyl)methyl]-1H-pyrazole The title compound was prepared in a similar manner to that described in Reference Example 37 using 5-methyl-3-(2,3,4,6-tetra-O-acetyl-β-D-glucopyranosyloxy)-4-[(4-trifluoromethylphenyl)methyl]-1H-pyrazole instead of 4-[(4-isopropoxyphenyl)methyl]-5-methyl-3-(2,3,4,6-tetra-O-acetyl-β-D-glucopyranosyloxy)-1H-pyrazole.

$^1$H-NMR (CD$_3$OD) δ ppm:
2.08 (3H, s), 3.20-3.40 (4H, m), 3.67 (1H, dd, J=5.0, 11.9 Hz), 3.75-3.90 (3H, m), 5.00-5.10 (1H, m), 7.30-7.45 (2H, m), 7.45-7.60 (2H, m)

REFERENCE EXAMPLE 43

4-[(4-tert-Butylphenyl)methyl]-3-(β-D-glucopyranosyloxy)-5-methyl-1H-pyrazole

The title compound was prepared in a similar manner to that described in Reference Example 37 using 4-[(4-tertbutylphenyl)methyl]-5-methyl-3-(2,3,4,6-tetra-O-acetyl-β-D-glucopyranosyloxy)-1H-pyrazole instead of 4-[(4-isopropoxyphenyl)methyl]-5-methyl-3-(2,3,4,6-tetra-O-acetyl-β-D-glucopyranosyloxy)-1H-pyrazole.

$^1$H-NMR (CD$_3$OD) δ ppm:
1.28 (9H, s), 2.06 (3H, s), 3.25-3.45 (4H, m), 3.60-3.90 (4H, m), 5.00-5.10 (1H, m), 7.05-7.15 (2H, m), 7.20-7.30 (2H, m)

REFERENCE EXAMPLE 44

4-[(4-Butoxyphenyl)methyl]-3-(β-D-glucopyranosyloxy)-5-methyl-1H-pyrazole

The title compound was prepared in a similar manner to that described in Reference Example 37 using 4-[(4-butoxyphenyl)methyl]-5-methyl-3-(2,3,4,6-tetra-O-acetyl-β-D-glucopyranosyloxy)-1H-pyrazole instead of 4-[(4-isopropoxyphenyl)methyl]-5-methyl-3-(2,3,4,6-tetra-O-acetyl-β-D-glucopyranosyloxy)-1H-pyrazole.

$^1$H-NMR (CD$_3$OD) δ ppm:
0.97 (3H, t, J=7.4 Hz), 1.40-1.55 (2H, m), 1.65-1.80 (2H, m) 2.05 (3H, s), 3.30-3.45 (4H, m), 3.60-3.75 (3H, m), 3.83 (1H, d, J=12.0 Hz), 3.91 (2H, t, J=6.4 Hz), 5.00-5.10 (1H, m) 6.70-6.85 (2H, m), 7.05-7.15 (2H, m)

REFERENCE EXAMPLE 45

3-(β-D-Glucopyranosyloxy)-5-methyl-4-[(4-methylthiophenyl)-methyl]-1H-pyrazole

The title compound was prepared in a similar manner to that described in Reference Example 37 using 5-methyl-4-[(4-methylthiophenyl)methyl]-3-(2,3,4,6-tetra-O-acetyl-β-D-glucopyranosyloxy)-1H-pyrazole instead of 4-[(4-isopropoxyphenyl)methyl]-5-methyl-3-(2,3,4,6-tetra-O-acetyl-β-D-glucopyranosyloxy)-1H-pyrazole.

$^1$H-NMR (CD$_3$OD) δ ppm:
2.06 (3H, s), 2.42 (3H, s), 3.20-3.45 (4H, m), 3.55-3.75 (3H, m), 3.80-3.90 (1H, m), 5.00-5.10 (1H, m), 7.05-7.20 (4H, m)

REFERENCE EXAMPLE 46

5-Ethyl-3-(β-D-glucopyranosyloxy)-4-[(4-methylthiophenyl)-methyl]-1H-pyrazole

The title compound was prepared in a similar manner to that described in Reference Example 37 using 5-ethyl-4-[(4-methylthiophenyl)methyl]-3-(2,3,4,6-tetra-O-acetyl-β-D-glucopyranosyloxy)-1H-pyrazole instead of 4-[(4-isopropoxyphenyl)methyl]-5-methyl-3-(2,3,4,6-tetra-O-acetyl-β-D-glucopyranosyloxy)-1H-pyrazole.

$^1$H-NMR (CD$_3$OD) δ ppm:
1.06 (3H, t, J=7.6 Hz), 2.42 (3H, s), 2.47 (2H, q, J=7.6 Hz), 3.25-3.45 (4H, m), 3.60-3.80 (3H, m), 3.80-3.90 (1H, m), 5.00-5.10 (1H, m), 7.10-7.20 (4H, m)

REFERENCE EXAMPLE 47

3-(β-D-Glucopyranosyloxy)-4-[(4-isopropylphenyl)methyl]-5-methyl-1H-pyrazole

The title compound was prepared in a similar manner to that described in Reference Example 37 using 4-[(4-isopropyl-phenyl)methyl]-5-methyl-3-(2,3,4,6-tetra-O-acetyl-β-D-glucopyranosyloxy)-1H-pyrazole instead of 4-[(4-isopropoxyphenyl)methyl]-5-methyl-3-(2,3,4,6-tetra-O-acetyl-β-D-glucopyranosyloxy)-1H-pyrazole.

$^1$H-NMR (CD$_3$OD) δ ppm:
1.20 (6H, d, J=6.9 Hz), 2.05 (3H, s), 2.75-2.90 (1H, m), 3.25-3.45 (4H, m), 3.55-3.90 (4H, m), 5.00-5.10 (1H, m), 7.00-7.15 (4H, m)

REFERENCE EXAMPLE 48

3-(β-D-Glucopyranosyloxy)-4-[(4-methylthiophenyl)methyl]-5-trifluoromethyl-1H-pyrazole The title compound was prepared in a similar manner to that described in Reference Example 37 using 4-[(4-methylthiophenyl)methyl]-3-(2,3,4,6-tetra-O-acetyl-β-D-glucopyranosyloxy)-5-trifluoromethyl-1H-pyrazole instead of 4-[(4-isopropoxyphenyl)methyl]-5-methyl-3-(2,3,4,6-tetra-O-acetyl-β-D-glucopyranosyloxy)-1H-pyrazole.
$^1$H-NMR (CD$_3$OD) δ ppm:
2.42 (3H, s), 3.25-3.50 (4H, m), 3.69 (1H, dd, J=4.9, 12.0 Hz), 3.75-3.90 (3H, m), 4.90-5.10 (1H, m), 7.10-7.20 (4H, m)

REFERENCE EXAMPLE 49

4-Benzyl-3-(β-D-glucopyranosyloxy)-5-trifluoromethyl-1H-pyrazole

The title compound was prepared in a similar manner to that described in Reference Example 37 using 4-benzyl-3-(2,3,4,6-tetra-O-acetyl-β-D-glucopyranosyloxy)-5-trifluoromethyl-1H-pyrazole instead of 4-[(4-isopropoxyphenyl)methyl]-5-methyl-3-(2,3,4,6-tetra-O-acetyl-β-D-glucopyranosyloxy)-1H-pyrazole.
$^1$H-NMR (CD$_3$OD) δ ppm:
3.25-3.45 (4H, m), 3.67 (1H, dd, J=5.3, 12.0 Hz), 3.80-3.95 (3H, m), 4.97 (1H, d, J=7.4 Hz), 7.05-7.25 (5H, m)

REFERENCE EXAMPLE 50

3-(β-D-Glucopyranosyloxy)-4-[(4-methoxyphenyl)methyl]-5-trifluoromethyl-1H-pyrazole The title compound was prepared in a similar manner to that described in Reference Example 37 using 4-[(4-methoxyphenyl)methyl]-3-(2,3,4,6-tetra-O-acetyl-β-D-glucopyranosyloxy)-5-trifluoromethyl-1H-pyrazole instead of 4-[(4-isopropoxyphenyl)methyl]-5-methyl-3-(2,3,4,6-tetra-O-acetyl-β-D-glucopyranosyloxy)-1H-pyrazole.
$^1$H-NMR (CD$_3$OD) δ ppm:
3.25-3.45 (4H, m), 3.67 (1H, d, J=5.4, 12.1 Hz), 3.73 (3H, s), 3.75-3.90 (3H, m), 4.90-5.00 (1H, m), 6.70-6.85 (2H, m), 7.05-7.15 (2H, m)

REFERENCE EXAMPLE 51

3-(β-D-Glucopyranosyloxy)-4-[(4-methoxyphenyl)methyl]-5-methyl-1H-pyrazole

The title compound was prepared in a similar manner to that described in Reference Example 37 using 4-[(4-methoxyphenyl)methyl]-5-methyl-3-(2,3,4,6-tetra-O-acetyl-β-D-glucopyranosyloxy)-1H-pyrazole instead of 4-[(4-isopropoxyphenyl)methyl]-5-methyl-3-(2,3,4,6-tetra-O-acetyl-β-D-glucopyranosyloxy)-1H-pyrazole.
$^1$H-NMR (CD$_3$OD) δ ppm:
2.04 (3H, s), 3.25-3.45 (4H, m), 3.55-3.75 (3H, m), 3.73 (3H, s), 3.80-3.90 (1H, m), 5.00-5.10 (1H, m), 6.75-6.85 (2H, m), 7.05-7.15 (2H, m)

REFERENCE EXAMPLE 52

4-Benzyl-3-(β-D-glucopyranosyloxy)-5-methyl-1H-pyrazole

The title compound was prepared in a similar manner to that described in Reference Example 37 using 4-benzyl-5-methyl-3-(2,3,4,6-tetra-O-acetyl-β-D-glucopyranosyloxy)-1H-pyrazole instead of 4-[(4-isopropoxyphenyl)methyl]-5-methyl-3-(2,3,4,6-tetra-O-acetyl-β-D-glucopyranosyloxy)-1H-pyrazole.
$^1$H-NMR (CD$_3$OD) δ ppm:
2.05 (3H, s), 3.25-3.45 (4H, m), 3.60-3.90 (4H, m), 5.00-5.10 (1H, m), 7.05-7.25 (5H, m)

REFERENCE EXAMPLE 53

3-(β-D-Glucopyranosyloxy)-4-[(4-methoxyphenyl)methyl]-1,5-dimethylpyrazole

The title compound was prepared in a similar manner to that described in Reference Example 37 using 4-[(4-methoxyphenyl)methyl]-1,5-dimethyl-3-(2,3,4,6-tetra-O-acetyl-β-D-glucopyranosyloxy)pyrazole instead of 4-[(4-isopropoxyphenyl)methyl]-5-methyl-3-(2,3,4,6-tetra-O-acetyl-β-D-glucopyranosyloxy)-1H-pyrazole.
$^1$H-NMR (CD$_3$OD) δ ppm:
2.06 (3H, s), 3.25-3.45 (4H, m), 3.55-3.70 (6H, m), 3.73 (3H, s), 3.75-3.90 (1H, m), 5.00-5.10 (1H, m), 6.70-6.80 (2H, m), 7.05-7.15 (2H, m)

REFERENCE EXAMPLE 54

3-(β-D-Glucopyranosyloxy)-1-methyl-4-[(4-methylthiophenyl)-methyl]-5-trifluoromethylpyrazole The title compound was prepared in a similar manner to that described in Reference Example 37 using 1-methyl-4-[(4-methylthiophenyl)methyl]-3-(2,3,4,6-tetra-O-acetyl-β-D-glucopyranosyloxy)-5-trifluoromethylpyrazole instead of 4-[(4-isopropoxyphenyl)methyl]-5-methyl-3-(2,3,4,6-tetra-O-acetyl-β-D-glucopyranosyloxy)-1H-pyrazole.
$^1$H-NMR (CD$_3$OD) δ ppm:
2.42 (3H, s), 3.30-3.50 (4H, m), 3.69 (1H, dd, J=4.7, 12.0 Hz), 3.75-3.90 (6H, m), 5.25-5.35 (1H, m), 7.05-7.20 (4H, m)

REFERENCE EXAMPLE 55

1-Ethyl-3-(β-D-glucopyranosyloxy)-4-[(4-methylthiophenyl)-methyl]-5-trifluoromethylpyrazole The title compound was prepared in a similar manner to that described in Reference Example 37 using 1-ethyl-4-[(4-methylthiophenyl)methyl]-3-(2,3,4,6-tetra-O-acetyl-β-D-glucopyranosyloxy)-5-trifluoromethylpyrazole instead of 4-[(4-isopropoxyphenyl)methyl]-5-methyl-3-(2,3,4,6-tetra-O-acetyl-β-D-glucopyranosyloxy)-1H-pyrazole.
$^1$H-NMR (CD$_3$OD) δ ppm:
1.38 (3H, t, J=7.1 Hz), 2.42 (3H, s), 3.30-3.50 (4H, m), 3.60-3.75 (1H, m), 3.75-3.90 (3H, m), 4.14 (2H, q, J=7.1 Hz), 5.25-5.35 (1H, m), 7.05-7.20 (4H, m)

REFERENCE EXAMPLE 56

3-(β-D-Glucopyranosyloxy)-4-[(4-methylthiophenyl)methyl]-1-propyl-5-trifluoromethylpyrazole The title compound was prepared in a similar manner to that described in Reference Example 37 using 4-[(4-methylthio-phenyl)methyl]-1-propyl-3-(2,3,4,6-tetra-O-acetyl-β-D-glucopyranosyloxy)-5-trifluoromethylpyrazole instead of 4-[(4-isopropoxyphenyl)methyl]-5-methyl-3-(2,3,4,6-tetra-O-acetyl-β-D-glucopyranosyloxy)-1H-pyrazole.
$^1$H-NMR (CD$_3$OD) δ ppm:

0.90 (3H, t, J=7.4 Hz), 1.75-1.90 (2H, m), 2.42 (3H, s), 3.30-3.50 (4H, m), 3.69 (1H, dd, J=4.9, 12.0 Hz), 3.75-3.90 (3H, m), 4.00-4.10 (2H, m), 5.25-5.35 (1H, m), 7.05-7.20 (4H, m)

REFERENCE EXAMPLE 57

3-(β-D-Glucopyranosyloxy)-5-methyl-4-[(4-methylphenyl)-methyl]-1H-pyrazole

5-Methyl-4-[(4-methylphenyl)methyl]-3-(2,3,4,6-tetra-O-acetyl-β-D-glucopyranosyloxy)-1H-pyrazole was prepared in a similar manner to that described in Reference Example 17 using 1,2-dihydro-5-methyl-4-[(4-methylphenyl)methyl]-3H-pyrazol-3-one instead of 1,2-dihydro-4-[(4-isopropoxyphenyl)methyl]-5-methyl-3H-pyrazol-3-one. Then, the title compound was prepared in a similar manner to that described in Reference Example 37 using 5-methyl-4-[(4-methylphenyl)methyl]-3-(2,3,4,6-tetra-O-acetyl-β-D-glucopyranosyloxy)-1H-pyrazole instead of 4-[(4-isopropoxyphenyl)methyl]-5-methyl-3-(2,3,4,6-tetra-O-acetyl-β-D-glucopyranosyloxy)-1H-pyrazole.
$^1$H-NMR (CD$_3$OD) δ ppm:
2.04 (3H, s), 2.26 (3H, s), 3.25-3.45 (4H, m), 3.55-3.90 (4H, m), 5.00-5.10 (1H, m), 6.95-7.15 (4H, m)

REFERENCE EXAMPLE 58

4-[(4-Ethylphenyl)methyl]-3-(β-D-glucopyranosyloxy)-5-methyl-1H-pyrazole

4-[(4-Ethylphenyl)methyl]-5-methyl-3-(2,3,4,6-tetra-O-acetyl-β-D-glucopyranosyloxy)-1H-pyrazole was prepared in a similar manner to that described in Reference Example 17 using 4-[(4-ethylphenyl)methyl]-1,2-dihydro-5-methyl-3H-pyrazol-3-one instead of 1,2-dihydro-4-[(4-isopropoxyphenyl)methyl]-5-methyl-3H-pyrazol-3-one. Then, the title compound was prepared in a similar manner to that described in Reference Example 37 using 4-[(4-ethylphenyl)methyl]-5-methyl-3-(2,3,4,6-tetra-O-acetyl-β-D-glucopyranosyloxy)-1H-pyrazole instead of 4-[(4-isopropoxyphenyl)methyl]-5-methyl-3-(2,3,4,6-tetra-O-acetyl-β-D-glucopyranosyloxy)-1H-pyrazole.
$^1$H-NMR (CD$_3$OD) δ ppm:
1.18 (3H, t, J=7.6 Hz), 2.04 (3H, s), 2.57 (2H, q, J=7.6 Hz), 3.25-3.45 (4H, m), 3.55-3.90 (4H, m), 5.00-5.10 (1H, m), 6.95-7.20 (4H, m)

REFERENCE EXAMPLE 59

3-(β-D-Glucopyranosyloxy)-4-[(4-methylphenyl)methyl]-5-trifluoromethyl-1H-pyrazole 4-[(4-Methylphenyl)methyl]-3-(2,3,4,6-tetra-O-acetyl-β-D-glucopyranosyloxy)-5-trifluoromethyl-1H-pyrazole was prepared in a similar manner to that described in Reference Example 28 using 1,2-dihydro-4-[(4-methylphenyl)methyl]-5-trifluoromethyl-3H-pyrazol-3-one instead of 1,2-dihydro-4-[(4-methylthiophenyl)methyl]-5-trifluoromethyl-3H-pyrazol-3-one. Then, the title compound was prepared in a similar manner to that described in Reference Example 37 using 4-[(4-methylphenyl)methyl]-3-(2,3,4,6-tetra-O-acetyl-β-D-glucopyranosyloxy)-5-trifluoromethyl-1H-pyrazole instead of 4-[(4-isopropoxyphenyl)methyl]-5-methyl-3-(2,3,4,6-tetra-O-acetyl-β-D-glucopyranosyloxy)-1H-pyrazole.
$^1$H-NMR (CD$_3$OD) δ ppm:
2.25 (3H, s), 3.20-3.45 (4H, m), 3.55-3.70 (1H, m), 3.70-3.90 (3H, m), 4.80-4.95 (1H, m), 6.90-7.15 (4H, m)

REFERENCE EXAMPLE 60

4-[(4-Ethylphenyl)methyl]-3-(β-D-glucopyranosyloxy)-5-trifluoromethyl-1H-pyrazole 4-[(4-Ethylphenyl)methyl]-3-(2,3,4,6-tetra-O-acetyl-β-D-glucopyranosyloxy)-5-trifluoromethyl-1H-pyrazole was prepared in a similar manner to that described in Reference Example 28 using 4-[(4-ethylphenyl)methyl]-1,2-dihydro-5-trifluoromethyl-3H-pyrazol-3-one instead of 1,2-dihydro-4-[(4-methylthiophenyl)methyl]-5-trifluoromethyl-3H-pyrazol-3-one. Then, the title compound was prepared in a similar manner to that described in Reference Example 37 using 4-[(4-ethyl-phenyl)methyl]-3-(2,3,4,6-tetra-O-acetyl-β-D-glucopyranosyloxy)-5-trifluoromethyl-1H-pyrazole instead of 4-[(4-isopropoxyphenyl)methyl]-5-methyl-3-(2,3,4,6-tetra-O-acetyl-β-D-glucopyranosyloxy)-1H-pyrazole.
$^1$H-NMR (CD$_3$OD) δ ppm:
1.18 (3H, t, J=7.6 Hz), 2.50-2.60 (2H, m), 3.15-3.40 (4H, m), 3.55-3.65 (1H, m), 3.70-3.90 (3H, m), 4.80-4.95 (1H, m), 6.95-7.15 (4H, m)

REFERENCE EXAMPLE 61

3-(β-D-Glucopyranosyloxy)-4-[(4-isopropylphenyl)methyl]-5-trifluoromethyl-1H-pyrazole 4-[(4-Isopropylphenyl)methyl]-3-(2,3,4,6-tetra-O-acetyl-β-D-glucopyranosyloxy)-5-trifluoromethyl-1H-pyrazole was prepared in a similar manner to that described in Reference Example 28 using 1,2-dihydro-4-[(4-isopropylphenyl)methyl]-5-trifluoromethyl-3H-pyrazol-3-one instead of 1,2-dihydro-4-[(4-methylthiophenyl)methyl]-5-trifluoromethyl-3H-pyrazol-3-one. Then, the title compound was prepared in a similar manner to that described in Reference Example 37 using 4-[(4-isopropylphenyl)methyl]-3-(2,3,4,6-tetra-O-acetyl-β-D-glucopyranosyloxy)-5-trifluoromethyl-1H-pyrazole instead of 4-[(4-isopropoxyphenyl)methyl]-5-methyl-3-(2,3,4,6-tetra-O-acetyl-β-D-glucopyranosyloxy)-1H-pyrazole.
$^1$H-NMR (CD$_3$OD) δ ppm:
1.20 (6H, d, J=6.9 Hz), 2.75-2.85 (1H, m), 3.15-3.40 (4H, m) 3.55-3.65 (1H, m), 3.70-3.90 (3H, m), 4.80-4.95 (1H, m), 7.00-7.15 (4H, m)

REFERENCE EXAMPLE 62

4-[(4-Chlorophenyl)methyl]-3-(β-D-glucopyranosyloxy)-5-trifluoromethyl-1H-pyrazole 4-[(4-Chlorophenyl)methyl]-3-(2,3,4,6-tetra-O-acetyl-β-D-glucopyranosyloxy)-5-trifluoromethyl-1H-pyrazole was prepared in a similar manner to that described in Reference Example 28 using 4-[(4-chlorophenyl)methyl]-1,2-dihydro-5-trifluoromethyl-3H-pyrazol-3-one instead of 1,2-dihydro-4-[(4-methylthiophenyl)methyl]-5-trifluoromethyl-3H-pyrazol-3-one. Then, the title compound was prepared in a similar manner to that described in Reference Example 37 using 4-[(4-chlorophenyl)methyl]-3-(2,3,4,6-tetra-O-acetyl-β-D-glucopyranosyloxy)-5-trifluoromethyl-1H-pyrazole instead of 4-[(4-isopropoxyphenyl)methyl]-5-methyl-3-(2,3,4,6-tetra-O-acetyl-β-D-glucopyranosyloxy)-1H-pyrazole.
$^1$H-NMR (CD$_3$OD) δ ppm:

3.20-3.40 (4H, m), 3.55-3.70 (1H, m), 3.75-3.90 (3H, m), 4.80-4.95 (1H, m), 7.10-7.25 (4H, m)

REFERENCE EXAMPLE 63

3-(β-D-Glucopyranosyloxy)-4-[(4-isopropoxyphenyl)methyl]-5-methyl-1-propylpyrazole To a suspension of 3-(β-D-glucopyranosyloxy)-4-[(4-isopropoxyphenyl)methyl]-5-methyl-1H-pyrazole (50 mg) and cesium carbonate (0.20 g) in N,N-dimethylformamide (1 mL) was added 1-iodopropane (0.036 mL) at 50° C., and the mixture was stirred overnight. Water was added to the reaction mixture, and the resulting mixture was purified by solid phase extraction on ODS (washing solvent: distilled water, eluent: methanol). The resulting semi-purified material was purified by column chromatography on silica gel (eluent: dichloromethane/methanol=8/1) to give 3-(β-D-glucopyranosyloxy)-4-[(4-isopropoxyphenyl)methyl]-5-methyl-1-propylpyrazole (28 mg).
$^1$H-NMR (CD$_3$OD) δ ppm:
0.87 (3H, t, J=7.4 Hz), 1.26 (6H, d, J=6.0 Hz), 1.65-1.80 (2H, m), 2.07 (3H, s), 3.25-3.45 (4H, m), 3.55-3.75 (3H, m), 3.75-3.95 (3H, m), 4.40-4.60 (1H, m), 5.00-5.10 (1H, m), 6.70-6.80 (2H, m), 7.00-7.10 (2H, m)

REFERENCE EXAMPLE 64

1-Ethyl-3-(β-D-glucopyranosyloxy)-4-[(4-isopropylphenyl)-methyl]-5-methylpyrazole The title compound was prepared in a similar manner to that described in Reference Example 63 using iodoethane instead of 1-iodpropane.
$^1$H-NMR (CD$_3$OD) δ ppm:
1.26 (6H, d, J=6.0 Hz), 1.29 (3H, t, J=7.2 Hz), 2.08 (3H, s), 3.25-3.45 (4H, m), 3.55-3.75 (3H, m), 3.75-3.90 (1H, m), 3.96 (2H, q, J=7.2 Hz), 4.40-4.60 (1H, m), 5.00-5.10 (1H, m), 6.70-6.80 (2H, m), 7.00-7.10 (2H, m)

REFERENCE EXAMPLE 65

1-Ethyl-3-(β-D-glucopyranosyloxy)-4-[(4-methoxyphenyl)-methyl]-5-methylpyrazole

The title compound was prepared in a similar manner to that described in Reference Example 63 using 3-(β-D-glucopyranosyloxy)-4-[(4-methoxyphenyl)methyl]-5-methyl-1H-pyrazole instead of 3-(β-D-glucopyranosyloxy)-4-[(4-iso-propoxyphenyl)methyl]-5-methyl-1H-pyrazole and using iodoethane instead of 1-iodpropane.
$^1$H-NMR (CD$_3$OD) δ ppm:
1.29 (3H, t, J=7.1 Hz), 2.07 (3H, s), 3.20-3.45 (4H, m), 3.55-3.75 (6H, m), 3.82 (1H, dd, J=2.0, 12.0 Hz), 3.90-4.05 (2H, m), 5.00-5.10 (1H, m), 6.70-6.85 (2H, m), 7.05-7.15 (2H, m)

REFERENCE EXAMPLE 66

3-(β-D-Glucopyranosyloxy)-4-[(4-methoxyphenyl)methyl]-5-methyl-1-propylpyrazole

The title compound was prepared in a similar manner to that described in Reference Example 63 using 3-(β-D-glucopyranosyloxy)-4-[(4-methoxyphenyl)methyl]-5-methyl-1H-pyrazole instead of 3-(β-D-glucopyranosyloxy)-4-[(4-iso-propoxyphenyl)methyl]-5-methyl-1H-pyrazole.
$^1$H-NMR (CD$_3$OD) δ ppm:
0.87 (3H, t, J=7.5 Hz), 1.65-1.80 (2H, m), 2.07 (3H, s), 3.35-3.45 (4H, m), 3.60-3.75 (3H, m), 3.73 (3H, s), 3.75-3.85 (1H, m), 3.85-3.95 (2H, m), 5.00-5.10 (1H, m), 6.70-6.85 (2H, m), 7.00-7.15 (2H, m)

REFERENCE EXAMPLE 67

1-Ethyl-4-[(4-ethoxyphenyl)methyl]-3-(β-D-glucopyranosyl-oxy)-5-methylpyrazole

The title compound was prepared in a similar manner to that described in Reference Example 63 using 4-[(4-ethoxyphenyl)methyl]-3-(β-D-glucopyranosyloxy)-5-methyl-1H-pyrazole instead of 3-(β-D-glucopyranosyloxy)-4-[(4-isopropoxyphenyl)methyl]-5-methyl-1H-pyrazole and using iodoethane instead of 1-iodopropane.
$^1$H-NMR (CD$_3$OD) δ ppm:
1.28 (3H, t, J=7.4 Hz), 1.34 (3H, t, J=7.2 Hz), 2.07 (3H, s), 3.25-3.45 (4H, m), 3.55-3.75 (3H, m), 3.75-3.85 (1H, m), 3.90-4.00 (4H, m), 5.00-5.10 (1H, m), 6.70-6.85 (2H, m), 7.00-7.15 (2H, m)

REFERENCE EXAMPLE 68

4-[(4-Ethoxyphenyl)methyl]-3-(β-D-glucopyranosyloxy)-5-methyl-1-propylpyrazole

The title compound was prepared in a similar manner to that described in Reference Example 63 using 4-[(4-ethoxyphenyl)methyl]-3-(β-D-glucopyranosyloxy)-5-methyl-1H-pyrazole instead of 3-(β-D-glucopyranosyloxy)-4-[(4-isopropoxyphenyl)methyl]-5-methyl-1H-pyrazole.
$^1$H-NMR (CD$_3$OD) δ ppm:
0.87 (3H, t, J=7.6 Hz), 1.34 (3H, t, J=7.1 Hz), 1.65-1.80 (2H, m), 2.07 (3H, s), 3.25-3.45 (4H, m), 3.55-3.75 (3H, m), 3.81 (1H, dd, J=2.1, 12.1 Hz), 3.85-4.05 (4H, m), 5.00-5.10 (1H, m), 6.70-6.85 (2H, m), 7.00-7.15 (2H, m)

REFERENCE EXAMPLE 69

1-Ethyl-4-[(4-ethylphenyl)methyl]-3-(β-D-glucopyranosyloxy)-5-methylpyrazole

The title compound was prepared in a similar manner to that described in Reference Example 63 using 4-[(4-ethylphenyl)methyl]-3-(β-D-glucopyranosyloxy)-5-methyl-1H-pyrazole instead of 3-(β-D-glucopyranosyloxy)-4-[(4-isopropoxyphenyl)methyl]-5-methyl-1H-pyrazole and using iodoethane instead of 1-iodopropane.
$^1$H-NMR (CD$_3$OD) δ ppm:
1.17 (3H, t, J=7.6 Hz), 1.28 (3H, t, J=7.2 Hz), 2.06 (3H, s), 2.56 (2H, q, J=7.6 Hz), 3.25-3.45 (4H, m), 3.55-3.75 (3H, m), 3.75-3.85 (1H, m), 3.90-4.00 (2H, m), 5.00-5.10 (1H, m), 7.00-7.15 (4H, m)

REFERENCE EXAMPLE 70

4-[(4-Ethylphenyl)methyl]-3-(β-D-glucopyranosyloxy)-5-methyl-1-propylpyrazole

The title compound was prepared in a similar manner to that described in Reference Example 63 using 4-[(4-ethylphenyl)methyl]-3-(β-D-glucopyranosyloxy)-5-methyl-1H-pyrazole instead of 3-(β-D-glucopyranosyloxy)-4-[(4-isopropoxyphenyl)methyl]-5-methyl-1H-pyrazole.
$^1$H-NMR (CD$_3$OD) δ ppm:

0.87 (3H, t, J=7.4 Hz), 1.17 (3H, t, J=7.6 Hz), 1.65-1.80 (2H, m), 2.06 (3H, s), 2.56 (2H, q, J=7.6 Hz), 3.25-3.45 (4H, m), 3.60-3.95 (6H, m), 5.00-5.10 (1H, m), 7.00-7.15 (4H, m)

REFERENCE EXAMPLE 71

1-Butyl-3-(β-D-glucopyranosyloxy)-4-[(4-isopropoxyphenyl)-methyl]-5-methylpyrazole The title compound was prepared in a similar manner to that described in Reference Example 63 using 1-bromobutane instead of 1-iodopropane.

$^1$H-NMR (CD$_3$OD) δ ppm:
0.92 (3H, t, J=7.4 Hz), 1.20-1.40 (8H, m), 1.60-1.75 (2H, m), 2.07 (3H, s), 3.25-3.45 (4H, m), 3.55-3.75 (3H, m), 3.81 (1H, dd, J=2.1, 12.0 Hz), 3.91 (2H, t, J=7.2 Hz), 4.45-4.55 (1H, m), 5.00-5.10 (1H, m), 6.70-6.80 (2H, m), 7.00-7.10 (2H, m)

REFERENCE EXAMPLE 72

3-(β-D-Glucopyranosyloxy)-4-[(4-isopropoxyphenyl)methyl]-1-isopropyl-5-methylpyrazole The title compound was prepared in a similar manner to that described in Reference Example 63 using 2-bromopropane instead of 1-iodopropane.

$^1$H-NMR (CD$_3$OD) δ ppm:
1.26 (6H, d, J=6.0 Hz), 1.30-1.40 (6H, m), 2.08 (3H, s), 3.15-3.45 (4H, m), 3.55-3.75 (3H, m), 3.78 (1H, dd, J=2.3, 12.0 Hz), 4.35-4.45 (1H, m), 4.45-4.55 (1H, m), 5.00-5.10 (1H, m), 6.70-6.80 (2H, m), 7.00-7.10 (2H, m)

REFERENCE EXAMPLE 73

4-[(4-Ethylthiophenyl)methyl]-1,2-dihydro-5-methyl-3H-pyrazol-3-one

To a solution of 4-ethylthiobenzyl alcohol (8.3 g) and triethylamine (6.9 mL) in tetrahydrofuran (200 mL) was added methanesulfonyl chloride (3.8 mL) at 0° C., and the mixture was stirred for 1 hour. Insoluble material was removed by filtration. The obtained solution of 4-ethylthiobenzyl methanesulfonate in tetrahydrofuran was added to a suspension of sodium hydride (60%, 2.2 g) and methyl acetoacetate (5.3 mL) in 1,2-dimethoxyethane (200 mL), and the mixture was stirred at 80° C. overnight. A saturated aqueous sodium hydrogen carbonate solution was added to the reaction mixture, and the resulting mixture was extracted with diethyl ether. The organic layer was washed with brine, dried over anhydrous magnesium sulfate, and the solvent was removed under reduced pressure. To a solution of the residue in toluene (150 mL) was added hydrazine monohydrate (7.2 mL), and the mixture was stirred at 80° C. for 1 hour. The reaction mixture was cooled to 0° C. and stirred for additional 1 hour. The resulting precipitates were collected by filtration and washed with water and hexane to give 4-[(4-ethylthiophenyl) methyl]-1,2-dihydro-5-methyl-3H-pyrazol-3-one (1.5 g).

$^1$H-NMR (DMSO-d$_6$) δ ppm:
1.19 (3H, t, J=7.3 Hz), 2.00 (3H, s), 2.90 (2H, q, J=7.3 Hz), 3.51 (2H, s), 7.05-7.15 (2H, m), 7.15-7.25 (2H, m)

REFERENCE EXAMPLE 74

4-[(4-Ethylthiophenyl)methyl]-5-methyl-3-(2,3,4,6-tetra-O-acetyl-β-D-glucopyranosyloxy)-1H-pyrazole To a suspension of 4-[(4-ethylthiophenyl)methyl]-1,2-dihydro-5-methyl-3H-pyrazol-3-one (1.6 g) and acetobromo-α-D-glucose (2.9 g) in tetrahydrofuran (30 mL) was added silver carbonate (2.1 g), and the mixture was stirred under shading the light at 60° C. overnight. The reaction mixture was purified by column chromatography on aminopropyl silica gel (eluent: tetrahydrofuran) and further column chromatography on silica gel (eluent: hexane/ethyl acetate=1/3) to give 4-[(4-ethyl-thiophenyl)methyl]-5-methyl-3-(2,3,4,6-tetra-O-acetyl-β-D-glucopyranosyloxy)-1H-pyrazole (1.4 g).

$^1$H-NMR (CDCl$_3$) δ ppm:
1.28 (3H, t, J=7.4 Hz), 1.88 (3H, s), 2.01 (3H, s), 2.03 (3H, s), 2.06 (3H, s), 2.11 (3H, s), 2.89 (2H, q, J=7.4 Hz), 3.56 (1H, d, J=15.9 Hz), 3.62 (1H, d, J=15.9 Hz), 3.80-3.90 (1H, m), 4.13 (1H, dd, J=2.3, 12.6 Hz), 4.31 (1H, dd, J=3.9, 12.6 Hz), 5.15-5.35 (3H, m), 5.55-5.65 (1H, m), 7.00-7.10 (2H, m), 7.15-7.25 (2H, m), 8.79 (1H, brs)

REFERENCE EXAMPLE 75

4-[(4-Ethylthiophenyl)methyl]-3-β-D-glucopyranosyloxy)-5-methyl-1H-pyrazole

To a solution of 4-[(4-ethylthiophenyl)methyl]-5-methyl-3-(2,3,4,6-tetra-O-acetyl-β-D-glucopyranosyloxy)-1H-pyrazole (1.3 g) in methanol (10 mL) was added sodium methoxide (28% methanol solution, 0.13 mL), and the mixture was stirred at room temperature for 1 hour. The reaction mixture was concentrated under reduced pressure, and the residue was purified by column chromatography on silica gel (eluent: dichloromethane/methanol=5/1) to give 4-[(4-ethylthiophenyl)methyl]-3-β-D-glucopyranosyloxy)-5-methyl-1H-pyrazole (0.87 g).

$^1$H-NMR (CD$_3$OD) δ ppm:
1.24 (3H, t, J=7.3 Hz), 2.06 (3H, s), 2.88 (2H, q, J=7.3 Hz), 3.30-3.45 (4H, m), 3.60-3.80 (3H, m), 3.80-3.90 (1H, m), 5.00-5.10 (1H, m), 7.10-7.30 (4H, m)

REFERENCE EXAMPLE 76

1-(Benzyloxycarbonyl)-3-β-D-glucopyranosyloxy)-4-[(4-isopropoxyphenyl)methyl]-5-methylpyrazole To a solution of 3-β-D-glucopyranosyloxy)-4-[(4-isopropoxyphenyl)methyl]-5-methyl-1H-pyrazole (1.3 g) in tetrahydrofuran (30 mL) was added N-(benzyloxycarbonyloxy)-succinimide (1.6 g), and the mixture was heated under reflux overnight. The reaction mixture was concentrated under reduced pressure, and the residue was purified by column chromatography on silica gel (eluent: dichloromethane/methanol=10/1) to give 1-(benzyloxycarbonyl)-3-(β-D-glucopyranosyloxy)-4-[(4-isopropoxyphenyl)methyl]-5-methylpyrazole (1.3 g).

$^1$H-NMR (CDCl$_3$) δ ppm:
1.27 (6H, d, J=6.3 Hz), 2.35 (3H, s), 3.45-3.70 (6H, m), 3.76 (1H, dd, J=4.5, 12.0 Hz), 3.85 (1H, dd, J=2.8, 12.0 Hz), 4.40-4.50 (1H, m), 5.30-5.40 (2H, m), 5.48 (1H, d, J=8.0 Hz), 6.70-6.80 (2H, m), 6.95-7.05 (2H, m), 7.25-7.50 (5H, m)

REFERENCE EXAMPLE 77

1-(Benzyloxycarbonyl)-3-(6-O-ethoxycarbonyl-β-D-glucopyranosyloxy)-4-[(4-isopropoxyphenyl)methyl]-5-methylpyrazole To a solution of 1-(benzyloxycarbonyl)-3-(β-D-glucopyranosyloxy)-4-[(4-isopropoxyphenyl)methyl]-5-methylpyrazole (0.20 g) in 2,4,6-trimethylpyridine (4 mL) was added ethyl chloroformate (0.092 mL), and the mixture was stirred at room temperature for 1 day. To the reaction mixture were added water and citric acid monohydrate, and the resulting mixture was extracted with ethyl acetate. The organic layer was washed with water, dried over anhydrous magnesium sulfate, and the solvent was removed under reduced pressure. The residue was purified by column chromatography on silica gel (eluent: dichloromethane/methanol=10/1) to give 1-(benzyloxycarbonyl)-3-(6-O-ethoxycarbonyl-β-D-glucopyranosyloxy)-4-[(4-isopropoxyphenyl)methyl]-5-methylpyrazole (0.17 g).

$^1$H-NMR (CD$_3$OD) δ ppm:

1.19 (3H, t, J=7.1 Hz), 1.26 (6H, d, J=6.0 Hz), 2.36 (3H, s), 3.30-3.50 (3H, m), 3.50-3.75 (3H, m), 4.10 (2H, q, J=7.1 Hz), 4.25-4.35 (1H, m), 4.35-4.45 (1H, m), 4.45-4.60 (1H, m), 5.35-5.45 (2H, m), 5.45-5.60 (1H, m), 6.70-6.85 (2H, m), 7.00-7.15 (2H, m), 7.30-7.55 (5H, m)

REFERENCE EXAMPLE 78

1-(Benzyloxycarbonyl)-4-[(4-isopropoxyphenyl)methyl]-3-(6-O-methoxycarbonyl-β-D-glucopyranosyloxy)-5-methylpyrazole The title compound was prepared in a similar manner to that described in Reference Example 77 using methyl chloroformate instead of ethyl chloroformate.

$^1$H-NMR (CDCl$_3$) δ ppm:

1.30 (6H, d, J=6.4 Hz), 2.43 (3H, s), 3.45-3.70 (6H, m), 3.78 (3H, s), 4.39 (1H, dd, J=2.2, 11.8 Hz), 4.40-4.55 (2H, m), 5.38 (2H, s), 5.40-5.50 (1H, m), 6.70-6.85 (2H, m), 7.00-7.10 (2H, m), 7.30-7.50 (5H, m)

EXAMPLE 1

3-(6-O-Ethoxycarbonyl-β-D-glucopyranosyloxy)-4-[(4-isopropoxyphenyl)methyl]-1-isopropyl-5-methylpyrazole To a solution of 3-(β-D-glucopyranosyloxy)-4-[(4-isopropoxyphenyl)methyl]-1-isopropyl-5-methylpyrazole (0.10 g) in 2,4,6-trimethylpyridine (1 mL) was added ethyl chloroformate (0.072 g), and the mixture was stirred at room temperature overnight. To the reaction mixture were added citric acid monohydrate (3.3 g) and water, and the resulting mixture was purified by ODS solid phase extraction (washing solvent: distilled water, eluent: methanol). Further purification by column chromatography on silica gel (eluent: dichloromethane/methanol=10/1) and recrystallization (recrystallization solvent: ethyl acetate/hexane=1/3) afforded 3-(6-O-ethoxycarbonyl-β-D-glucopyranosyloxy)-4-[(4-isopropoxyphenyl)methyl]-1-isopropyl-5-methylpyrazole (0.084 g).

$^1$H-NMR (CD$_3$OD) δ ppm:

1.23 (3H, t, J=7.0 Hz), 1.26 (6H, d, J=5.8 Hz), 1.30-1.40 (6H, m), 2.07 (3H, s), 3.25-3.45 (4H, m), 3.60-3.70 (2H, m), 4.12 (2H, q, J=7.0 Hz), 4.21 (1H, dd, J=5.4, 11.6 Hz), 4.34 (1H, dd, J=1.7, 11.6 Hz), 4.35-4.45 (1H, m), 4.45-4.55 (1H, m), 5.00-5.10 (1H, m), 6.70-6.80 (2H, m), 7.00-7.10 (2H, m)

EXAMPLES 2-14

The compounds listed in Table 1 were prepared from the corresponding starting material in a similar manner to that described in Example 1.

TABLE 1

| Example | R | R$^2$ | Q |
|---|---|---|---|
| 2 | Methyl | Methoxy | Methyl |
| 3 | Methyl | Methylthio | Trifluoromethyl |
| 4 | Ethyl | Methylthio | Trifluoromethyl |
| 5 | Propyl | Methylthio | Trifluoromethyl |
| 6 | Propyl | Isopropoxy | Methyl |
| 7 | Ethyl | Isopropoxy | Methyl |
| 8 | Ethyl | Methoxy | Methyl |
| 9 | Propyl | Methoxy | Methyl |
| 10 | Ethyl | Ethoxy | Methyl |
| 11 | Propyl | Ethoxy | Methyl |
| 12 | Ethyl | Ethyl | Methyl |
| 13 | Propyl | Ethyl | Methyl |
| 14 | Butyl | Isopropoxy | Methyl |

EXAMPLE 15

4-[(4-Isopropoxyphenyl)methyl]-1-isopropyl-3-(6-O-methoxycarbonyl-β-D-glucopyranosyloxy)-5-methylpyrazole The title compound was prepared in a similar manner to that described in Example 1 using methyl chloroformate instead of ethyl chloroformate.

$^1$H-NMR (CD$_3$OD) δ ppm:

1.26 (6H, d, J=6.1 Hz), 1.30-1.40 (6H, m), 2.07 (3H, s), 3.25-3.45 (4H, m), 3.60-3.70 (2H, m), 3.71 (3H, s), 4.22 (1H, dd, J=5.2, 11.7 Hz), 4.35 (1H, dd, J=2.1, 11.7 Hz), 4.35-4.45 (1H, m), 4.45-4.60 (1H, m), 5.00-5.10 (1H, m), 6.70-6.80 (2H, m), 7.00-7.10 (2H, m)

EXAMPLE 16

3-(6-O-Isobutyloxycarbonyl-β-D-glucopyranosyloxy)-4-[(4-isopropoxyphenyl)methyl]-1-isopropyl-5-methylpyrazole The title compound was prepared in a similar manner to that described in Example 1 using isobutyl chloroformate instead of ethyl chloroformate.

$^1$H-NMR (CD$_3$OD) δ ppm:

0.90 (6H, d, J=6.7 Hz), 1.26 (6H, d, J=5.9 Hz), 1.30-1.40 (6H, m), 1.80-2.00 (1H, m), 2.07 (3H, s), 3.25-3.50 (4H, m), 3.60-3.70 (2H, m), 3.80-3.90 (2H, m), 4.21 (1H, dd, J=5.2, 11.5 Hz), 4.36 (1H, dd, J=1.8, 11.5 Hz), 4.35-4.45 (1H, m), 4.45-4.55 (1H, m), 5.00-5.10 (1H, m), 6.70-6.80 (2H, m), 7.00-7.10 (2H, m)

EXAMPLE 17

4-[(4-Isopropoxyphenyl)methyl]-1-isopropyl-5-methyl-3-(6-O-propionyl-β-D-glucopyranosyloxy)pyrazole To a solution of 3-(β-D-glucopyranosyloxy)-4-[(4-isopropoxyphenyl)methyl]-1-isopropyl-5-methylpyrazole (0.10 g) in 2,4,6-trimethylpyridine (1 mL) was added propionyl chloride (0.072 g) at 0° C., and the mixture was stirred for hours. To the reaction mixture were added citric acid monohydrate (3.3 g) and water, and the resulting mixture was purified by ODS solid phase extraction (washing solvent: distilled water, eluent: methanol). Further purification by column chromatography on silica gel (eluent: dichloromethane/methanol=10/1) afforded 4-[(4-isopropoxyphenyl)methyl]-1-isopropyl-5-methyl-3-(6-O-propionyl-β-D-glucopyranosyloxy)pyrazole (0.074 g)

$^1$H-NMR (CD$_3$OD) δ ppm:
1.05 (3H, t, J=7.5 Hz), 1.26 (6H, d, J=5.9 Hz), 1.30-1.40 (6H, m), 2.07 (3H, s), 2.27 (2H, q, J=7.5 Hz), 3.25-3.45 (4H, m), 3.60-3.70 (2H, m), 4.18 (1H, dd, J=5.6, 11.8 Hz), 4.30 (1H, dd, J=2.2, 11.8 Hz), 4.35-4.45 (1H, m), 4.45-4.55 (1H, m), 5.00-5.10 (1H, m), 6.70-6.80 (2H, m), 7.00-7.10 (2H, m)

EXAMPLE 18

3-(6-O-Acetyl-β-D-glucopyranosyloxy)-4-[(4-isopropoxyphenyl)methyl]-1-isopropyl-5-methylpyrazole The title compound was prepared in a similar manner to that described in Example 17 using acetyl chloride instead of propionyl chloride.

$^1$H-NMR (CD$_3$OD) δ ppm:
1.26 (6H, d, J=6.4 Hz), 1.30-1.40 (6H, m), 1.98 (3H, s), 2.08 (3H, s), 3.25-3.45 (4H, m), 3.60-3.70 (2H, m), 4.16 (1H, dd, J=5.6, 11.8 Hz), 4.29 (1H, dd, J=2.0, 11.8 Hz), 4.35-4.55 (2H, m), 5.00-5.10 (1H, m), 6.70-7.80 (2H, m), 7.00-7.10 (2H, m)

EXAMPLE 19

3-(6-O-Butyryl-β-D-glucopyranosyloxy)-4-[(4-isopropoxyphenyl)methyl]-1-isopropyl-5-methylpyrazole The title compound was prepared in a similar manner to that described in Example 17 using butyryl chloride instead of propionyl chloride.

$^1$H-NMR (CD$_3$OD) δ ppm:
0.88 (3H, t, J=7.4 Hz), 1.26 (6H, d, J=6.0 Hz), 1.30-1.40 (6H, m), 1.50-1.65 (2H, m), 2.07 (3H, s), 2.15-2.30 (2H, m), 3.25-3.50 (4H, m), 3.60-3.70 (2H, m), 4.17 (1H, dd, J=5.7, 11.9 Hz), 4.31 (1H, dd, J=2.0, 11.9 Hz), 4.30-4.55 (2H, m), 5.00-5.10 (1H, m), 6.70-6.80 (2H, m), 7.00-7.10 (2H, m)

EXAMPLE 20

4-[(4-Isopropoxyphenyl)methyl]-1-isopropyl-5-methyl-3-(6-O-pivaroyl-β-D-glucopyranosyloxy)pyrazole The title compound was prepared in a similar manner to that described in Example 17 using pivaloyl chloride instead of propionyl chloride.

$^1$H-NMR (CD$_3$OD) δ ppm:
1.10 (9H, s), 1.26 (6H, d, J=6.1 Hz), 1.30-1.40 (6H, m), 2.06 (3H, s), 3.30-3.45 (4H, m), 3.60-3.70 (2H, m), 4.16 (1H, dd, J=5.8, 11.7 Hz), 4.30 (1H, dd, J=2.0, 11.7 Hz), 4.30-4.55 (2H, m), 5.05-5.15 (1H, m), 6.70-6.80 (2H, m), 7.00-7.10 (2H, m)

EXAMPLE 21

1-Ethoxycarbonyl-3-(6-O-ethoxycarbonyl-β-D-glucopyranosyloxy)-4-[(4-ethylthiophenyl)methyl]-5-methylpyrazole To a solution of 4-[(4-ethylthiophenyl)methyl]-3-(β-D-glucopyranosyloxy)-5-methyl-1H-pyrazole (0.03 g) in 2,4,6-trimethylpyridine (0.5 mL) was added ethyl chloroformate (0.021 mL), and the mixture was stirred at room temperature overnight. To the reaction mixture was added 10% aqueous citric acid solution, and the resulting mixture was extracted with ethyl acetate. The organic layer was dried over anhydrous magnesium sulfate, and the solvent was removed under reduced pressure. The residue was purified by preparative thin layer chromatography on silica gel (eluent: dichloromethane/methanol=10/1) to give 1-ethoxycarbonyl-3-(6-O-ethoxycarbonyl-β-D-glucopyranosyloxy)-4-[(4-ethylthiophenyl)methyl]-5-methylpyrazole (0.023 g).

$^1$H-NMR (CD$_3$OD) δ ppm:
1.15-1.30 (6H, m), 1.39 (3H, t, J=7.1 Hz), 2.37 (3H, s), 2.87 (2H, q, J=7.3 Hz), 3.35-3.50 (3H, m), 3.60-3.80 (3H, m), 4.12 (2H, q, J=7.1 Hz), 4.29 (1H, dd, J=5.3, 11.9 Hz), 4.35-4.50 (3H, m), 5.50-5.60 (1H, m), 7.10-7.25 (4H, m)

EXAMPLES 22-43

The compounds listed in Table 2 were prepared from the corresponding starting material in a similar manner to that described in Example 21.

TABLE 2

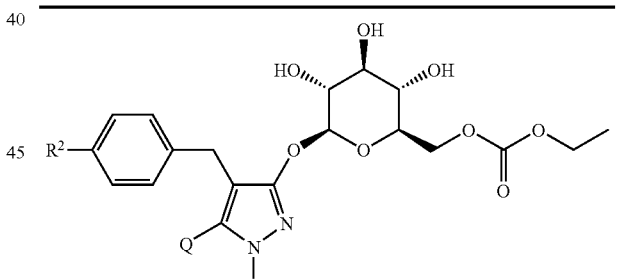

| Example | R | R² | Q |
|---|---|---|---|
| 22 | Ethoxycarbonyl | Isopropoxy | Methyl |
| 23 | Ethoxycarbonyl | Propyl | Methyl |
| 24 | Ethoxycarbonyl | Isobutyl | Methyl |
| 25 | Ethoxycarbonyl | Propoxy | Methyl |
| 26 | Ethoxycarbonyl | Ethoxy | Methyl |
| 27 | Ethoxycarbonyl | Trifluoromethyl | Methyl |
| 28 | Ethoxycarbonyl | tert-Butyl | Methyl |
| 29 | Ethoxycarbonyl | Butoxy | Methyl |
| 30 | Ethoxycarbonyl | Methylthio | Methyl |
| 31 | Ethoxycarbonyl | Methylthio | Ethyl |
| 32 | Ethoxycarbonyl | Isopropyl | Methyl |
| 33 | Ethoxycarbonyl | Methylthio | Trifluoromethyl |
| 34 | Ethoxycarbonyl | Hydrogen | Trifluoromethyl |
| 35 | Ethoxycarbonyl | Methoxy | Trifluoromethyl |
| 36 | Ethoxycarbonyl | Methoxy | Methyl |
| 37 | Ethoxycarbonyl | Hydrogen | Methyl |
| 38 | Ethoxycarbonyl | Methyl | Methyl |

TABLE 2-continued

| 39 | Ethoxycarbonyl | Ethyl | Methyl |
| 40 | Ethoxycarbonyl | Methyl | Trifluoromethyl |
| 41 | Ethoxycarbonyl | Ethyl | Trifluoromethyl |
| 42 | Ethoxycarbonyl | Isopropyl | Trifluoromethyl |
| 43 | Ethoxycarbonyl | Chlorine | Trifluoromethyl |

EXAMPLE 44

3-(6-O-Ethoxycarbonyl-β-D-glucopyranosyloxy)-1-(ethoxycarbonyloxymethyl)-4-[(4-methylthiophenyl)methyl]-5-methylpyrazole To a solution of 3-(β-D-glucopyranosyloxy)-5-methyl-4-[(4-methylthiophenyl)methyl]-1H-pyrazole (0.11 g) in water (0.5 mL) and ethanol (0.1 mL) was added formaldehyde (37% aqueous solution, 0.068 mL), and the mixture was stirred at 40° C. for 3 days. To the reaction mixture were added tetrahydrofuran and anhydrous magnesium sulfate, and the resulting insoluble material was removed by filtration. The solvent of the filtrate was removed under reduced pressure. The residue was dissolved in 2,4,6-trimethylpyridine (1 mL). Ethyl chloroformate (0.099 g) was added to the solution, and the mixture was stirred at room temperature overnight. To the reaction mixture were added citric acid monohydrate (4 g) and water, and the resulting mixture was purified by ODS solid phase extraction (washing solvent: 10% aqueous citric acid solution, distilled water, eluent: methanol). Further purification by column chromatography on silica gel (eluent: dichloromethane/methanol=15/1) afforded 3-(6-O-ethoxycarbonyl-β-D-glucopyranosyloxy)-1-(ethoxycarbonyloxymethyl)-4-[(4-methylthiophenyl)methyl]-5-methylpyrazole (0.058 g).

$^1$H-NMR (CD$_3$OD) δ ppm:

1.23 (3H, t, J=7.1 Hz), 1.26 (3H, t, J=7.1 Hz), 2.18 (3H, s), 2.42 (3H, s), 3.30-3.45 (3H, m), 3.50-3.60 (1H, m), 3.63 (1H, d, J=16.0 Hz), 3.70 (1H, d, J=16.0 Hz), 4.13 (2H, q, J=7.1 Hz), 4.18 (2H, q, J=7.1 Hz), 4.28 (1H, dd, J=4.8, 11.7 Hz), 4.39 (1H, dd, J=2.0, 11.7 Hz), 5.25-5.35 (1H, m), 5.80-5.95 (2H, m), 7.10-7.20 (4H, m)

EXAMPLE 45

1-Acetyl-4-[(4-ethylthiophenyl)methyl]-3-(β-D-glucopyranosyloxy)-5-methylpyrazole To a solution of 4-[(4-ethylthiophenyl)methyl]-3-(β-D-glucopyranosyloxy)-5-methyl-1H-pyrazole (0.41 g) in tetrahydrofuran (10 mL) were added acetic acid (0.11 mL) and acetic anhydride (0.18 mL), and the mixture was stirred at room temperature overnight. The reaction mixture was concentrated under reduced pressure, and diethyl ether was added to the residue. The resulting precipitated crystal was collected by filtration to give 1-acetyl-4-[(4-ethylthiophenyl)methyl]-3-(β-D-glucopyranosyloxy)-5-methylpyrazole (0.36 g).

$^1$H-NMR (CD$_3$OD) δ ppm:

1.24 (3H, t, J=7.3 Hz), 2.43 (3H, s), 2.54 (3H, s), 2.89 (2H, q, J=7.3 Hz), 3.30-3.50 (4H, m), 3.60-3.75 (3H, m), 3.80-3.90 (1H, m), 5.45-5.55 (1H, m), 7.10-7.30 (4H, m)

EXAMPLE 46

1-Acetyl-3-(6-O-ethoxycarbonyl-β-D-glucopyranosyloxy)-4-[(4-ethylthiophenyl)methyl]-5-methylpyrazole To a solution of 1-acetyl-4-[(4-ethylthiophenyl)-methyl]-3-(β-D-glucopyranosyloxy)-5-methylpyrazole (0.03 g) in 2,4,6-trimethylpyridine (0.5 mL) was added ethyl chloroformate (0.012 mL), and the mixture was stirred at room temperature overnight. To the reaction mixture was added 10% aqueous citric acid solution (5 mL), and the resulting mixture was stirred at room temperature overnight. The resulting precipitatse were collected by filtration and washed with 10% aqueous citric acid solution and water to give 1-acetyl-3-(6-O-ethoxycarbonyl-β-D-glucopyranosyloxy)-4-[(4-ethylthiophenyl)methyl]-5-methylpyrazole (0.020 g).

$^1$H-NMR (CD$_3$OD) δ ppm:

1.20 (3H, t, J=7.2 Hz), 1.24 (3H, t, J=7.4 Hz), 2.41 (3H, s), 2.55 (3H, s), 2.88 (2H, q, J=7.4 Hz), 3.30-3.40 (1H, m), (2H, m), 3.50-3.65 (1H, m), 3.65 (1H, d, J=15.8 Hz), 3.72 (1H, d, J=15.8 Hz), 4.05-4.15 (2H, m), 4.27 (1H, dd, J=6.3, 11.7 Hz), 4.42 (1H, dd, J=2.0, 11.7 Hz), (1H, m), 7.10-7.30 (4H, m)

EXAMPLE 47

3-(6-O-Ethoxycarbonyl-β-D-glucopyranosyloxy)-4-[(4-isopropoxyphenyl)methyl]-5-methyl-1H-pyrazole To a solution of 1-(benzyloxycarbonyl)-3-(6-O-ethoxycarbonyl-β-D-glucopyranosyloxy)-4-[(4-isopropoxyphenyl)-methyl]-5-methylpyrazole (0.17 g) in tetrahydrofuran (4 mL) was added 10% palladium-carbon powder, and the mixture was stirred under hydrogen atmosphere at room temperature for 3 hours. The resulting insoluble material was removed by filtration, and the solvent of the filtrate was removed under reduced pressure. The residue was purified by column chromatography on silica gel (eluent: dichloromethane/methanol=10/1) to give 3-(6-O-ethoxycarbonyl-β-D-glucopyranosyloxy)-4-[(4-isopropoxyphenyl)methyl]-5-methyl-1H-pyrazole (0.10 g).

$^1$H-NMR (CD$_3$OD) δ ppm:

1.23 (3H, t, J=7.1 Hz), 1.26 (6H, d, J=6.0 Hz), 2.04 (3H, s), 3.30-3.55 (4H, m), 3.61 (1H, d, J=15.9 Hz), 3.67 (1H, d, J=15.9 Hz), 4.12 (2H, q, J=7.1 Hz), 4.27 (1H, dd, J=4.9, 11.7 Hz), 4.38 (1H, dd, J=2.0, 11.7 Hz), 4.45-4.60 (1H, m), 5.10-5.20 (1H, m), 6.70-6.80 (2H, m), 7.00-7.15 (2H, m)

EXAMPLE 48

4-[(4-Isopropoxyphenyl)methyl]-3-(6-O-methoxycarbonyl-β-D-glucopyranosyloxy)-5-methyl-1H-pyrazole The title compound was prepared in a similar manner to that described in Example 47 using 1-(benzyloxycarbonyl)-4-[(4-isopropoxyphenyl)methyl]-3-(6-O-methoxycarbonyl-β-D-glucopyranosyloxy)-5-methylpyrazole instead of 1-(benzyloxycarbonyl)-3-(6-O-ethoxycarbonyl-β-D-glucopyranosyloxy)-4-[(4-isopropoxyphenyl)methyl]-5-methylpyrazole.

$^1$H-NMR (CD$_3$OD) δ ppm:

1.26 (6H, d, J=5.9 Hz), 2.04 (3H, s), 3.30-3.55 (4H, m), 3.61 (1H, d, J=15.9 Hz), 3.67 (1H, d, J=15.9 Hz), 3.72 (3H, s), 4.28 (1H, dd, J=5.2, 11.7 Hz), 4.39 (1H, dd, J=1.8, 11.7 Hz), 4.45-4.55 (1H, m), 5.05-5.15 (1H, m), 6.70-6.80 (2H, m), 7.00-7.15 (2H, m)

TEST EXAMPLE 1

Assay for Inhibitory Effect on Human SGLT2 Activity

1) Construction of the Plasmid Vector Expressing Human SGLT2

Preparation of the cDNA Library for PCR Amplification was performed by reverse transcription of a total RNA deprived from human kidney (Ori gene) with oligo dT as the primer, using SUPERSCRIPT Preamplification System (Gibco-BRL: LIFE TECHNOLOGIES). The DNA fragment coding for human SGLT2 was amplified by the PCR reaction, in which the human kidney cDNA library described above was used as the template and the following oligo nucleotides 0702F and 0712R, presented as sequence number 1 and 2 respectively, were used as the primers. The amplified DNA fragment was ligated into pCR-Blunt (Invitrogen), a vector for cloning, according to standard method of the kit. The *Escherichia coli* HB101 was transformed according to usual method and then selection of the transformants was performed on the LB agar medium containing 50 plasmid DNA was extracted and purified from the one of the transformants, amplifying of the DNA fragment coding for human SGLT2 was performed by the PCR reaction, in which the following oligo nucleotides 0714F and 0715R, presented as sequence number 3 and 4 respectively, were used as the primers. The amplified DNA fragment was digested with restriction enzymes, Xho I and Hind III, and then purified with Wizard Purification System (Promega). This purified DNA fragment was inserted at into the corresponding restriction sites of pcDNA3.1 (−) Myc/His-B (Invitrogen), a vector for expressing of fusion protein. The *Escherichia coli* HB101 was transformed according to usual method and then selection of the transformant was performed on the LB agar medium containing 100 plasmid DNA was extracted and purified from this transformant, the base sequence of the DNA fragment inserted at the multi-cloning sites of the vector pcDNA3.1 (−) Myc/His-B was analyzed. This clone had a single base substitution (ATC which codes for the isoleucine-433 was substituted by GTC) compared with the human SGLT2 reported by Wells et al (Am. J. Physiol., Vol. 263, pp. 459-465 (1992)). Sequentially, a clone in which valine is substituted for isoleucine-433 was obtained. This plasmid vector expressing human SGLT2 in which the peptide presented as sequence number 5 is fused to the carboxyl terminal alanine residue was designated KL29.

```
Sequence Number 1 ATGGAGGAGCACACAGAGGC

Sequence Number 2 GGCATAGAAGCCCCAGAGGA

Sequence Number 3 AACCTCGAGATGGAGGAGCACACAGAGGC

Sequence Number 4 AACAAGCTTGGCATAGAAGCCCCAGAGGA

Sequence Number 5 KLGPEQKLISEEDLNSAVDHHHHHH
```

2) Preparation of the Cells Expressing Transiently Human SGLT2

KL29, the plasmid coding human SGLT2, was transfected into COS-7 cells (RIKEN CELL BANK RCB0539) by electroporation. Electroporation was performed with GENE PULSER II (Bio-Rad Laboratories) under the condition: 0.290 kV, 975 μF, 2×10$^6$ cells of COS-7 cell and 20 μg of KL29 in 500 μL of OPTI-MEM I medium (Gibco-BRL: LIFE TECHNOLOGIES) in the 0.4 cm type cuvette. After the gene transfer, the cells were harvested by centrifugation and resuspended with OPTI-MEM I medium (1 mL/cuvette). To each well in 96-wells plate, 125 μL of this cell suspension was added. After overnight culture at 37° C. under 5% $CO_2$, 125 μL of DMEM medium which is containing 10% of fetal bovine serum (Sanko Jyunyaku), 100 units/mL sodium penicillin G (Gibco-BRL: LIFE TECHNOLOGIES), 100 μg/mL streptomycin sulfate (Gibco-BRL: LIFE TECHNOLOGIES) was added to each well. These cells were cultured until the next day and then they were used for the measurement of the inhibitory activity against the uptake of methyl-α-D-glucopyranoside.

3) Measurement of the Inhibitory Activity Against the Uptake of Methyl-α-D-glucopyranoside After a test compounds was dissolved in dimethyl sulfoxide and diluted with the uptake buffer (a pH 7.4 buffer containing 140 mM sodium chloride, 2 mM potassium chloride, 1 mM calcium chloride, 1 mM magnesium chloride, 5 mM methyl-α-D-glucopyranoside, 10 mM 2-[4-(2-hydroxyethyl)-1-piperazinyl]ethane sulfonic acid and 5 mM tris(hydroxymethyl)aminomethane), each diluent was used as test sample for measurement of the inhibitory activity. After removal of the medium of the COS-7 cells expressing transiently human SGLT2, to each well 200 μL of the pretreatment buffer (a pH 7.4 buffer containing 140 mM choline chloride, 2 mM potassium chloride, 1 mM calcium chloride, 1 mM magnesium chloride, 10 mM 2-[4-(2-hydroxyethyl)-1-piperazinyl]ethane sulfonic acid and 5 mM tris(hydroxymethyl)aminomethane) was added, and the cells were incubated at 37° C. for 10 minutes. After the pretreatment buffer was removed, 200 μL of the same buffer was added again, and the cells were incubated at 37° C. for 10 minutes. The buffer for measurement was prepared by adding of 7 μL of methyl-α-D-(U-14C)glucopyranoside(Amersham Pharmacia Biotech) to 525 μL of the prepared test sample. For the control, the buffer for measurement without test compound was prepared. For estimate of the basal uptake in the absence of test compound and sodium, the buffer for measurement of the basal uptake, which contains 140 mM choline chloride in place of sodium chloride, was prepared similarly. After the pretreatment buffer was removed, 75 μL of the each buffer for measurement was added to each well, the cells were incubated at 37° C. for 2 hours. After the buffer for measurement was removed, 200 μL of the washing buffer (a pH 7.4 buffer containing 140 mM choline chloride, 2 mM potassium chloride, 1 mM calcium chloride, 1 mM magnesium chloride, 10 mMmethyl-α-D-glucopyranoside, 10 mM 2-[4-(2-hydroxyethyl)-1-piperazinyl]ethane sulfonic acid and 5 mM tris(hydroxymethyl)aminomethane) was added to each well and immediately removed. After two additional washing, the cells were solubilized by addition of 75 μL of 0.2 mol/L sodium hydroxide to each well. After the cell lysates were transferred to the PicoPlate (Packard) and 150 μL of MicroScint-40 (Packard) was added to each well, the radioactivity was measured with microplate scintillation counter TopCount (Packard). The difference in uptake was obtained as 100% value by subtracting the radioactivity in the basal uptake from that in control and then the concentrations at which 50% of uptake were inhibited ($IC_{50}$) were calculated from the concentration-inhibition curve by least square method. The results are shown in the following Table 3.

TABLE 3

| Test compound | $IC_{50}$ value (nM) |
|---|---|
| Reference Example 37 | 181 |
| Reference Example 38 | 441 |
| Reference Example 39 | 346 |

TABLE 3-continued

| Test compound | IC$_{50}$ value (nM) |
|---|---|
| Reference Example 40 | 702 |
| Reference Example 41 | 185 |
| Reference Example 45 | 84 |
| Reference Example 46 | 509 |
| Reference Example 47 | 441 |
| Reference Example 48 | 679 |
| Reference Example 50 | 415 |
| Reference Example 51 | 383 |
| Reference Example 54 | 835 |
| Reference Example 57 | 280 |
| Reference Example 58 | 190 |
| Reference Example 60 | 634 |
| Reference Example 72 | 369 |
| WAY-123783 | >100000 |

TEST EXAMPLE 2

Assay for Oral Absorbability

1) Preparation of the Samples for Measurement of the Drug Concentration After Intravenous Injection to the Tail Vein As experimental animal, overnight fasted SD rats (CLEA JAPAN, INC., male, 5 weeks of age, 140-170 g) were used. Sixty mg of a test compound was dissolved by adding of 1.8 mL of ethanol, 7.2 mL of polyethylene glycol 400 and 9 mL of saline, and then 3.3 mg/mL solution was prepared. The body weights of rats were measured and the solution of the test compound was intravenously injected to the tail vein of unanesthetized rats at the dose of 3 mL/kg (10 mg/kg). The intravenous injection to the tail was performed with 26 G injection needle and 1 mL syringe. The sampling times for collection of blood were 2, 5, 10, 20, 30, 60 and 120 minutes after the intravenous injection to the tail. The blood was centrifuged and the plasma was used as the sample for measurement of the drug concentration in plasma.

2) Preparation of the Samples for Measurement of the Drug Concentration After Oral Administration As experimental animal, overnight fasted SD rats (CLEA JAPAN, INC., male, 5 weeks of age, 140-170 g) were used. A test compound was suspended or dissolved in 0.5% sodium carboxymethylcellulose solution at the concentration of 1 mg/mL of active form. When homogenous suspension was not obtained in this condition, the test compound was dissolved in ethanol at the concentration of 100 mg/mL of active form and then suspension was obtained by adding this solution to 99 times volumes of 0.5% sodium carboxymethylcellulose solution. After the body weights of rats were measured, the liquid containing test compound described above was orally administered at the dose of 10 mL/kg (10 mg/kg as active form). The oral administration was performed with gastric tube for rat and 2.5 mL syringe. The sampling times for collection of blood were 15, 30, 60, 120 and 240 minutes after the oral administration. The blood was centrifuged and the plasma was used as the sample for measurement of the drug concentration in plasma.

3) Measurement of Drug Concentration

Method A

To 0.1 mL of the plasma obtained in 1) and 2) described above, an adequate amount of an adequate internal standard material was added according to usual method and then deproteinization was performed by adding of 1 mL of methanol. After centrifugation, the methanol phase was evaporated to dryness under a stream of nitrogen. The residue was dissolved in 300 µL of the mobile phase and 30 µL aliquot of the solution was injected into HPLC. The drug concentration in plasma was measured by HPLC method under the condition as follows. To 0.1 mL of the blank plasma an adequate internal standard and various concentrations of corresponding active form of the compound were adequately added according to usual method, similar operating described above was done and then the standard curve was prepared.

Column: Develosil ODS-UG-5 (4.6×250 mm)

Mobile phase: acetonitrile/10 mM phosphate buffer (pH 3.0) =22:78 (v/v)

Column temperature: 50° C.

Flow rate: 1.0 mL/minute

Wavelength for measurement: UV 232 nm

Method B

To 50 µL of the plasma obtained in 1) and 2) described above, an adequate amount of an adequate internal standard material was added according to usual method and 100 µl of distilled water was added, and then extraction was performed by adding of 1 mL of diethyl ether. After centrifugation, the diethyl ether phase was evaporated to dryness under a stream of nitrogen. The residue was dissolved in 200 µL of the mobile phase and 10 µL aliquot of the solution was injected into LC-MS/MS. The drug concentration in plasma was measured by LC-MS/MS method under the condition as follows. To 50 µL of the blank plasma an adequate internal standard and various concentrations of corresponding active form of compound were adequately added according to usual method, similar operating described above was done and then the standard curve was prepared

LC

Column: Symmetry C$_8$ (2.1×20 mm)

Mobile phase: acetonitrile/0.1% acetic acid solution=65:35 (v/v)

Column temperature: 40° C.

Flow rate: 0.2 mL/minute

MS/MS

Ionization method: ESI (Turbo Ion Spray), positive ion detection mode

Ion spray voltage: 5000 V

Heater gas temperature: 450° C.

Collision energy: 17.5 V

Multiplier voltage: 2300 V

Flow rate of turbo ion spray gas: 7000 mL/min

Nebulizer gas: 11 BIT

Curtain gas: 11 BIT

Collision gas: 4 BIT

Each area under the plasma concentration-time curve by intravenous injection to the tail vein and oral administration of test compound was estimated with WinNonlin Standard made by Pharsight Corporation from the plasma concentrations at each time obtained from method A and B and then the bioavailability (%) was calculated based on the following formula. The results are shown in the following Table 4.

Bioavailability(%)=(Area under the Plasma Concentration–Time Curve by Oral Administration/Area under the Plasma Concentration–Time Curve by Intravenous Injection to the Tail Vein)×100

TABLE 4

| Test compound | Method | Bioavailability(%) |
|---|---|---|
| Example 1 | B | 27 |
| Example 15 | B | 27 |
| Example 16 | B | 32 |
| Example 47 | A | 15 |
| Example 48 | A | 11 |
| Reference Example 37 | A | 0 |

TEST EXAMPLE 3

Assay for the Facilitatory Effect on Urinary Glucose Excretion

As experimental animal, overnight fasted SD rats (Japan SLC. Inc., male, 7 weeks of age, 202-221 g) were used. A Test compound was suspended in 0.5% sodium carboxymethylcellulose solution at the concentration of 2 mg/mL. When homogenous suspension was not obtained in this condition, the test compound was dissolved in ethanol at the concentration of 200 mg/mL of active form and then 2 mg/mL suspension was obtained by adding this solution to 99 times volumes of 0.5% sodium carboxymethylcellulose solution. A part of this suspension was diluted with 0.5% sodium carboxymethylcellulose solution and then 0.6 and 0.2 mg/mL suspensions were prepared. After the body weights of rats were measured, the test suspension was orally administered at the dose of 5 mL/kg (1, 3 and 10 mg/kg). For control, just only 0.5% sodium carboxymethylcellulose solution was orally administered at the dose of 5 mL/kg. Immediately after this oral administration, 400 g/L glucose solution was orally administered at the dose of 5 mL/kg (2 g/kg). The oral administration was performed with gastric tube for rat and 2.5 mL syringe. The head count in one group was 3. Collection of urine was performed in metabolic cage after the glucose administration was finished. The sampling time for collection of urine was 24 hours after the glucose administration. After collection of urine was finished, the urine volume was recorded and the urinary glucose concentration was measured. The glucose concentration was measured with a kit for laboratory test: Glucose B-Test WAKO (Wako Pure Chemical Industries, Ltd.). The amount of urinary glucose excretion in 24 hours per 200 g of body weight was calculated from urine volume, urinary glucose concentration and body weight. The results are shown in the following Table 5.

TABLE 5

| Test compound | Dose (mg/kg) | Amount of Urinary Glucose Excretion (mg/24 hours · 200 g body weight) |
|---|---|---|
| Example 1 | 1 | 1.6 |
| | 3 | 28.3 |
| | 10 | 127.5 |
| Example 15 | 1 | 1.7 |
| | 3 | 36.8 |
| | 10 | 167.3 |

TEST EXAMPLE 4

Acute Toxicity Test

After 4 week old male ICR mice (Japan SLC. Inc., 20-25 g, 5 animals in each group) were fasted for 4 hours, the suspension (200 mg/mL) prepared by adding of 0.5% sodium carboxymethylcellulose solution to the test compound was orally administered at the dose of 10 mL/kg (2000 mg/kg). Observation was performed until 24 hours after the administration. The results are shown in the following Table 6.

TABLE 6

| Test compound | Death number |
|---|---|
| Example 48 | 0/5 |

INDUSTRIAL APPLICABILITY

The glucopyranosyloxypyrazole derivatives represented by the above general formula (I) of the present invention or pharmaceutically acceptable salts thereof have an improved oral absorption. In addition, they show an excellent hypoglycemic effect by excreting excess glucose into the urine through preventing the reabsorption of glucose at the kidney because they are converted into glucopyranosyloxypyrazole derivatives represented by the above general formula (II) as their active forms in vivo and exhibit a potent inhibitory activity in human SGLT2. Therefore, the present invention can provide agents for the prevention or treatment of a disease associated with hyperglycemia such as diabetes, diabetic complications, obesity or the like, which are also suitable as oral formulations.

[Sequence Listing Free Text]
Sequence Number 1: Synthetic DNA primer
Sequence Number 2: Synthetic DNA primer
Sequence Number 3: Synthetic DNA primer
Sequence Number 4: Synthetic DNA primer
Sequence Number 5: Peptide fused to the carboxyl terminal alanine residue of human SGLT2

The invention claimed is:

1. A method for the treatment of a disease associated with hyperglycemia, which comprises administering to a patient in need thereof an effective amount of a glucopyranosyloxypyrazole derivative of the following general formula or a pharmaceutically acceptable salt thereof:

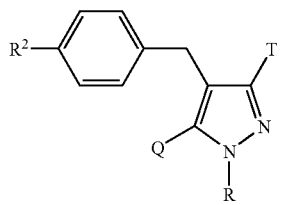

wherein R represents a hydrogen atom, a lower alkyl group or a group forming a prodrug; one of Q and T represents a group represented by the general formula:

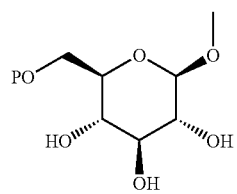

wherein P represents a hydrogen atom or a group forming a prodrug, while the other represents a lower alkyl group or a halo(lower alkyl) group; $R^2$ represents a hydrogen atom, a lower alkyl group, a lower alkoxy group, a lower alkylthio group, a halo(lower alkyl) group or a halogen atom; and with the proviso that P does not represent a hydrogen atom when R represents a hydrogen atom or a lower alkyl group.

2. A method for the treatment as claimed in claim 1 wherein the disease associated with hyperglycemia is diabetes or diabetic complications.

3. A method for the treatment as claimed in claim 1 wherein the disease associated with hyperglycemia is obesity.

4. A method for the treatment as claimed in claim 1 wherein the disease associated with hyperglycemia is hypertension.

5. A method for the treatment as claimed in claim 1, wherein said compound is 3-(6-O-ethoxycarbonyl-β-D-glucopyranosyloxy)-4-[(4-isopropoxyphenyl)methyl]-1-isopropyl-5-methylpyrazole or a pharmaceutically acceptable salt thereof.

6. A method for the treatment as claimed in claim 2, wherein said compound is 3-(6-O-ethoxycarbonyl-β-D-glucopyranosyloxy)-4-[(4-isopropoxyphenyl)methyl]-1-isopropyl-5-methylpyrazole or a pharmaceutically acceptable salt thereof.

7. A method for the treatment as claimed in claim 3, wherein said compound is 3-(6-O-ethoxycarbonyl-β-D-glucopyranosyloxy)-4-[(4-isopropoxyphenyl)methyl]-1-isopropyl-5-methylpyrazole or a pharmaceutically acceptable salt thereof.

8. A method for the treatment as claimed in claim 4, wherein said compound is 3-(6-O-ethoxycarbonyl-β-D-glucopyranosyloxy)-4-[(4-isopropoxyphenyl)methyl]-1-isopropyl-5-methylpyrazole or a pharmaceutically acceptable salt thereof.

9. A method for the treatment as claimed in any one of claims 1, 2, 3, 4-7 or 8 wherein said compound or pharmaceutically acceptable salt thereof is orally administered.

10. A method for increasing the amount of urinary glucose excretion, which comprises administering to a subject in need thereof an amount of a glucopyranosyloxypyrazole derivative of the following general formula, or a pharmaceutically acceptable salt thereof, effective to increase the amount of urinary glucose excretion in the subject:

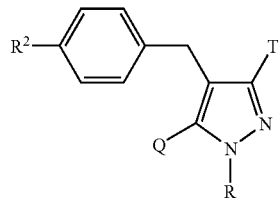

wherein R represents a hydrogen atom, a lower alkyl group or a group forming a prodrug; one of Q and T represents a group represented by the general formula:

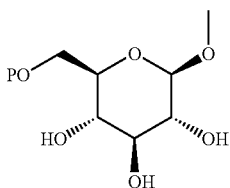

wherein P represents a hydrogen atom or a group forming a prodrug, while the other represents a lower alkyl group or a halo(lower alkyl) group; $R^2$ represents a hydrogen atom, a lower alkyl group, a lower alkoxy group, a lower alkylthio group, a halo(lower alkyl) group or a halogen atom; and with the proviso that P does not represent a hydrogen atom when R represents a hydrogen atom or a lower alkyl group.

11. A method for increasing the amount of urinary glucose excretion as claimed in claim 10, wherein said compound is 3-(6-O-ethoxy-carbonyl-β-D-glucopyranosyloxy)-4-[(4-isopropoxyphenyl)methyl]-1-isopropyl-5-methylpyrazole or a pharmaceutically acceptable salt thereof.

12. A method for increasing the amount of urinary glucose excretion as claimed in claim 10 or 11, wherein said compound or pharmaceutically acceptable salt thereof is orally administered.

13. A method for lowering blood glucose concentration, which comprises administering to a subject in need thereof an amount of a glucopyranosyloxypyrazole derivative of the following general formula, or a pharmaceutically acceptable salt thereof, effective to lower blood glucose concentration in the subject:

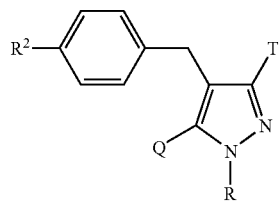

wherein R represents a hydrogen atom, a lower alkyl group or a group forming a prodrug; one of Q and T represents a group represented by the general formula:

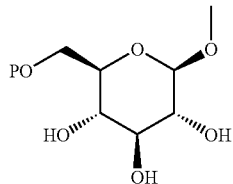

wherein P represents a hydrogen atom or a group forming a prodrug, while the other represents a lower alkyl group or a halo(lower alkyl) group; $R^2$ represents a hydrogen atom, a lower alkyl group, a lower alkoxy group, a lower alkylthio group, a halo(lower alkyl) group or a halogen atom; and with the proviso that P does not represent a hydrogen atom when R represents a hydrogen group or a lower alkyl group.

14. A method for lowering blood glucose concentration as claimed in claim 13, wherein said compound is 3-(6-O-ethoxy-carbonyl-β-D-glucopyranosyloxy)-4-[(4-isopropoxyphenyl)methyl]-1-isopropy 1-5-methylpyrazole or a pharmaceutically acceptable salt thereof.

15. A method for lowering blood glucose concentration as claimed in claim 13 or 14, wherein said compound or pharmaceutically acceptable salt thereof is orally administered.

* * * * *

SEQUENCE LISTING

```
<160> NUMBER OF SEQ ID NOS: 5

<210> SEQ ID NO 1
<211> LENGTH: 20
<212> TYPE: DNA
<213> ORGANISM: Artificial Sequence
<220> FEATURE:
<223> OTHER INFORMATION: Synthetic DNA primer
```

<400> SEQUENCE: 1
atggaggagc acacagaggc                                                    20

<210> SEQ ID NO 2
<211> LENGTH: 20
<212> TYPE: DNA
<213> ORGANISM: Artificial Sequence
<220> FEATURE:
<223> OTHER INFORMATION: Synthetic DNA primer

<400> SEQUENCE: 2
ggcatagaag ccccagagga                                                    20

<210> SEQ ID NO 3
<211> LENGTH: 29
<212> TYPE: DNA
<213> ORGANISM: Artificial Sequence
<220> FEATURE:
<223> OTHER INFORMATION: Synthetic DNA primer

<400> SEQUENCE: 3
aacctcgaga tggaggagca cacagaggc                                          29

<210> SEQ ID NO 4
<211> LENGTH: 29
<212> TYPE: DNA
<213> ORGANISM: Artificial Sequence
<220> FEATURE:
<223> OTHER INFORMATION: Synthetic DNA primer

<400> SEQUENCE: 4
aacaagcttg gcatagaagc cccagagga                                          29

<210> SEQ ID NO 5
<211> LENGTH: 25
<212> TYPE: PRT
<213> ORGANISM: Artificial Sequence
<220> FEATURE:
<223> OTHER INFORMATION: peptide fused to the carboxyl terminal alanine
      residue of human SGLT2

<400> SEQUENCE: 5

Lys Leu Gly Pro Glu Gln Lys Leu Ile Ser Glu Glu Asp Leu Asn Ser
1               5                   10                  15

Ala Val Asp His His His His His His
            20                  25